(12) United States Patent
Dallmeier et al.

(10) Patent No.: US 10,076,564 B2
(45) Date of Patent: Sep. 18, 2018

(54) BACTERIAL ARTIFICIAL CHROMOSOMES

(71) Applicant: KATHOLIEKE UNIVERSITEIT LEUVEN, Leuven (BE)

(72) Inventors: Kai Dallmeier, Leuven (BE); Johan Neyts, Leuven (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 48 days.

(21) Appl. No.: 14/787,098

(22) PCT Filed: Apr. 25, 2014

(86) PCT No.: PCT/EP2014/058459
§ 371 (c)(1),
(2) Date: Oct. 26, 2015

(87) PCT Pub. No.: WO2014/174078
PCT Pub. Date: Oct. 30, 2014

(65) Prior Publication Data
US 2016/0206723 A1    Jul. 21, 2016

(30) Foreign Application Priority Data

Apr. 26, 2013   (GB) .................................. 1307528.8

(51) Int. Cl.
| | | |
|---|---|---|
| *A61K 39/12* | (2006.01) | |
| *C12N 7/00* | (2006.01) | |
| *C12N 15/69* | (2006.01) | |
| *A61K 39/00* | (2006.01) | |

(52) U.S. Cl.
CPC ............... *A61K 39/12* (2013.01); *C12N 7/00* (2013.01); *C12N 15/69* (2013.01); *A61K 2039/5254* (2013.01); *C12N 2770/24134* (2013.01)

(58) Field of Classification Search
None
See application file for complete search history.

(56) References Cited

U.S. PATENT DOCUMENTS

| | | | | |
|---|---|---|---|---|
| 5,866,404 | A | 2/1999 | Bradshaw et al. | |
| 5,874,259 | A | 2/1999 | Szybalski | |
| 6,696,281 | B1 * | 2/2004 | Chambers ............... | A61K 39/12 424/192.1 |
| 6,962,708 | B1 | 11/2005 | Chambers et al. | |
| 2002/0155530 | A1 | 10/2002 | Szybalski et al. | |
| 2003/0049665 | A1 | 3/2003 | Szybalski et al. | |
| 2005/0214838 | A1 | 9/2005 | Szybalski et al. | |
| 2006/0159704 | A1 * | 7/2006 | Bonaldo ................ | C12N 15/86 424/218.1 |
| 2010/0278773 | A1 | 11/2010 | Chambers et al. | |

FOREIGN PATENT DOCUMENTS

| | | |
|---|---|---|
| CN | 101864442 | 10/2010 |
| EP | 0533153 A2 | 3/1993 |
| EP | 1457565 A1 | 9/2004 |
| JP | 2003515335 A | 5/2003 |
| WO | 2000034497 A2 | 6/2000 |
| WO | 0139797 A2 | 6/2001 |
| WO | 2001039797 A2 | 6/2001 |
| WO | 2004033633 A2 | 4/2004 |
| WO | 2005042014 A1 | 5/2005 |
| WO | 2009053988 A1 | 4/2009 |

OTHER PUBLICATIONS

Warden et al., Journal of Biomedicine and Biotechnology, 2010, vol. 2011, Article ID 124595, 16 pages.*
New England BioLabs Inc., pBeloBAC11 map, 1 page, available from and accessed on Jun. 21, 2017: https://www.neb.com/~/media/NebUs/Page%20Images/Tools%20and%20Resources/Interactive%20Tools/DNA%20Sequences%20and%20Maps/pBeloBAC11_map.pdf.*
Almazan et al., "Engineering Infectious cDNAs of Coronavirus as Bacterial Artificial Chromosomes", Methods in Molecular Biology, vol. 454, 2008, pp. 275-291.
Jiang et al., "Molecular and Immunological Characterization of a DNA-Launched Yellow Fever Virus 17D Infectious Clone", Journal of General Virology, vol. 96, 2015, pp. 804-814.
Tretyakova et al., "Plasmid DNA Initiates Replication of Yellow Fever Vaccine in Vitro and Elicits Virus-Specific Immune Response in Mice", Virology, vols. 468-470, 2014, pp. 28-35.
Response to the Official European Communication for EP Application No. 14724009.7, dated Feb. 22, 2017.
European Office Action from EP Application No. 14724009.7, dated Oct. 21, 2016.
Almazan et al., "Engineering Infectious cDNAs of Coronavirus as Bacterial Artificial Chromosomes," Methods in Molecular Biology, 2008, pp. 275-291, vol. 454.
Almazan et al., "Engineering the Largest RNA Virus Genome as an Infectious Bacterial Artificial Chromosome," PNAS, May 9, 2000, pp. 5516-5521, vol. 97, No. 10.
Bredenbeek et al., "A Stable Full-Length Yellow Fever Virus cDNA Clone and Role of Conserved RNA Elements in Flavivirus Replication," Journal of General Virology, 2003, pp. 1261-1268, vol. 84.
Durbin et al., "rDEN2/4Δ30(ME), A Live Attenuated Chimeric Dengue Serotype 2 Vaccine Is Safe and Highly Immunogenic in Healthy Dengue-Naive Adults," Human Vaccines, Nov./Dec. 2006, pp. 255-260, vol. 2, No. 6.

(Continued)

*Primary Examiner* — Stacy B Chen
(74) *Attorney, Agent, or Firm* — Workman Nydegger

(57) ABSTRACT

The invention relates to the use of a bacterial artificial chromosome (BAC) for the preparation of a vaccine, wherein the BAC comprises an inducible bacterial ori sequence for amplification of the BAC to more than 10 copies per bacterial cell. Plus a viral expression cassette comprising a cDNA of an attenuated RNA virus genome and comprising cis-regulatory elements for transcription of said viral cDNA in mammalian cells and for processing of the transcribed RNA into infectious viral RNA.

Figure 1:
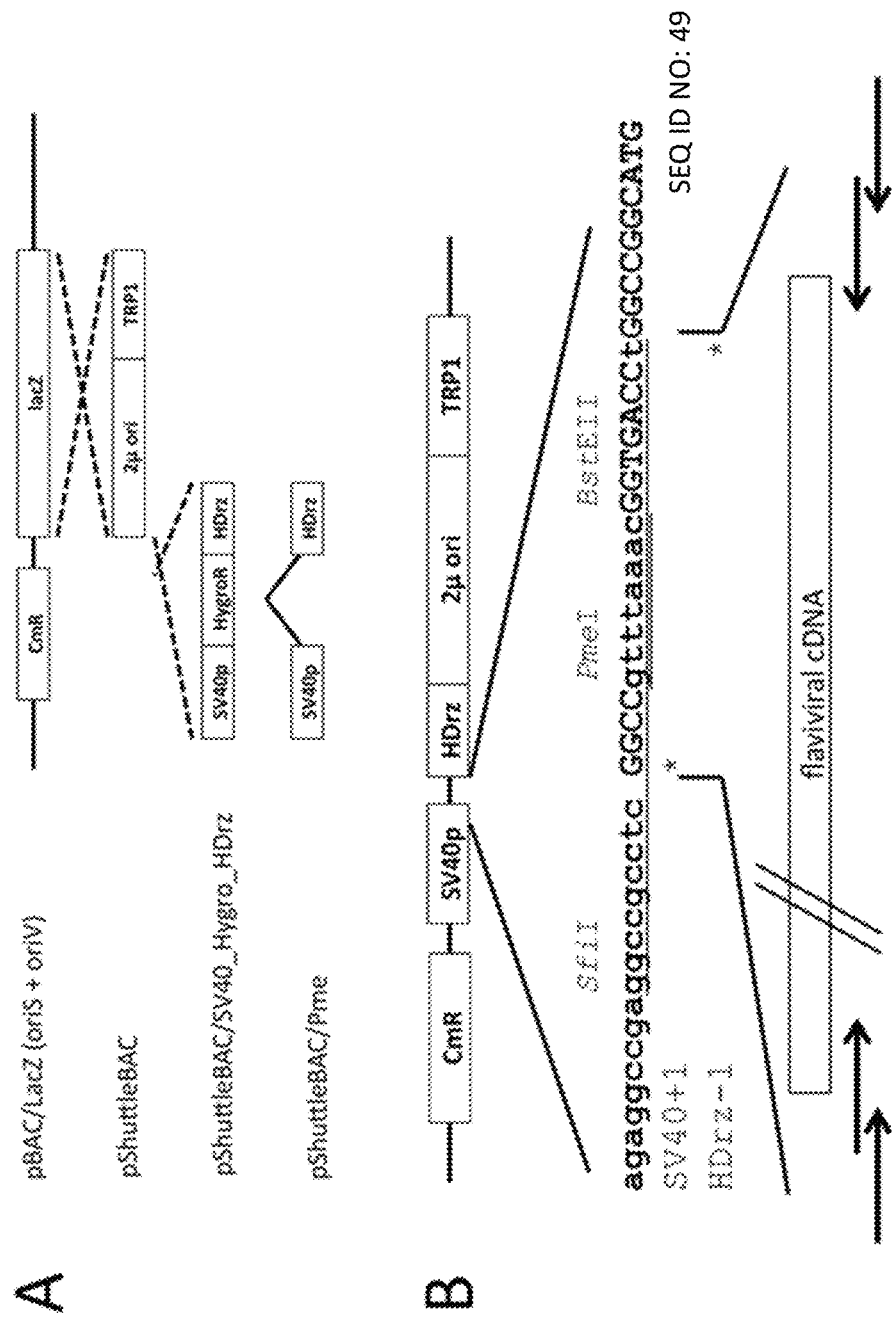

20 Claims, 12 Drawing Sheets
Specification includes a Sequence Listing.

(56) References Cited

OTHER PUBLICATIONS

Edmonds et al., "A Novel Bacterium-Free Method for Generation of Flavivirus Infectious DNA by Circular Polymerase Extension Reaction Allows Accurate Recapitulation of Viral Heterogeneity," Journal of Virology, Feb. 2013, pp. 2367-2372, vol. 87, No. 4.

Enjuanes et al., "Review Article: Coronavirus Derived Expression Systems," Journal of Biotechnology, 2001, pp. 183-204, vol. 88.

Great Britain Search Report for corresponding Great Britain Application No. 1307528.8, dated Oct. 23, 2013.

Fan et al., "An Improved Reverse Genetics System for Generation of Bovine Viral Diarrhea Virus as a BAC cDNA," Journal of Virological Methods, 2008, pp. 309-315, vol. 149.

Hall et al., "DNA Vaccine Coding for the Full-Length infectious Kunjin Virus RNA Protects Mice Against the New York Strain of West Nile Virus," PNAS, Sep. 2, 2003, pp. 10460-10464, vol. 100, No. 18.

Hong et al., "Development of Two Bacterial Artificial Chromosome Shuttle Vectors for a Recombination-Based Cloning and Regulated Expression of Large Genes in Mammalian Cells," Analytical Biochemistry, 2001, pp. 142-148, vol. 291.

International Search Report for corresponding International PCT Application No. PCT/EP2014/058459, dated Aug. 20, 2014.

Kakirde et al., "Gram Negative Shuttle BAC Vector for Heterologous Expression of Metagenomic Libraries," Gene., Apr. 15, 2011, pp. 57-67, vol. 475, No. 2.

Kim et al., "Estimating P-Coverage of Biosynthetic Pathways in DNA Libraries and Screening by Genetic Selection: Biotin Biosynthesis in the Marine Microorganism Chromohalobacter," Molecular BioSystems, 2008, pp. 606-613, vol. 4.

Li et al., "Identification of a Cryptic Prokaryotic Promoter within the cDNA Encoding the 5' End of Dengue Virus RNA Genome," PLoS ONE, e18197, Mar. 2011, pp. 1-9, vol. 6, Issue 3.

Pierro et al., "Infectious Clone Construction of Dengue Virus Type 2, Strain Jamaican 1409, and Characterization of a Conditional E6 Mutation," Journal of General Virology, 2006, pp. 2263-2268, vol. 87.

Pu et al., "Successful Propagation of Flavivirus Infectious cDNAs by a Novel Method to Reduce the Cryptic Bacterial Promoter Activity of Virus Genomes," Journal of Virology, Mar. 2011, pp. 2927-2941, vol. 85, No. 6.

Rice et al., "Transcription of Infectious Yellow Fever RNA from Full-Length cDNA Templates Produced by In Vitro Ligation," The New Biologist, Dec. 1989, pp. 285-296, vol. 1, No. 3.

Ward et al., "Plasmid DNA Encoding Replicating Foot-and-Mouth Disease Virus Genomes Induces Antiviral Immune Responses in Swine," Journal of Virology, Oct. 1997, pp. 7442-7447, vol. 71, No. 10.

Westenberg et al., "*Escherichia coli* MW005: Lambda Red-Mediated Recombineering and Copy-Number Induction of oriV-Equipped Constructs in a Single Host," BMC Biotechnology, 2010, pp. 1-8, vol. 10, No. 27.

Wild et al., "Conditionally Amplifiable BACs: Switching from Single-Copy to High-Copy Vectors and Genomic Clones," Genome Research, 2002, pp. 1434-1444, vol. 12.

Wild et al., "Single-Copy/High-Copy (SC/HC) pBAC/oriV Novel Vectors for Genomics and Gene Expression," Plasmid, Mar. 1, 2001, pp. 142-143, vol. 45, No. 2.

Yun et al., "Development and Application of a Reverse Genetics System for Japanese Encephalitis Virus," Journal of Virology, Jun. 2003, pp. 6450-6465, vol. 77, No. 11.

European Office Action from EP Application No. 14724009.7, dated Jul. 10, 2017.

Chinese Office Action from CN Application No. 201480023688.3, dated Aug. 14, 2017.

Almazan et al., "Engineering Infectious cDNAs of Coronavirus as Bacterial Artificial Chromosomes," Methods Molecular Biology, vol. 1282, 2015, pp. 135-152.

Yang et al., "Application of Bacterial Artificial Chromosome System in the Research of MDV" [Abstract], vol. 45, No. 3, 2011, pp. 52-55.

Response in EP Application No. 14724009.7, dated Oct. 20, 2017.

Japanese Office Action from JP Application No. 2016-509489, dated Feb. 27, 2018.

* cited by examiner

Figure 12

ID CHROMOSOMES

SEQUENCE LISTING

```
<160> NUMBER OF SEQ ID NOS: 51

<210> SEQ ID NO 1
<211> LENGTH: 283
<212> TYPE: DNA
<213> ORGANISM: Simian virus 40
<220> FEATURE:
<221> NAME/KEY: misc_feature
<223> OTHER INFORMATION: SV40 promoter

<400> SEQUENCE: 1
cctgtggaat gtgtgtcagt tagggtgtgg aaagtcccca ggctccccag caggcagaag      60
tatgcaaagc atgcatctca attagtcagc aaccaggtgt ggaaagtccc caggctcccc     120
agcaggcaga agtatgcaaa gcatgcatct caattagtca gcaaccatag tcccgcccct     180
aactccgccc atcccgcccc taactccgcc cagttccgcc cattctccgc cccatggctg     240
actaattttt tttatttatg cagaggccga ggccgcctcg gcc                       283

<210> SEQ ID NO 2
<211> LENGTH: 85
<212> TYPE: DNA
<213> ORGANISM: Artificial Sequence
<220> FEATURE:
<223> OTHER INFORMATION: synthetic cDNA of the genomic ribozyme of
      hepatitis delta virus (HDrz)

<400> SEQUENCE: 2
tggccggcat ggtcccagcc tcctcgctgg cgccggctgg gcaacattcc gaggggaccg      60
tcccctcggt aatggcgaat gggac                                           85
```

<210> SEQ ID NO 3
<211> LENGTH: 10862
<212> TYPE: DNA
<213> ORGANISM: Artificial Sequence
<220> FEATURE:
<223> OTHER INFORMATION: Synthetic cDNA of YFV-17D

<400> SEQUENCE: 3

```
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta tcttttttctt tttgttcaac attttgactg aaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgacgggtgg     480
agtgaccttg gtgcggaaaa acagatggtt gctcctaaat gtgacatctg aggacctcgg     540
gaaacattc tctgtgggca caggcaactg cacaacaaac attttggaag ccaagtactg     600
gtgcccagac tcaatggaat acaactgtcc caatctcagt ccaagagagg agccagatga     660
cattgattgc tggtgctatg gggtggaaaa cgttagagtc gcatatggta agtgtgactc     720
agcaggcagg tctaggaggt caagaagggc cattgacttg cctacgcatg aaaaccatgg     780
tttgaagacc cggcaagaaa atggatgac tggaagaatg ggtgaaaggc aactccaaaa     840
gattgagaga tggttcgtga ggaaccccctt ttttgcagtg acggctctga ccattgccta     900
ccttgtggga agcaacatga cgcaacgagt cgtgattgcc ctactggtct ggctgttgg     960
tccggcctac tcagctcact gcattggaat tactgacagg gatttcattg aggggtgca    1020
tggaggaact tgggtttcag ctaccctgga gcaagacaag tgtgtcactg ttatggcccc    1080
tgacaagcct tcattggaca tctcactaga cagtagcc attgatagac ctgctgaggt    1140
gaggaaagtg tgttacaatg cagttctcac tcatgtgaag attaatgaca gtgccccag    1200
cactggagag gcccacctag ctgaagagaa cgaagggac aatgcgtgca agcgcactta    1260
ttctgataga ggctggggca atggctgtgg cctatttggg aaaggagca ttgtggcatg    1320
cgccaaattc acttgtgcca aatccatgag tttgtttgag gttgatcaga ccaaaattca    1380
gtatgtcatc agagcacaat tgcatgtagg ggccaagcag gaaaattgga ataccgacat    1440
taagactctc aagtttgatg ccctgtcagg ctcccaggaa gtcgagttca ttgggtatgg    1500
aaaagctaca ctggaatgcc aggtgcaaac tgccggtgga ctttggtaaca gttacatcgc    1560
tgagatggaa acagagagct ggatagtgga cagacagtgg gcccaggact tgaccctgcc    1620
atggcagagt ggaagtggcg gggtgtggag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgtttctt gcagagtgaa attgtcagct tgacactca aggggacatc    1860
ctacaaaata tgcactgaca aaatgttttt tgtcaagaac ccaactgaca ctggccatgg    1920
cactgttgtg atgcaggtga aagtgtcaaa aggagccccc tgcaggattc agtgatagt    1980
agctgatgat cttacagcgg caatcaataa aggcattttg gttacagtta accccatcgc    2040
ctcaaccaat gatgatgaag tgctgattga ggtgaaccca cctttttgga acagctacat    2100
```

```
tatcgttggg agaggagatt cacgtctcac ttaccagtgg cacaaagagg aagctcaat    2160 aggaaagttg ttcactcaga ccatgaaagg cgtggaacgc ctggccgtca tgggagacac    2220
cgcctgggat ttcagctccg ctggagggtt cttcacttcg gttgggaaag gaattcatac    2280
ggtgtttggc tctgcctttc aggggctatt tggcggcttg aactggataa caaaggtcat    2340
catgggggcg gtacttatat gggttggcat caacacaaga aacatgacaa tgtccatgag    2400
catgatcttg gtaggagtga tcatgatgtt tttgtctcta ggagttgggg cggatcaagg    2460
atgcgccatc aactttggca agagagagct caagtgcgga gatggtatct tcatatttag    2520
agactctgat gactggctga acaagtactc atactatcca gaagatccctg tgaagcttgc    2580 atcaatagtg aaagcctctt ttgaagaagg aagtgtggc ctaaattcag ttgactccct    2640
tgagcatgag atgtggagaa gcagggcaga tgagatcaat gccattttg aggaaaacga    2700 ggtggacatt tctgttgtcg tgcaggatcc aaagaatgtt taccagagag gaactcatcc    2760
attttccaga attcgggatg gtctgcagta tggttggaag acttggggta agaaccttgt    2820
gttctcccca gggaggaaga atggaagctt catcatagat ggaaagtcca ggaaagaatg    2880
cccgttttca aaccgggtct ggaattcttt ccagatagag gagtttggga cgggagtgtt    2940
caccacacgc gtgtacatgg acgcagtctt tgaatacacc atagactgcg atggatctat    3000
cttgggtgca gcggtgaacg gaaaaaagag tgcccatggc tctccaacat tttggatggg    3060
aagtcatgaa gtaaatggga catggatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtcccctt ttggtttggt    3540 gagcatgatg atagcaatgg aagtggtcct aaggaaaaga cagggaccaa agcaaatgtt    3600
ggttggagga gtagtgctct gggagcaat gctggtcggg caagtaactc tccttgattt    3660
gctgaaactc acagtggctg tgggattgca tttccatgag atgaacaatg gaggagacgc    3720
catgtatatg gcgttgattg ctgccttttc aatcagacca gggctgctca tcggcttttgg    3780 gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgccct    3960 catggctctg ttgacacctg tcactatggc tgaggtgaga cttgccgcaa tgttcttttg    4020
tgccgtggtt atcataggg tccttccacca gaatttcaag gacacctcca tgcagaagac    4080
tatacctctg gtggccctca cactcacatc ttacctgggc ttgacacaac cttttttggg    4140
cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctgggag    4320
ggtggatggc ctagagctca agaagcttgg tgaagtttca tgggaagagg aggcggagat    4380
cagcgggagt tccgcccgct atgatgtggc actcagtgaa caagggggagt tcaagctgct    4440
```

-continued

```
ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggt gttccacaca atgtggcatg tcacaagagg    4740
agctttcctt gtcaggaatg gcaagaagtt gattccatct tgggcttcag taaaggaaga    4800
ccttgtcgcc tatggtggct catggaagtt ggaaggcaga tgggatggag aggaagaggt    4860
ccagttgatc gcggctgttc caggaaagaa cgtggtcaac gtccagacaa aaccgagctt    4920
gttcaaagtg aggaatgggg gagaaatcgg ggctgtcgct cttgactatc cgagtggcac    4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
ggaggctttt cacggcctgg acgtgaaatt ccacacacag gcttttttccg ctcacggcag    5340
cgggagagaa gtcattgatg ccatgtgcca tgccacccta acttacagga tgttggaacc    5400
aactagggtt gttaactggg aagtgatcat tatggatgaa gcccattttt tggatccagc    5460
tagcatagcc gctagaggtt gggcagcgca cagagctagg gcaaatgaaa gtgcaacaat    5520
cttgatgaca gccacaccgc ctgggactag tgatgaattt ccacattcaa atggtgaaat    5580
agaagatgtt caaacggaca tacccagtga gccctggaac acagggcatg actggatcct    5640
agctgacaaa aggcccacgg catggttcct tccatccatc agagctgcaa atgtcatggc    5700
tgcctctttg cgtaaggctg aaagagtgt ggtggtcctg aacaggaaaa cctttgagag    5760
agaatacccc acgataaagc agaagaaacc tgactttata ttggccactg acatagctga    5820
aatgggagcc aacctttgcg tggagcgagt gctggattgc aggacggctt ttaagcctgt    5880
gcttgtggat gaagggagga aggtggcaat aaaagggcca cttcgtatct ccgcatcctc    5940
tgctgctcaa aggaggggc gcattgggag aaatcccaac agagatggag actcatacta    6000
ctattctgag cctacaagtg aaaataatgc ccaccacgtc tgctggttgg aggcctcaat    6060
gctcttggac aacatggagg tgagggtgg aatggtcgcc ccactctatg gcgttgaagg    6120
aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtggtg ttttgaaggc cctgaggaac atgagatctt    6300
gaatgacagc ggtgaaacag tgaagtgcag ggctcctgga ggagcaaaga agcctctgcg    6360
cccaaggtgg tgtgatgaaa gggtgtcatc tgaccagagt gcgctgtctg aatttattaa    6420
gtttgctgaa ggtaggaggg gagctgctga agtgctagtt gtgctgagtg aactccctga    6480
tttcctggct aaaaaaggtg gagaggcaat ggataccatc agtgtgttcc tccactctga    6540
ggaaggctct agggcttacc gcaatgcact atcaatgatg cctgaggcaa tgacaatagt    6600
catgctgttt atactggctg gactactgac atcgggaatg gtcatctttt tcatgtctcc    6660
caaaggcatc agtagaatgt ctatggcgat gggcacaatg gccggctgtg gatatctcat    6720
gttccttgga ggcgtcaaac ccactcacat ctccctatgtc atgctcatat tctttgtcct    6780
gatggtggtt gtgatccccg agccagggca acaaaggtcc atccaagaca accaagtggc    6840
```

```
atacctcatt attggcatcc tgacgctggt ttcagcggtg gcagccaacg agctaggcat    6900
gctggagaaa accaaagagg acctctttgg gaagaagaac ttaattccat ctagtgcttc    6960
accctggagt tggccggatc ttgacctgaa gccaggagct gcctggacag tgtacgttgg    7020
cattgttaca atgctctctc caatgttgca ccactggatc aaagtcgaat atggcaacct    7080
gtctctgtct ggaatagccc agtcagcctc agtcctttct ttcatggaca aggggatacc    7140
attcatgaag atgaatatct cggtcataat gctgctggtc agtggctgga attcaataac    7200
agtgatgcct ctgctctgtg catagggtg cgccatgctc cactggtctc tcattttacc    7260
tggaatcaaa gcgcagcagt caaagcttgc acagagaagg gtgttccatg gcgttgccga    7320
gaaccctgtg gttgatggga atccaacagt tgacattgag gaagctcctg aaatgcctgc    7380
cctttatgag aagaaactgg ctctatatct ccttcttgct ctcagcctag cttctgttgc    7440
catgtgcaga acgccctttt cattggctga aggcattgtc ctagcatcag ctgccttagg    7500
gccgctcata gagggaaaca ccagccttct ttggaatgga cccatggctg tctccatgac    7560
aggagtcatg aggggaatc actatgcttt tgtgggagtc atgtacaatc tatggaagat    7620
gaaaactgga cgccggggga gcgcgaatgg aaaaactttg ggtgaagtct ggaagaggga    7680
actgaatctg ttggacaagc gacagtttga gttgtataaa aggaccgaca ttgtggaggt    7740
ggatcgtgat acggcacgca ggcatttggc cgaagggaag gtggacaccg gggtggcggt    7800
ctccaggggg accgcaaagt taaggtggtt ccatgagcgt ggctatgtca agctggaagg    7860
tagggtgatt gacctggggt gtggccgcgg aggctggtgt tactacgctg ctgcgcaaaa    7920
ggaagtgagt ggggtcaaag gatttactct tggaagagac ggccatgaga acccatgaa    7980
tgtgcaaagt ctgggatgga acatcatcac cttcaaggac aaaactgata tccaccgcct    8040
agaaccagtg aaatgtgaca cccttttgtg tgacattgga gagtcatcat cgtcatcggt    8100
cacagagggg gaaaggaccg tgagagttct tgatactgta gaaaaatggc tggcttgtgg    8160
ggttgacaac ttctgtgtga aggtgttagc tccatacatg ccagatgttc ttgagaaaact    8220
ggaattgctc caaggaggt ttggcggaac agtgatcagg aaccctctct ccaggaattc    8280
cactcatgaa atgtactacg tgtctggagc ccgcagcaat gtcacattta ctgtgaacca    8340
aacatcccgc ctcctgatga ggagaatgag gcgtccaact ggaaaagtga ccctggaggc    8400
tgacgtcatc ctcccaattg ggacacgcag tgttgagaca gacaagggac ccctggacaa    8460
agaggccata aagaaagggt tgagaggat aaaatctgag tacatgacct cttggtttta    8520
tgacaatgac aacccctaca ggacctggca ctactgtggc tcctatgtca caaaaacctc    8580
aggaagtgcg gcgagcatgg taaatggtgt tattaaaatt ctgacatatc catgggacag    8640
gatagaggag gtcacaagaa tggcaatgac tgacacaacc cctttggac agcaaagagt    8700
gtttaaagaa aaagttgaca ccagagcaaa ggatccacca gcgggaacta ggaagatcat    8760
gaaagttgtc aacaggtggc tgttccgcca cctggccaga aaaagaacc ccagactgtg    8820
cacaaaggaa gaatttattg caaaagtccg aagtcatgca gccattggag cttacctgga    8880
agaacaagaa cagtggaaga ctgccaatga ggctgtccaa gacccaaagt ctgggaact    8940
ggtggatgaa gaaaggaagc tgcaccaaca aggcaggtgt cggacttgtg tgtacaacat    9000
gatggggaaa agagagaaga agctgtcaga gtttgggaaa gcaaagggaa gccgtgccat    9060
atggtatatg tggctgggag cgcggtatct tgagtttgag gccctgggat tcctgaatga    9120
ggaccattgg gcttccaggg aaaactcagg aggaggagtg gaaggcattg gcttacaata    9180
```

-continued

```
cctaggatat gtgatcagag acctggctgc aatggatggt ggtggattct acgcggatga   9240
caccgctgga tgggacacgc gcatcacaga ggcagacctt gatgatgaac aggagatctt   9300
gaactacatg agcccacatc acaaaaaact ggcacaagca gtgatggaaa tgacatacaa   9360
gaacaaagtg gtgaaagtgt tgagaccagc cccaggaggg aaagcctaca tggatgtcat   9420
aagtcgacga gaccagagag gatccgggca ggtagtgact tatgctctga acaccatcac   9480
caacttgaaa gtccaattga tcagaatggc agaagcagag atggtgatac atcaccaaca   9540
tgttcaagat tgtgatgaat cagttctgac caggctggag gcatggctca ctgagcacgg   9600
atgtgacaga ctgaagagga tggcggtgag tggagacgac tgtgtggtcc ggcccatcga   9660
tgacaggttc ggcctggccc tgtcccatct caacgccatg tccaaggtta gaaaggacat   9720
atctgaatgg cagccatcaa aagggtggaa tgattgggag aatgtgccct tctgttccca   9780
ccacttccat gaactacagc tgaaggatgg caggaggatt gtggtgcctt gccgagaaca   9840
ggacgagctc attgggagag gaagggtgtc tccaggaaac ggctggatga tcaaggaaac   9900
agcttgcctc agcaaagcct atgccaacat gtggtcactg atgtattttc acaaaaggga   9960
catgaggcta ctgtcattgg ctgtttcctc agctgttccc acctcatggg ttccacaagg  10020
acgcacaaca tggtcgattc atgggaaagg ggagtggatg accacggaag acatgcttga  10080
ggtgtggaac agagtatgga taaccaacaa cccacacatg caggacaaga caatggtgaa  10140
aaaatggaga gatgtccctt atctaaccaa gagacaagac aagctgtgcg gatcactgat  10200
tggaatgacc aatagggcca cctgggcctc ccacatccat ttagtcatcc atcgtatccg  10260
aacgctgatt ggacaggaga aatacactga ctacctaaca gtcatggaca ggtattctgt  10320
ggatgctgac ctgcaactgg gtgagcttat ctgaaacacc atctaacagg aataaccggg  10380
atacaaacca cgggtggaga accggactcc ccacaacctg aaaccgggat ataaaccacg  10440
gctggagaac cgggctccgc acttaaaatg aaacagaaac cgggataaaa actacggatg  10500
gagaaccgga ctccacacat tgagacagaa gaagttgtca gcccagaacc ccacacgagt  10560
tttgccactg ctaagctgtg aggcagtgca ggctgggaca gccgacctcc aggttgcgaa  10620
aaacctggtt tctgggacct cccaccccag agtaaaaaga acggagcctc cgctaccacc  10680
ctcccacgtg gtggtagaaa gacggggtct agaggttaga ggagaccctc cagggaacaa  10740
atagtgggac catattgacg ccagggaaag accggagtgg ttctctgctt ttcctccaga  10800
ggtctgtgag cacagtttgc tcaagaataa gcagaccttt ggatgacaaa cacaaaacca  10860
ct                                                                 10862
```

```

<210> SEQ ID NO 4
<211> LENGTH: 21061
<212> TYPE: DNA
<213> ORGANISM: Artificial Sequence
<220> FEATURE:
<223> OTHER INFORMATION: Synthetic construct pShuttle/YF17D

<400> SEQUENCE: 4
agtaaatcct gtgtgctaat tgaggtgcat tggtctgcaa atcgagttgc taggcaataa     60
acacatttgg attaatttta atcgttcgtt gagcgattag cagagaactg accagaacat    120
gtctggtcgt aaagctcagg gaaaaaccct gggcgtcaat atggtacgac gaggagttcg    180
ctccttgtca aacaaaataa aacaaaaaac aaaacaaatt ggaaacagac ctggaccttc    240
aagaggtgtt caaggattta tctttttctt tttgttcaac attttgactg gaaaaaagat    300
cacagcccac ctaaagaggt tgtggaaaat gctggaccca agacaaggct tggctgttct    360
```

```
aaggaaagtc aagagagtgg tggccagttt gatgagagga ttgtcctcaa ggaaacgccg      420
ttcccatgat gttctgactg tgcaattcct aattttggga atgctgttga tgacgggtgg      480
agtgaccttg gtgcggaaaa acagatggtt gctcctaaat gtgacatctg aggacctcgg      540
gaaaacattc tctgtgggca caggcaactg cacaacaaac attttggaag ccaagtactg      600
gtgcccagac tcaatggaat acaactgtcc caatctcagt ccaagagagg agccagatga      660
cattgattgc tggtgctatg gggtggaaaa cgttagagtc gcatatggta agtgtgactc      720
agcaggcagg tctaggaggt caagaagggc cattgacttg cctacgcatg aaaaccatgg      780
tttgaagacc cggcaagaaa aatggatgac tggaagaatg ggtgaaaggc aactccaaaa      840
gattgagaga tggttcgtga ggaaccccct ttttgcagtg acggctctga ccattgccta      900
ccttgtggga agcaacatga cgcaacgagt cgtgattgcc ctactggtct ggctgttggg      960
tccggcctac tcagctcact gcattggaat tactgacagg gatttcattg agggggtgca     1020
tggaggaact tgggtttcag ctaccctgga gcaagacaag tgtgtcactg ttatggcccc     1080
tgacaagcct tcattggaca tctcactaga gacagtagcc attgatagac ctgctgaggt     1140
gaggaaagtg tgttacaatg cagttctcac tcatgtgaag attaatgaca agtgccccag     1200
cactggagag gcccacctag ctgaagagaa cgaaggggac aatgcgtgca agcgcactta     1260
ttctgataga ggctggggca atggctgtgg cctatttggg aaagggagca ttgtggcatg     1320
cgccaaattc acttgtgcca aatccatgag tttgtttgag gttgatcaga ccaaaattca     1380
gtatgtcatc agagcacaat tgcatgtagg ggccaagcag gaaaattgga ataccgacat     1440
taagactctc aagtttgatg ccctgtcagg ctcccaggaa gtcgagttca ttgggtatgg     1500
aaaagctaca ctggaatgcc aggtgcaaac tgccgtggac tttggtaaca gttacatcgc     1560
tgagatggaa acagagagct ggatagtgga cagacagtgg gcccaggact tgaccctgcc     1620
atggcagagt ggaagtggcg gggtgtggag agagatgcat catcttgtcg aatttgaacc     1680
tccgcatgcc gccactatca gagtactggc cctgggaaac caggaaggct ccttgaaaac     1740
agctcttact ggcgcaatga gggttacaaa ggacacaaat gacaacaacc tttacaaact     1800
acatggtgga catgtttctt gcagagtgaa attgtcagct ttgacactca aggggacatc     1860
ctacaaaata tgcactgaca aaatgttttt tgtcaagaac ccaactgaca ctggccatgg     1920
cactgttgtg atgcaggtga aagtgtcaaa aggagccccc tgcaggattc cagtgatagt     1980
agctgatgat cttacagcgg caatcaataa aggcattttg gttacagtta accccatcgc     2040
ctcaaccaat gatgatgaag tgctgattga ggtgaaccca ccttttggag acagctacat     2100
tatcgttggg agaggagatt cacgtctcac ttaccagtgg cacaaagagg aagctcaat      2160 aggaaagttg ttcactcaga ccatgaaagg cgtggaacgc ctggccgtca tgggagacac     2220
cgcctgggat ttcagctccg ctggagggtt cttcacttcg gttgggaaag gaattcatac     2280
ggtgtttggc tctgcctttc aggggctatt tggcggcttg aactggataa caaaggtcat     2340
catgggggcg gtacttatat gggttggcat caacacaaga aacatgacaa tgtccatgag     2400
catgatcttg gtaggagtga tcatgatgtt tttgtctcta ggagttgggg cggatcaagg     2460
atgcgccatc aactttggca agagagagct caagtgcgga gatggtatct tcatatttag     2520
agactctgat gactggctga acaagtactc atactatcca gaagatcctg tgaagcttgc     2580
atcaatagtg aaagcctctt ttgaagaagg gaagtgtggc ctaaattcag ttgactccct     2640
tgagcatgag atgtgggaga gcagggcaga tgagatcaat gccatttttg aggaaaacga     2700
```

```
ggtggacatt tctgttgtcg tgcaggatcc aaagaatgtt taccagagag gaactcatcc    2760
attttccaga attcgggatg gtctgcagta tggttggaag acttggggta agaaccttgt    2820
gttctcccca gggaggaaga atggaagctt catcatagat ggaaagtcca ggaaagaatg    2880
cccgttttca aaccgggtct ggaattcttt ccagatagag gagtttggga cgggagtgtt    2940
caccacacgc gtgtacatgg acgcagtctt tgaatacacc atagactgcg atggatctat    3000
cttgggtgca gcggtgaacg gaaaaaagag tgcccatggc tctccaacat tttggatggg    3060
aagtcatgaa gtaaatggga catggatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtcccctt ttggtttggt    3540
gagcatgatg atagcaatgg aagtggtcct aaggaaaaga cagggaccaa agcaaatgtt    3600
ggttggagga gtagtgctct gggagcaat gctggtcggg caagtaactc tccttgattt    3660
gctgaaactc acagtggctg tgggattgca tttccatgag atgaacaatg gaggagacgc    3720
catgtatatg gcgttgattg ctgccttttc aatcagacca gggctgctca tcggctttgg    3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgccct    3960
catggctctg ttgacacctg tcactatggc tgaggtgaga cttgccgcaa tgttcttttg    4020
tgccgtggtt atcataggg tccttccacca gaatttcaag gacacctcca tgcagaagac    4080
tatacctctg gtggccctca cactcacatc ttacctgggc ttgacacaac cttttttggg    4140
cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctggag    4320
ggtggatggg ctagagctca agaagcttgg tgaagtttca tgggaagagg aggcggagat    4380
cagcgggagt tccgcccgct atgatgtggc actcagtgaa caaggggagt tcaagctgct    4440
ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggt gttccacaca atgtggcatg tcacaagagg    4740
agcttttcctt gtcaggaatg gcaagaagtt gattccatct tgggcttcag taaaggaaga    4800
ccttgtcgcc tatggtggct catgaagtt ggaaggcaga tgggatggag aggaagaggt    4860
ccagttgatc gcggctgttc caggaaagaa cgtggtcaac gtccagacaa aaccgagctt    4920
gttcaaagtg aggaatgggg gagaaatcgg ggctgtcgct cttgactatc cgagtggcac    4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
```

```
aaaggaggag ctccaagaga tcccgacaat gctaaagaaa ggaatgacaa ctgtccttga      5160
ttttcatcct ggagctggga agacaagacg tttcctccca cagatcttgg ccgagtgcgc      5220
acggagacgc ttgcgcactc ttgtgttggc ccccaccagg gttgttcttt ctgaaatgaa      5280
ggaggctttt cacggcctgg acgtgaaatt ccacacacag gcttttccg ctcacggcag       5340 cgggagagaa gtcattgatg ccatgtgcca tgccaccta acttacagga tgttggaacc      5400
aactagggtt gttaactggg aagtgatcat tatggatgaa gcccattttt tggatccagc      5460
tagcatagcc gctagaggtt gggcagcgca cagagctagg gcaaatgaaa gtgcaacaat      5520
cttgatgaca gccacaccgc ctgggactag tgatgaattt ccacattcaa atggtgaaat      5580
agaagatgtt caaacggaca tacccagtga gccctggaac acagggcatg actggatcct      5640
agctgacaaa aggcccacgg catggttcct tccatccatc agagctgcaa atgtcatggc      5700
tgcctctttg cgtaaggctg aaagagtgt ggtggtcctg aacaggaaaa cctttgagag       5760 agaataccc cgataaagc agaagaaacc tgactttata ttggccactg acatagctga       5820
aatgggagcc aacctttgcg tggagcgagt gctggattgc aggacggctt ttaagcctgt      5880
gcttgtggat gaagggagga aggtggcaat aaaagggcca cttcgtatct ccgcatcctc      5940
tgctgctcaa aggagggggc gcattgggag aaatcccaac agagatggag actcatacta      6000
ctattctgag cctacaagtg aaaataatgc ccaccacgtc tgctggttgg aggcctcaat      6060
gctcttggac aacatggagg tgaggggtgg aatggtcgcc ccactctatg gcgttgaagg      6120
aactaaaaca ccagttttccc ctggtgaaat gagactgagg gatgaccaga ggaaagtctt     6180
cagagaacta gtgaggaatt gtgacctgcc cgtttggctt tcgtggcaag tggccaaggc      6240
tggtttgaag acgaatgatc gtaagtggtg ttttgaaggc cctgaggaac atgagatctt      6300
gaatgacagc ggtgaaacag tgaagtgcag ggctcctgga ggagcaaaga agcctctgcg      6360
cccaaggtgg tgtgatgaaa gggtgtcatc tgaccagagt gcgctgtctg aatttattaa      6420
gtttgctgaa ggtaggaggg gagctgctga agtgctagtt gtgctgagtg aactccctga      6480
tttcctggct aaaaaaggtg gagaggcaat ggataccatc agtgtgttcc tccactctga      6540
ggaaggctct agggcttacc gcaatgcact atcaatgatg cctgaggcaa tgacaatagt      6600
catgctgttt atactggctg gactactgac atcgggaatg gtcatctttt tcatgtctcc      6660
caaaggcatc agtagaatgt ctatggcgat gggcacaatg gccggctgtg gatatctcat      6720
gttccttgga ggcgtcaaac ccactcacat ctcctatgtc atgctcatat tctttgtcct      6780
gatggtggtt gtgatccccg agccagggca acaaaggtcc atccaagaca accaagtggc      6840
atacctcatt attggcatcc tgacgctggt ttcagcggtg cagccaacg agctaggcat       6900 gctggagaaa accaaagagg acctctttgg gaagaagaac ttaattccat ctagtgcttc      6960
accctggagt tggccggatc ttgacctgaa gccaggagct gcctggacag tgtacgttgg      7020
cattgttaca atgctctctc caatgttgca ccactggatc aaagtcgaat atggcaacct     7080
gtctctgtct ggaatagccc agtcagcctc agtcctttct ttcatggaca agggatacc      7140 attcatgaag atgaatatct cggtcataat gctgctggtc agtggctgga attcaataac      7200
agtgatgcct ctgctctgtg gcataggtg cgccatgctc cactggtctc tcattttacc      7260
tggaatcaaa gcgcagcagt caaagcttgc acagagaagg gtgttccatg cgttgccga      7320 gaaccctgtg gttgatggga atccaacagt tgacattgag gaagctcctg aaatgcctgc      7380
cctttatgag aagaaactgg ctctatatct ccttcttgct ctcagcctag cttctgttgc      7440
```

```
catgtgcaga acgcccttttt cattggctga aggcattgtc ctagcatcag ctgccttagg    7500
gccgctcata gagggaaaca ccagccttct ttggaatgga cccatggctg tctccatgac    7560
aggagtcatg aggggggaatc actatgcttt tgtgggagtc atgtacaatc tatggaagat   7620
gaaaactgga cgccggggga gcgcgaatgg aaaaactttg ggtgaagtct ggaagaggga    7680
actgaatctg ttggacaagc gacagtttga gttgtataaa aggaccgaca ttgtggaggt    7740
ggatcgtgat acggcacgca ggcatttggc cgaagggaag gtggacaccg gggtggcggt    7800
ctccaggggg accgcaaagt taaggtggtt ccatgagcgt ggctatgtca agctggaagg    7860
tagggtgatt gacctggggt gtggccgcgg aggctggtgt tactacgctg ctgcgcaaaa    7920
ggaagtgagt ggggtcaaag gatttactct tggaagagac ggccatgaga acccatgaa    7980 tgtgcaaagt ctgggatgga acatcatcac cttcaaggac aaaactgata tccaccgcct    8040
agaaccagtg aaatgtgaca ccctttttgtg tgacattgga gagtcatcat cgtcatcggt    8100
cacagagggg gaaaggaccg tgagagttct tgatactgta gaaaaatggc tggcttgtgg    8160
ggttgacaac ttctgtgtga aggtgttagc tccatacatg ccagatgttc ttgagaaaact   8220 ggaattgctc caaaggaggt ttggcggaac agtgatcagg aaccctctct ccaggaattc    8280
cactcatgaa atgtactacg tgtctggagc ccgcagcaat gtcacattta ctgtgaacca    8340
aacatcccgc ctcctgatga ggagaatgag gcgtccaact ggaaaagtga ccctggaggc    8400
tgacgtcatc ctcccaattg ggacacgcag tgttgagaca gacaagggac ccctggacaa    8460
agaggccata aagaaaggg ttgagaggat aaaatctgag tacatgacct cttggttttta     8520 tgacaatgac aaccccctaca ggacctggca ctactgtggc tcctatgtca caaaaacctc    8580
aggaagtgcg gcgagcatgg taaatggtgt tattaaaatt ctgacatatc catgggacag    8640
gatagaggag gtcacaagaa tggcaatgac tgacacaacc ccttttggac agcaaagagt    8700
gtttaaagaa aaagttgaca ccagagcaaa ggatccacca gcgggaacta ggaagatcat    8760
gaaagttgtc aacaggtggc tgttccgcca cctggccaga gaaaagaacc ccagactgtg    8820
cacaaaggaa gaatttattg caaaagtccg aagtcatgca gccattggag cttacctgga    8880
agaacaagaa cagtggaaga ctgccaatga ggctgtccaa gacccaaagt ctgggaact    8940 ggtggatgaa gaaaggaagc tgcaccaaca aggcaggtgt cggacttgtg tgtacaacat    9000
gatggggaaa agagagaaga agctgtcaga gtttgggaaa gcaaagggaa gccgtgccat    9060
atggtatatg tggctgggag cgcggtatct tgagtttgag gccctgggat tcctgaatga    9120
ggaccattgg gcttccaggg aaaactcagg aggaggagtg gaaggcattg gcttacaata    9180
cctaggatat gtgatcagag acctggctgc aatggatggt ggtggtggattct acgcggatga   9240 caccgctgga tgggacacgc gcatcacaga ggcagacctt gatgatgaac aggagatctt    9300
gaactacatg agcccacatc acaaaaaact ggcacaagca gtgatggaaa tgacatacaa    9360
gaacaaagtg gtgaaagtgt tgagaccagc cccaggaggg aaagcctaca tggatgtcat    9420
aagtcgacga gaccagagag gatccgggca ggtagtgact tatgctctga acaccatcac    9480
caacttgaaa gtccaattga tcagaatggc agaagcagag atggtgatac atcaccaaca    9540
tgttcaagat tgtgatgaat cagttctgac caggctggag gcatggctca ctgagcacgg    9600
atgtgacaga ctgaagagga tggcggtgag tggagacgac tgtgtggtcc ggcccatcga    9660
tgacaggttc ggcctggccc tgtcccatct caacgccatg tccaaggtta aaaggacat    9720 atctgaatgg cagccatcaa aagggtggaa tgattgggaa aatgtgccct tctgttccca    9780
ccacttccat gaactacagc tgaaggatgg caggaggatt gtggtgcctt gccgagaaca    9840
```

```
ggacgagctc attgggagag gaagggtgtc tccaggaaac ggctggatga tcaaggaaac    9900
agcttgcctc agcaaagcct atgccaacat gtggtcactg atgtattttc acaaaaggga    9960
catgaggcta ctgtcattgg ctgtttcctc agctgttccc acctcatggg ttccacaagg   10020
acgcacaaca tggtcgattc atgggaaagg ggagtggatg accacggaag acatgcttga   10080
ggtgtggaac agagtatgga taaccaacaa cccacacatg caggacaaga caatggtgaa   10140
aaaatggaga gatgtccctt atctaaccaa gagacaagac aagctgtgcg atcactgat    10200
tggaatgacc aatagggcca cctgggcctc ccacatccat ttagtcatcc atcgtatccg   10260
aacgctgatt ggacaggaga atacactga ctacctaaca gtcatggaca ggtattctgt    10320
ggatgctgac ctgcaactgg gtgagcttat ctgaaacacc atctaacagg ataaccggg    10380
atacaaacca cgggtggaga accggactcc ccacaacctg aaaccgggat ataaaccacg   10440
gctggagaac cgggctccgc acttaaaatg aaacagaaac cgggataaaa actacggatg   10500
gagaaccgga ctccacacat tgagacagaa gaagttgtca gcccagaacc ccacacgagt   10560
tttgccactg ctaagctgtg aggcagtgca ggctgggaca gccgacctcc aggttgcgaa   10620
aaacctggtt tctgggacct cccaccccag agtaaaaaga acgagcctc cgctaccacc    10680
ctcccacgtg gtggtagaaa gacggggtct agaggttaga ggagaccctc cagggaacaa   10740
atagtgggac catattgacg ccagggaaag accggagtgg ttctctgctt ttcctccaga   10800
ggtctgtgag cacagtttgc tcaagaataa gcagaccttt ggatgacaaa cacaaaacca   10860
ctggccggca tggtcccagc ctcctcgctg gcgccggctg ggcaacattc cgagggggacc  10920
gtcccctcgg taatggcgaa tgggacgaat tctgaaccag tcctaaaacg agtaaatagg   10980
accggcaatt cttcaagcaa taaacaggaa taccaattat aaaagataaa cttagtcaga   11040
tcgtacaata aagctttgaa gaaaaatgcg ccttattcaa tctttgctat aaaaaatggc   11100
ccaaaatctc acattggaag acatttgatg acctcatttc tttcaatgaa gggcctaacg   11160
gagttgacta atgttgtggg aaattggagc gataagcgtg cttctgccgt ggccaggaca   11220
acgtatactc atcagataac agcaatacct gatcactact tcgcactagt ttctcggtac   11280
tatgcatatg atccaatatc aaaggaaatg atagcattga aggatgagac taatccaatt   11340
gaggagtggc agcatataga acagctaaag ggtagtgctg aaggaagcat acgataccccc  11400
gcatggaatg ggataatatc acaggaggta ctagactacc tttcatccta cataaataga   11460
cgcatataag tacgcattta agcataaaca cgcactatgc cgttcttctc atgtatatat   11520
atatacaggc aacacgcaga tataggtgcg acgtgaacag tgagctgtat gtgcgcagct   11580
cgcgttgcat tttcggaagc gctcgttttc ggaaacgctt tgaagttcct attccgaagt   11640
tcctattctc tagaaagtat aggaacttca gagcgctttt gaaaccaaa agcgctctga    11700
agacgcactt tcaaaaaacc aaaaacgcac cggactgtaa cgagctacta aaatattgcg   11760
aataccgctt ccacaaacat tgctcaaaag tatctctttg ctatatatct ctgtgctata   11820
tccctatata acctacccat ccacctttcg ctccttgaac ttgcatctaa actcgacctc   11880
tacattttt atgtttatct ctagtattac tctttagaca aaaaaattgt agtaagaact   11940
attcatagag tgaatcgaaa acaatacgaa aatgtaaaca tttcctatac gtagtatata   12000
gagacaaaat agaagaaacc gttcataatt ttctgaccaa tgaagaatca tcaacgctat   12060
cactttctgt tcacaaagta tgcgcaatcc acatcggtat agaatataat cggggatgcc   12120
tttatcttga aaaaatgcac ccgcagcttc gctagtaatc agtaaacgcg ggaagtggag   12180
```

```
tcaggctttt tttatggaag agaaaataga caccaaagta gccttcttct aaccttaacg    12240
gacctacagt gcaaaaagtt atcaagagac tgcattatag agcgcacaaa ggagaaaaaa    12300
agtaatctaa gatgctttgt tagaaaaata gcgctctcgg gatgcatttt tgtagaacaa    12360
aaaagaagta tagattcttt gttggtaaaa tagcgctctc gcgttgcatt tctgttctgt    12420
aaaaatgcag ctcagattct ttgtttgaaa aattagcgct ctcgcgttgc attttttgttt   12480 tacaaaaatg aagcacagat tcttcgttgg taaaatagcg cttcgcgtt gcatttctgt     12540 tctgtaaaaa tgcagctcag attctttgtt tgaaaaatta gcgctctcgc gttgcatttt   12600
tgttctacaa aatgaagcac agatgcttcg ttaacaaaga tatgctattg aagtgcaaga    12660
tggaaacgca gaaaatgaac cggggatgcg acgtgcaaga ttacctatgc aatagatgca    12720
atagtttctc caggaaccga aatacataca ttgtcttccg taaagcgcta gactatatat    12780
tattatacag gttcaaatat actatctgtt tcagggaaaa ctcccaggtt cggatgttca    12840
aaattcaatg atgggtaaca agtacgatcg taaatctgta aaacagtttg tcggatatta    12900
ggctgtatct cctcaaagcg tattcgaata tcattgagaa gctgcaggca agtgcacaaa    12960
caatacttaa ataaatacta ctcagtaata acctatttct tagcattttt gacgaaattt    13020
gctattttgt tagagtcttt tacaccattt gtctccacac ctccgcttac atcaacacca    13080
ataacgccat ttaatctaag cgcatcacca acattttctg gcgtcagtcc accagctaac    13140
ataaaatgta agctttcggg gctctcttgc cttccaaccc agtcagaaat cgagttccaa    13200
tccaaaagtt cacctgtccc acctgcttct gaatcaaaca agggaataaa cgaatgaggt    13260
ttctgtgaag ctgcactgag tagtatgttg cagtcttttg gaaatacgag tcttttaata    13320
actggcaaac cgaggaactc ttggtattct tgccacgact catctccatg cagttggacg    13380
atatcaatgc cgtaatcatt gaccagagcc aaaacatcct ccttaggttg attacgaaac    13440
acgccaacca agtatttcgg agtgcctgaa ctatttttat atgcttttac aagacttgaa    13500
attttccttg caataaccgg gtcaattgtt ctctttctat tgggcacaca tataataccc    13560
agcaagtcag catcggaatc tagagcacat tctgcggcct ctgtgctctg caagccgcaa    13620
actttcacca atggaccaga actacctgtg aaattaataa cagacatact ccaagctgcc    13680
tttgtgtgct taatcacgta tactcacgtg ctcaatagtc accaatgccc tccctcttgg    13740
ccctcctcct tttcttttttt cgaccgctag cgtcgacagc gacacacttg catcggatgc    13800
agcccggtta acgtgccggc acggcctggg taaccaggta ttttgtccac ataaccgtgc    13860
gcaaaatgtt gtggataagc aggacacagc agcaatccac agcaggcata caaccgcaca    13920
ccgaggttac tccgttctac aggttacgac gacatgtcaa tacttgccct tgacaggcat    13980
tgatggaatc gtagtctcac gctgatagtc tgatcgacaa tacaagtggg accgtggtcc    14040
cagaccgata atcagaccga caacacgagt gggatcgtgg tcccagacta ataatcagac    14100
cgacgatacg agtgggaccg tggtcccaga ctaataatca gaccgacgat acgagtggga    14160
ccgtggttcc agactaataa tcagaccgac gatacgagtg ggaccgtggt cccagactaa    14220
taatcagacc gacgatacga gtgggaccat ggtcccagac taataatcag accgacgata    14280
cgagtgggac cgtggtccca gtctgattat cagaccgacg atacgagtgg gaccgtggtc    14340
ccagactaat aatcagaccg acgatacgag tgggaccgtg gtcccagact aataatcaga    14400
ccgacgatac gagtgggacc gtggtcccag tctgattatc agaccgacga tacaagtgga    14460
acagtgggcc cagagagaat attcaggcca gttatgcttt ctggcctgta acaaaggaca    14520
ttaagtaaag acagataaac gtagactaaa acgtggtcgc atcagggtgc tggcttttca    14580
```

```
agttccttaa gaatggcctc aattttctct atacactcag ttggaacacg ggacctgtcc   14640
aggttaagca ccatttatc gcccttatac aatactgtcg ctccaggagc aaactgatgt    14700
cgtgagctta aactagttct tgatgcagat gacgttttaa gcacagaagt taaaagagtg   14760
ataacttctt cagcttcaaa tatcaccca gcttttttct gctcatgaag gttagatgcc    14820
tgctgcttaa gtaattcctc tttatctgta aaggcttttt gaagtgcatc acctgaccgg   14880
gcagatagtt caccggggtg agaaaaaaga gcaacaactg atttaggcaa tttggcggtg   14940
ttgatacagc gggtaataat cttacgtgaa atattttccg catcagccag cgcagaaata   15000
tttccagcaa attcattctg caatcggctt gcataacgct gaccacgttc ataagcactt   15060
gttgggcgat aatcgttacc caatctggat aatgcagcca tctgctcatc atccagctcg   15120
ccaaccagaa cacgataatc actttcggta agtgcagcag ctttacgacg gcgactccca   15180
tcggcaattt ctatgacacc agatactctt cgaccgaacg ccggtgtctg ttgaccagtc   15240
agtagaaaag aagggatgag atcatccagt gcgtcctcag taagcagctc ctggtcacgt   15300
tcattacctg accatacccg agaggtcttc tcaacactat caccccggag cacttcaaga   15360
gtaaacttca catcccgacc acatacaggc aaagtaatgg cattaccgcg agccattact   15420
cctacgcgcg caattaacga atccaccatc ggggcagctg gtgtcgataa cgaagtatct   15480
tcaaccggtt gagtattgag cgtatgtttt ggaataacag gcgcacgctt cattatctaa   15540
tctcccagcg tggtttaatc agacgatcga aaatttcatt gcagacaggt tcccaaatag   15600
aaagagcatt tctccaggca ccagttgaag agcgttgatc aatggcctgt tcaaaaacag   15660
ttctcatccg gatctgacct ttaccaactt catccgtttc acgtacaaca ttttttagaa   15720
ccatgcttcc ccaggcatcc cgaatttgct cctccatcca cggggactga gagccattac   15780
tattgctgta tttggtaagc aaaatacgta catcaggctc gaacccttta agatcaacgt   15840
tcttgagcag atcacgaagc atatcgaaaa actgcagtgc ggaggtgtag tcaaacaact   15900
cagcaggcgt gggaacaatc agcacatcag cagcacatac gacattaatc gtgccgatac   15960
ccaggttagg cgcgctgtca ataactatga catcatagtc atgagcaaca gtttcaatgg   16020
ccagtcggag catcaggtgt ggatcggtgg gcagtttacc ttcatcaaat ttgcccatta   16080
actcagtttc aatacggtgc agagccagac aggaaggaat aatgtcaagc cccggccagc   16140
aagtgggctt tattgcataa gtgacatcgt ccttttcccc aagatagaaa ggcaggagag   16200
tgtcttctgc atgaatatga agatctggta cccatccgtg atacattgag gctgttccct   16260
gggggtcgtt accttccacg agcaaaacac gtagcccctt cagagccaga tcctgagcaa   16320
gatgaacaga aactgaggtt ttgtaaacgc caccttatg ggcagcaacc ccgatcaccg    16380
gtggaaatac gtcttcagca cgtcgcaatc gcgtaccaaa cacatcacgc atatgattaa   16440
tttgttcaat tgtataacca acacgttgct caacccgtcc tcgaatttcc atatccgggt   16500
gcggtagtcg ccctgctttc tcggcatctc tgatagcctg agaagaaacc ccaactaaat   16560
ccgctgcttc acctattctc cagcgccggg ttattttcct cgcttccggg ctgtcatcat   16620
taaactgtgc aatggcgata gccttcgtca tttcatgacc agcgtttatg cactggttaa   16680
gtgtttccat gagtttcatt ctgaacatcc tttaatcatt gctttgcgtt tttttattaa   16740
atcttgcaat ttactgcaaa gcaacaacaa aatcgcaaag tcatcaaaaa accgcaaagt   16800
tgtttaaaat aagagcaaca ctacaaaagg agataagaag agcacatacc tcagtcactt   16860
attatcacta gcgctcgccg cagccgtgta accgagcata gcgagcgaac tggcgaggaa   16920
```

```
gcaaagaaga actgttctgt cagatagctc ttacgctcag cgcaagaaga aatatccacc    16980
gtgggaaaaa ctccaggtag aggtacacac gcggatagcc aattcagagt aataaactgt    17040
gataatcaac cctcatcaat gatgacgaac taaccccga tatcaggtca catgacgaag     17100
ggaaagagaa ggaaatcaac tgtgacaaac tgccctcaaa tttggcttcc ttaaaaatta    17160
cagttcaaaa agtatgagaa aatccatgca ggctgaagga aacagcaaaa ctgtgacaaa    17220
ttaccctcag taggtcagaa caaatgtgac gaaccaccct caaatctgtg acagataacc    17280
ctcagactat cctgtcgtca tggaagtgat atcgcggaag gaaaatacga tatgagtcgt    17340
ctggcggcct ttcttttct caatgtatga gaggcgcatt ggagttctgc tgttgatctc     17400
attaacacag acctgcagga agcggcggcg gaagtcaggc atacgctggt aactttgagg    17460
cagctggtaa cgctctatga tccagtcgat tttcagagag acgatgcctg agccatccgg    17520
cttacgatac tgacacaggg attcgtataa acgcatggca tacggattgg tgatttcttt    17580
tgtttcacta agccgaaact gcgtaaaccg gttctgtaac ccgataaaga agggaatgag    17640 atatggggttg atatgtacac tgtaaagccc tctggatgga ctgtgcgcac gtttgataaa   17700
ccaaggaaaa gattcatagc ctttttcatc gccggcatcc tcttcagggc gataaaaaac    17760
cacttccttc cccgcgaaac tcttcaatgc ctgccgtata tccttactgg cttccgcaga    17820
ggtcaatccg aatatttcag catatttagc aacatggatc tcgcagatac cgtcatgttc    17880
ctgtagggtg ccatcagatt ttctgatctg gtcaacgaac agatacagca tacgttttg     17940 atcccgggag agactatatg ccgcctcagt gaggtcgttt gactggacga ttcgcgggct    18000 attttacgt ttcttgtgat tgataaccgc tgtttccgcc atgacagatc catgtgaagt     18060
gtgacaagtt tttagattgt cacactaaat aaaaagagt caataagcag ggataacttt     18120
gtgaaaaaac agcttcttct gagggcaatt tgtcacaggg ttaagggcaa tttgtcacag    18180
acaggactgt catttgaggg tgatttgtca cactgaaagg gcaatttgtc acaacacctt    18240
ctctagaacc agcatggata aaggcctaca aggcgctcta aaaagaaga tctaaaaact    18300 ataaaaaaaa taattataaa aatatccccg tggataagtg gataaccca agggaagttt     18360 tttcaggcat cgtgtgtaag cagaatatat aagtgctgtt ccctggtgct tcctcgctca    18420
ctcgaccggg agggttcgag aagggggggc acccccttc ggcgtgcgcg gtcacgcgca     18480
cagggcgcag ccctggttaa aaacaaggtt tataaatatt ggtttaaaag caggttaaaa    18540
gacaggttag cggtggccga aaaacgggcg gaaaccttg caaatgctgg attttctgcc     18600
tgtggacagc ccctcaaatg tcaataggtg cgccctcat ctgtcagcac tctgcccctc     18660
aagtgtcaag gatcgcgccc ctcatctgtc agtagtcgcg cccctcaagt gtcaataccg    18720
cagggcactt atccccaggc ttgtccacat catctgtggg aaactcgcgt aaaatcaggc    18780
gttttcgccg atttgcgagg ctggccagct ccacgtcgcc ggccgaaatc gagcctgccc    18840
ctcatctgtc aacgccgcgc cgggtgagtc ggcccctcaa gtgtcaacgt ccgcccctca    18900
tctgtcagtg agggccaagt tttccgcgag gtatccacaa cgccggcggc cggccgcggt    18960
gtctcgcaca cggcttcgac ggcgtttctg gcgcgtttgc agggccatag acggccgcca    19020
gcccagcggc gagggcaacc agccgagggc ttcgccctgt cgctcgactg cggcgagcac    19080
tactggctgt aaaaggacag accacatcat ggttctgtgt tcattaggtt gttctgtcca    19140
ttgctgacat aatccgctcc acttcaacgt aacaccgcac gaagatttct attgttcctg    19200
aaggcatatt caaatcgttt tcgttaccgc ttgcaggcat catgacagaa cactacttcc    19260
tataaacgct acacaggctc ctgagattaa taatgcggat ctctacgata atgggagatt    19320
```

```
ttcccgactg tttcgttcgc ttctcagtgg ataacagcca gcttctctgt ttaacagaca   19380
aaaacagcat atccactcag ttccacattt ccatataaag gccaaggcat ttattctcag   19440
gataattgtt tcagcatcgc aaccgcatca gactccggca tcgcaaactg cacccggtgc   19500
cgggcagcca catccagcgc aaaaaccttc gtgtagactt ccgttgaact gatggactta   19560
tgtcccatca ggctttgcag aactttcagc ggtataccgg catacagcat gtgcatcgca   19620
taggaatggc ggaacgtatg tggtgtgacc ggaacagaga acgtcacacc gtcagcagca   19680
gcggcggcaa ccgcctcccc aatccaggtc ctgaccgttc tgtccgtcac ttcccagatc   19740
cgcgctttct ctgtccttcc tgtgcgacgg ttacgccgct ccatgagctt atcgcgaata   19800
aatacctgtg acggaagatc acttcgcaga ataaataaat cctggtgtcc ctgttgatac   19860
cgggaagccc tgggccaact tttggcgaaa atgagacgtt gatcggcacg taagaggttc   19920
caactttcac cataatgaaa taagatcact accgggcgta ttttttgagt tatcgagatt   19980
ttcaggagct aaggaagcta aaatggagaa aaaatcact ggatatacca ccgttgatat   20040
atcccaatgg catcgtaaag aacattttga ggcatttcag tcagttgctc aatgtaccta   20100
taaccagacc gttcagctgg atattacggc cttttttaaag accgtaaaga aaataagca   20160 caagttttat ccggccttta ttcacattct tgcccgcctg atgaatgctc atccggaatt   20220
tcgtatggca atgaaagacg gtgagctggt gatatgggat agtgttcacc cttgttacac   20280
cgttttccat gagcaaactg aaacgttttc atcgctctgg agtgaatacc acgacgattt   20340
ccggcagttt ctacacatat attcgcaaga tgtggcgtgt tacggtgaaa acctggccta   20400
tttccctaaa gggtttattg agaatatgtt tttcgtctca gccaatccct gggtgagttt   20460
caccagtttt gatttaaacg tggccaatat ggacaacttc ttcgccccg ttttcaccat   20520 gggcaaatat tatacgcaag cgacaaggt gctgatgccg ctggcgattc aggttcatca   20580
tgccgtttgt gatggcttcc atgtcggcag aatgcttaat gaattacaac agtactgcga   20640
tgagtggcag ggcggggcgt aatttttta aggcagttat tggtgccctt aaacgcctgg   20700
ttgctacgcc tgaataagtg ataataagcg gatgaatggc agaaattcga tgataagctg   20760
tcaaacatga gaattggtcg accctgtgga atgtgtgtca gttagggtgt ggaaagtccc   20820
caggctcccc agcaggcaga gtatgcaaa gcatgcatct caattagtca gcaaccaggt   20880
gtggaaagtc cccaggctcc ccagcaggca gaagtatgca aagcatgcat ctcaattagt   20940
cagcaaccat agtcccgccc ctaactccgc ccatcccgcc cctaactccg cccagttccg   21000
cccattctcc gccccatggc tgactaattt tttttattta tgcagaggcc gaggccgcct   21060
c                                                                   21061
```

<210> SEQ ID NO 5
<211> LENGTH: 21091
<212> TYPE: DNA
<213> ORGANISM: Artificial Sequence
<220> FEATURE:
<223> OTHER INFORMATION: Synthetic construct pShuttle/ChimeriVax-JE

<400> SEQUENCE: 5

```
agtaaatcct gtgtgctaat tgaggtgcat tggtctgcaa atcgagttgc taggcaataa    60
acacatttgg attaatttta atcgttcgtt gagcgattag cagagaactg accagaacat   120
gtctggtcgt aaagctcagg gaaaaaccct gggcgtcaat atggtacgac gaggagttcg   180
ctccttgtca aacaaaataa aacaaaaaac aaaacaaatt ggaaacagac ctggaccttc   240
```

```
aagaggtgtt caaggattta tcttttctt tttgttcaac attttgactg gaaaaaagat    300
cacagcccac ctaaagaggt tgtggaaaat gctggaccca agacaaggct tggctgttct    360
aaggaaagtc aagagagtgg tggccagttt gatgagagga ttgtcctcga ggaaacgccg    420
ttcccatgat gttctgactg tgcaattcct aattttggga atgctgttga tgacgggtgg    480
aatgaagttg tcgaatttcc aggggaagct tttgatgacc atcaacaaca cggacattgc    540
agacgttatc gtgattccca cctcaaaagg agagaacaga tgctgggtcc ggcaatcga     600 cgtcggctac atgtgtgagg acactatcac gtacgaatgt cctaagctta ccatgggcaa    660
tgatccagag gatgtggatt gctggtgtga caaccaagaa gtctacgtcc aatatggacg    720
gtgcacgcgg accaggcatt ccaagcgaag caggagatcc gtgtcggtcc aaacacatgg    780
ggagagttca ctagtgaata aaaaagaggc ttggctggat caacgaaag ccacacgata     840 tctcatgaaa actgagaact ggatcataag gaatcctggc tatgctttcc tggcggcggt    900
acttggctgg atgcttggca gtaacaacgg tcaacgcgtg gtatttacca tcctcctgct    960
gttggtcgct ccggcttaca gttttaattg tctgggaatg ggcaatcgtg acttcataga   1020
aggagccagt ggagccactt gggtggactt ggtgctagaa ggagacagct gcttgacaat   1080
catggcaaac gacaaaccaa cattggacgt ccgcatgatt aacatcgaag ctagccaact   1140
tgctgaggtc agaagttact gctatcatgc ttcagtcact gacatctcga cggtggctcg   1200
gtgccccacg actggagaag cccacaacga gaagcgagct gatagtagct atgtgtgcaa   1260
acaaggcttc actgaccgtg ggtggggcaa cggatgtgga ttttttcggga agggaagcat   1320 tgacacatgt gcaaaattct cctgcaccag taaagcgatt gggagaacaa tccagccaga   1380
aaacatcaaa tacaaagttg gcattttgt gcatggaacc accacttcgg aaaaccatgg     1440
gaattattca gcgcaagttg gggcgtccca ggcggcaaag tttacagtaa cacccaatgc   1500
tccttcggta gccctcaaac ttggtgacta cggagaagtc acactggact gtgagccaag   1560
gagtggactg aacactgaag cgttttacgt catgaccgtg gggtcaaagt catttctggt   1620
ccatagggag tggtttcatg acctcgctct ccctggacg tccccttcga gcacagcgtg    1680
gagaaacaga gaactcctca tggaatttga aggggcgcac gccacaaaac agtccgttgt   1740
tgctcttggg tcacaggaag gaggcctcca tcatgcgttg gcaggagcca tcgtggtgga   1800
gtactcaagc tcagtgatgt taacatcagg ccacctgaaa tgtaggctga aaatggacaa   1860
actggctctg aaaggcacaa cctatggcat gtgtacagaa aaattctcgt tcgcgaaaaa   1920
tccggtggac actggtcacg gaacagttgt cattgaactc tcctactctg ggagtgatgg   1980
cccctgcaaa attccgattg tttccgttgc gagcctcaat gacatgaccc ccgttgggcg   2040
gctggtgaca gtgaacccct tcgtcgcgac ttccagtgcc aactcaaagg tgctggtcga   2100
gatggaaccc cccttcggag actcctacat cgtagttgga aggggagaca agcagatcaa   2160
ccaccattgg cacaaagctg gaagcacgct gggcaaggcc ttttcaacaa ctttgaaggg   2220
agctcaaaga ctgcagcgt tgggcgacac agcctggac tttggctcta ttggagggg     2280 cttcaactcc ataggaagag ccgttcacca agtgtttggt ggtgccttca gaacactctt   2340
tgggggaatg tcttggatca cacaagggct aatgggtgcc ctactgctct ggatgggcgt   2400
caacgcacga gaccgatcaa ttgctttggc cttcttagcc acaggaggtg tgctcgtgtt   2460
cttagcgacc aatgtgggcg ccgatcaagg atgcgccatc aactttggca agagagagct   2520
caagtgcgga gatggtatct tcatatttag agactctgat gactggctga acaagtactc   2580
atactatcca gaagatcctg tgaagcttgc atcaatagtg aaagcctctt ttgaagaagg   2640
```

```
gaagtgtggc ctaaattcag ttgactccct tgagcatgag atgtggagaa gcagggcaga    2700
tgagatcaat gccatttttg aggaaaacga ggtggacatt tctgttgtcg tgcaggatcc    2760
aaagaatgtt taccagagag gaactcatcc attttccaga attcgggatg gtctgcagta    2820
tggttggaag acttggggta agaaccttgt gttctcccca gggaggaaga atggaagctt    2880
catcatagat ggaaagtcca ggaaagaatg cccgttttca aaccgggtct ggaattcttt    2940
ccagatagag gagtttggga cgggagtgtt caccacacgc gtgtacatgg acgcagtctt    3000
tgaatacacc atagactgcg atggatctat cttgggtgca gcggtgaacg gaaaaaagag    3060
tgcccatggc tctccaacat tttggatggg aagtcatgaa gtaaatggga catggatgat    3120
ccacaccttg gaggcattag attacaagga gtgtgagtgg ccactgacac atacgattgg    3180
aacatcagtt gaagagagtg aaatgttcat gccgagatca atcggaggcc agttagctc     3240 tcacaatcat atccctggat acaaggttca gacgaacgga ccttggatgc aggtaccact    3300
agaagtgaag agagaagctt gcccagggac tagcgtgatc attgatggca actgtgatgg    3360
acggggaaaa tcaaccagat ccaccacgga tagcgggaaa gttattcctg aatggtgttg    3420
ccgctcctgc acaatgccgc ctgtgagctt ccatggtagt gatgggtgtt ggtatcccat    3480
ggaaattagg ccaaggaaaa cgcatgaaag ccatctggtg cgctcctggg ttacagctgg    3540
agaaatacat gctgtccctt ttggtttggt gagcatgatg atagcaatgg aagtggtcct    3600
aaggaaaaga cagggaccaa agcaaatgtt ggttggagga gtagtgctct gggagcaat    3660 gctggtcggg caagtaactc tccttgattt gctgaaactc acagtggctg tgggattgca    3720
tttccatgag atgaacaatg gaggagacgc catgtatatg gcgttgattg ctgccttttc    3780
aatcagacca gggctgctca tcggctttgg gctcaggacc ctatggagcc ctcgggaacg    3840
ccttgtgctg accctaggag cagccatggt ggagattgcc ttgggtggcg tgatgggcgg    3900
cctgtggaag tatctaaatg cagtttctct ctgcatcctg acaataaatg ctgttgcttc    3960
taggaaagca tcaaatacca tcttgccct catggctctg ttgacaccgg tcaccatggc    4020
tgaggtgaga cttgccgcaa tgttctttg tgccatggtt atcataggg tccttcacca    4080 gaatttcaag gacacctcca tgcagaagac tatacctctg gtggccctca cactcacatc    4140
ttacctgggc ttgacacaac cttttttggg cctgtgtgca tttctggcaa cccgcatatt    4200
tgggcgaagg agtatcccag tgaatgaggc actcgcagca gctggtctag tgggagtgct    4260
ggcaggactg gcttttcagg agatggagaa cttccttggt ccgattgcag ttggaggact    4320
cctgatgatg ctggttagcg tggctgggag ggtggatggg ctagagctca agaagcttgg    4380
tgaagtttca tgggaagagg aggcggagat cagcgggagt tccgcccgct atgatgtggc    4440
actcagtgaa caaggggagt tcaagctgct ttctgaagag aaagtgccat gggaccaggt    4500
tgtgatgacc tcgctggcct tggttgggc tgccctccat ccatttgctc ttctgctggt    4560
ccttgctggg tggctgtttc atgtcagggg agctaggaga agtggggatg tcttgtggga    4620
tattcccact cctaagatca tcgaggaatg tgaacatctg gaggatggga tttatggcat    4680
attccagtca accttcttgg gggcctccca gcgaggagtg ggagtggcac agggaggggt    4740
gttccacaca atgtggcatg tcacaagagg agctttcctt gtcaggaatg caagaagtt    4800 gattccatct tgggcttcag taaaggaaga ccttgtcgcc tatggtggct catggaagtt    4860
ggaaggcaga tgggatggag aggaagaggt ccagttgatc gcggctgttc caggaaagaa    4920
cgtggtcaac gtccagacaa aaccgagctt gttcaaagtg aggaatgggg gagaaatcgg    4980
```

```
ggctgtcgct cttgactatc cgagtggcac ttcaggatct cctattgtta acaggaacgg      5040
agaggtgatt gggctgtacg gcaatggcat ccttgtcggt gacaactcct tcgtgtccgc      5100
catatcccag actgaggtga aggaagaagg aaaggaggag ctccaagaga tcccgacaat      5160
gctaaagaaa ggaatgacaa ctgtccttga ttttcatcct ggagctggga agacaagacg      5220
tttcctccca cagatcttgg ccgagtgcgc acggagacgc ttgcgcactc ttgtgttggc      5280
ccccaccagg gttgttcttt ctgaaatgaa ggaggctttt cacggcctgg acgtgaaatt      5340
ccacacacag gcttttttccg ctcacggcag cgggagagaa gtcattgatg ccatgtgcca      5400
tgccacccta acttacagga tgttggaacc aactagggtt gttaactggg aagtgatcat      5460
tatggatgaa gcccattttt tggatccagc tagcatagcc gctagaggtt gggcagcgca      5520
cagagctagg gcaaatgaaa gtgcaacaat cttgatgaca gccacaccgc ctgggactag      5580
tgatgaattt ccacattcaa atggtgaaat agaagatgtt caaacggaca tacccagtga      5640
gccctggaac acagggcatg actggatcct agctgacaaa aggcccacgg catggttcct      5700
tccatccatc agagctgcaa atgtcatggc tgcctctttg cgtaaggctg aaagagtgt       5760 ggtggtcctg aacaggaaaa cctttgagag agaatacccc acgataaagc agaagaaacc      5820
tgactttata ttggccactg acatagctga atgggagcc aacctttgcg tggagcgagt      5880
gctggattgc aggacggctt ttaagcctgt gcttgtggat aagggagga aggtggcaat      5940 aaaagggcca cttcgtatct ccgcatcctc tgctgctcaa aggaggggc gcattgggag      6000 aaatcccaac agagatggag actcatacta ctattctgag cctacaagtg aaaataatgc      6060
ccaccacgtc tgctggttgg aggcctcaat gctcttggac aacatggagg tgaggggtgg      6120
aatggtcgcc ccactctatg gcgttgaagg aactaaaaca ccagtttccc ctggtgaaat      6180
gagactgagg gatgaccaga ggaaagtctt cagagaacta gtgaggaatt gtgacctgcc      6240
cgtttggctt tcgtggcaag tggccaaggc tggtttgaag acgaatgatc gtaagtggtg      6300
ttttgaaggc cctgaggaac atgagatctt gaatgacagc ggtgaaacag tgaagtgcag      6360
ggctcctgga ggagcaaaga agcctctgcg cccaaggtgg tgtgatgaaa gggtgtcatc      6420
tgaccagagt gcgctgtctg aatttattaa gtttgctgaa ggtaggaggg gagctgctga      6480
agtgctagtt gtgctgagtg aactccctga tttcctggct aaaaaaggtg gagaggcaat      6540
ggataccatc agtgtgttcc tccactctga ggaaggctct agggcttacc gcaatgcact      6600
atcaatgatg cctgaggcaa tgacaatagt catgctgttt atactggctg gactactgac      6660
atcgggaatg gtcatctttt tcatgtctcc caaaggcatc agtagaatgt ctatggcgat      6720
gggcacaatg gccggctgtg gatatctcat gttccttgga ggcgtcaaac ccactcacat      6780
ctcctatgtc atgctcatat tctttgtcct gatggtggtt gtgatccccg agccagggca      6840
acaaaggtcc atccaagaca accaagtggc atacctcatt attggcatcc tgacgctggt      6900
ttcagcggtg gcagccaacg agctaggcat gctggagaaa accaagagg acctctttgg      6960 gaagaagaac ttaattccat ctagtgcttc accctggagt tggccggatc ttgacctgaa      7020
gccaggagct gcctggacag tgtacgttgg cattgttaca atgctctctc caatgttgca      7080
ccactggatc aaagtcgaat atggcaacct gtctctgtct ggaatagccc agtcagcctc      7140
agtcctttct ttcatggaca agggatacc attcatgaag atgaatatct cggtcataat      7200
gctgctggtc agtggctgga attcaataac agtgatgcct ctgctctgtg cataggggtg      7260
cgccatgctc cactggtctc tcattttacc tggaatcaaa gcgcagcagt caaagctagc      7320
acagagaagg gtgttccatg gcgttgccga gaaccctgtg gttgatggga atccaacagt      7380
```

```
tgacattgag gaagctcctg aaatgcctgc cctttatgag aagaaactgg ctctatatct   7440
ccttcttgct ctcagcctag cttctgttgc catgtgcaga acgccctttt cattggctga   7500
aggcattgtc ctagcatcag ctgccttagg gccgctcata gagggaaaca ccagccttct   7560
ttggaatgga cccatggctg tctccatgac aggagtcatg aggggaatc actatgcttt    7620 tgtgggagtc atgtacaatc tatggaagat gaaaactgga cgccggggga gcgcgaatgg   7680
aaaaactttg ggtgaagtct ggaagaggga actgaatctg ttggacaagc gacagtttga   7740
gttgtataaa aggaccgaca ttgtggaggt ggatcgtgat acggcacgca ggcatttggc   7800
cgaagggaag gtggacaccg gggtggcggt ctccaggggg accgcaaagt taaggtggtt   7860
ccatgagcgt ggctatgtca agctggaagg tagggtgatt gacctggggt gtggccgcgg   7920
aggctggtgt tactacgctg ctgcgcaaaa ggaagtgagt ggggtcaaag gatttactct   7980
tggaagagac ggccatgaga aacccatgaa tgtgcaaagt ctgggatgga acatcatcac   8040
cttcaaggac aaaactgata tccaccgcct agaaccagtg aaatgtgaca ccctttttgtg  8100 tgacattgga gagtcatcat cgtcatcggt cacagagggg gaaaggaccg tgagagttct   8160
tgatactgta gaaaaatggc tggcttgtgg ggttgacaac ttctgtgtga aggtgttagc   8220
tccatacatg ccagatgttc ttgagaaact ggaattgctc caaggaggt ttggcggaac    8280 agtgatcagg aaccctctct ccaggaattc cactcatgaa atgtactacg tgtctggagc   8340
ccgcagcaat gtcacattta ctgtgaacca acatcccgc ctcctgatga ggagaatgag    8400
gcgtccaact ggaaaagtga ccctggaggc tgacgtcatc ctcccaattg ggacacgcag   8460
tgttgagaca gacaagggac ccctggacaa agaggccata aagaaaggg ttgagaggat    8520 aaaatctgag tacatgacct cttggttttta tgacaatgac aaccctaca ggacctggca   8580 ctactgtggc tcctatgtca caaaaacctc aggaagtgcg gcgagcatgg taaatggtgt   8640
tattaaaatt ctgacatatc catgggacag gatagaggag gtcacaagaa tggcaatgac   8700
tgacacaacc ccttttggac agcaaagagt gttttaaagaa aaagttgaca ccagagcaaa   8760
ggatccacca gcgggaacta ggaagatcat gaaagttgtc aacaggtggc tgttccgcca   8820
cctggccaga gaaaagaacc ccagactgtg cacaaaggaa gaatttattg caaaagtccg   8880
aagtcatgca gccattggag cttacctgga agaacaagaa cagtggaaga ctgccaatga   8940
ggctgtccaa gacccaaagt ctgggaact ggtggatgaa gaaaggaagc tgcaccaaca    9000
aggcaggtgt cggacttgtg tgtacaacat gatgggaaaa agagagaaga agctgtcaga   9060
gtttgggaaa gcaagggaa gccgtgccat atggtatatg tggctgggag cgcggtatct    9120
tgagtttgag gccctgggat tcctgaatga ggaccattgg gcttccaggg aaaactcagg   9180
aggaggagtg gaaggcattg gcttacaata cctaggatat gtgatcagag acctggctgc   9240
aatggatggt ggtggtggattct acgcggatga caccgctgga tgggacacgc gcatcacaga   9300
ggcagaccct tgatgatgaac aggagatctt gaactacatg agcccacatc acaaaaaact   9360
ggcacaagca gtgatggaaa tgacatacaa gaacaaagtg gtgaaagtgt tgagaccagc   9420
cccaggaggg aaagcctaca tggatgtcat aagtcgacga gaccagagag gatccgggca   9480
ggtagtgact tatgctctga acaccatcac caacttgaaa gtccaattga tcagaatggc   9540
agaagcagag atggtgatac atcaccaaca tgttcaagat tgtgatgaat cagttctgac   9600
caggctggag gcatggctca ctgagcacgg atgtgacaga ctgaagagga tggcggtgag   9660
tggagacgac tgtgtggtcc ggcccatcga tgacaggttc ggcctggccc tgtcccatct   9720
```

```
caacgccatg tccaaggtta gaaaggacat atctgaatgg cagccatcaa aagggtggaa      9780
tgattgggag aatgtgccct tctgttccca ccacttccat gaactacagc tgaaggatgg      9840
caggaggatt gtggtgcctt gccgagaaca ggacgagctc attgggagag aagggtgtc      9900 tccaggaaac ggctggatga tcaaggaaac agcttgcctc agcaaagcct atgccaacat      9960
gtggtcactg atgtattttc acaaaaggga catgaggcta ctgtcattgg ctgtttcctc     10020
agctgttccc acctcatggg ttccacaagg acgcacaaca tggtcgattc atgggaaagg     10080
ggagtggatg accacggaag acatgcttga ggtgtggaac agagtatgga taaccaacaa     10140
cccacacatg caggacaaga caatggtgaa aaaatggaga gatgtcccct atctaaccaa     10200
gagacaagac aagctgtgcg gatcactgat tggaatgacc aatagggcca cctgggcctc     10260
ccacatccat ttagtcatcc atcgtatccg aacgctgatt ggacaggaga atacactga     10320 ctacctaaca gtcatggaca ggtattctgt ggatgctgac ctgcaactgg gtgagcttat     10380
ctgaaacacc atctaacagg aataaccggg atacaaacca cgggtggaga accggactcc     10440
ccacaacctg aaaccgggat ataaaccacg gctggagaac cgggctccgc acttaaaatg     10500
aaacagaaac cgggataaaa actacggatg gagaaccgga ctccacacat tgagacagaa     10560
gaagttgtca gcccagaacc ccacgagt tttgccactg ctaagctgtg aggcagtgca     10620
ggctgggaca gccgacctcc aggttgcgaa aaacctggtt tctgggacct cccaccccag     10680
agtaaaaaga acgagcctc cgctaccacc ctcccacgtg gtggtagaaa gacggggtct     10740
agaggttaga ggagaccctc cagggaacaa atagtgggac catattgacg ccagggaaag     10800
accggagtgg ttctctgctt ttcctccaga ggtctgtgag cacagtttgc tcaagaataa     10860
gcagaccttt ggatgacaaa cacaaaacca ctggccggca tggtcccagc ctcctcgctg     10920
gcgccggctg ggcaacattc cgaggggacc gtccctcgg taatggcgaa tgggacgaat     10980
tctgaaccag tcctaaaacg agtaaatagg accggcaatt cttcaagcaa taaacaggaa     11040
taccaattat taaagataa cttagtcaga tcgtacaata aagctttgaa gaaaaatgcg     11100
ccttattcaa tctttgctat aaaaaatggc ccaaaatctc acattggaag acatttgatg     11160
acctcatttc tttcaatgaa gggcctaacg gagttgacta atgttgtggg aaattggagc     11220
gataagcgtg cttctgccgt ggccaggaca acgtatactc atcagataac agcaataccct    11280 gatcactact tcgcactagt ttctcggtac tatgcatatg atccaatatc aaaggaaatg     11340
atagcattga aggatgagac taatccaatt gaggagtggc agcatataga acagctaaag     11400
ggtagtgctg aaggaagcat acgataccc gcatggaatg ggataatatc acaggaggta     11460
ctagactacc tttcatccta cataaataga cgcatataag tacgcattta agcataaaca     11520
cgcactatgc cgttcttctc atgtatatat atatacaggc aacacgcaga tataggtgcg     11580
acgtgaacag tgagctgtat gtgcgcagct cgcgttgcat tttcggaagc gctcgttttc     11640
ggaaacgctt tgaagttcct attccgaagt tcctattctc tagaaagtat aggaacttca     11700
gagcgctttt gaaaaccaaa agcgctctga agacgcactt tcaaaaaacc aaaaacgcac     11760
cggactgtaa cgagctacta aaatattgcg aataccgctt ccacaaacat tgctcaaaag     11820
tatctctttg ctatatatct ctgtgctata tccctatata acctaccat ccacctttcg     11880 ctccttgaac ttgcatctaa actcgacctc tacatttttt atgtttatct ctagtattac     11940
tctttagaca aaaaaattgt agtaagaact attcatagag tgaatcgaaa acaatacgaa     12000
aatgtaaaca tttcctatac gtagtatata gagacaaaat agaagaaacc gttcataatt     12060
ttctgaccaa tgaagaatca tcaacgctat cactttctgt tcacaaagta tgcgcaatcc     12120
```

```
acatcggtat agaatataat cggggatgcc tttatcttga aaaaatgcac ccgcagcttc    12180
gctagtaatc agtaaacgcg ggaagtggag tcaggctttt tttatggaag agaaaataga    12240
caccaaagta gccttcttct aaccttaacg gacctacagt gcaaaaagtt atcaagagac    12300
tgcattatag agcgcacaaa ggagaaaaaa agtaatctaa gatgctttgt tagaaaaata    12360
gcgctctcgg gatgcatttt tgtagaacaa aaagaagta tagattcttt gttggtaaaa    12420
tagcgctctc gcgttgcatt tctgttctgt aaaaatgcag ctcagattct ttgtttgaaa    12480
aattagcgct ctcgcgttgc attttgttt tacaaaaatg aagcacagat tcttcgttgg    12540
taaaatagcg ctttcgcgtt gcatttctgt tctgtaaaaa tgcagctcag attctttgtt    12600
tgaaaaatta gcgctctcgc gttgcatttt tgttctacaa aatgaagcac agatgcttcg    12660
ttaacaaaga tatgctattg aagtgcaaga tggaaacgca gaaaatgaac cggggatgcg    12720
acgtgcaaga ttacctatgc aatagatgca atagtttctc caggaaccga aatacataca    12780
ttgtcttccg taaagcgcta gactatatat tattatacag gttcaaatat actatctgtt    12840
tcagggaaaa ctcccaggtt cggatgttca aaattcaatg atgggtaaca agtacgatcg    12900
taaatctgta aaacagtttg tcggatatta ggctgtatct cctcaaagcg tattcgaata    12960
tcattgagaa gctgcaggca agtgcacaaa caatacttaa ataaatacta ctcagtaata    13020
acctatttct tagcattttt gacgaaattt gctattttgt tagagtcttt tacaccattt    13080
gtctccacac ctccgcttac atcaacacca ataacgccat ttaatctaag cgcatcacca    13140
acattttctg gcgtcagtcc accagctaac ataaaatgta agctttcggg gctctcttgc    13200
cttcaacccc agtcagaaat cgagttccaa tccaaaagtt cacctgtccc acctgcttct    13260
gaatcaaaca agggaataaa cgaatgaggt ttctgtgaag ctgcactgag tagtatgttg    13320
cagtcttttg gaaatacgag tctttttaata actggcaaac cgaggaactc ttggtattct    13380
tgccacgact catctccatg cagttggacg atatcaatgc cgtaatcatt gaccagagcc    13440
aaaacatcct ccttaggttg attacgaaac acgccaacca agtatttcgg agtgcctgaa    13500 ctattttat atgcttttac aagacttgaa attttccttg caataaccgg gtcaattgtt    13560
ctctttctat tgggcacaca tataatacc agcaagtcag catcggaatc tagagcacat    13620
tctgcggcct ctgtgctctg caagccgcaa actttcacca atggaccaga actacctgtg    13680
aaattaataa cagacatact ccaagctgcc tttgtgtgct taatcacgta tactcacgtg    13740
ctcaatagtc accaatgccc tccctcttgg ccctcctcct tttcttttt cgaccgctag    13800 cgtcgacagc gacacacttg catcggatgc agcccggtta acgtgccggc acggcctggg    13860
taaccaggta ttttgtccac ataaccgtgc gcaaaatgtt gtggataagc aggacacagc    13920
agcaatccac agcaggcata caaccgcaca ccgaggttac tccgttctac aggttacgac    13980
gacatgtcaa tacttgccct tgacaggcat tgatggaatc gtagtctcac gctgatagtc    14040
tgatcgacaa tacaagtggg accgtggtcc cagaccgata atcagaccga caacacgagt    14100
gggatcgtgg tcccagacta ataatcagac cgacgatacg agtgggaccg tggtcccaga    14160
ctaataatca gaccgacgat acgagtggga ccgtggttcc agactaataa tcagaccgac    14220
gatacgagtg ggaccgtggt cccagactaa taatcagacc gacgatacga gtgggaccat    14280
ggtcccagac taataatcag accgacgata cgagtgggac cgtggtccca gtctgattat    14340
cagaccgacg atacgagtgg gaccgtggtc ccagactaat aatcagaccg acgatacgag    14400
tgggaccgtg gtcccagact aataatcaga ccgacgatac gagtgggacc gtggtcccag    14460
```

```
tctgattatc agaccgacga tacaagtgga acagtgggcc cagagagaat attcaggcca    14520
gttatgcttt ctggcctgta acaaaggaca ttaagtaaag acagataaac gtagactaaa    14580
acgtggtcgc atcagggtgc tggcttttca agttccttaa gaatggcctc aattttctct    14640
atacactcag ttggaacacg ggacctgtcc aggttaagca ccattttatc gcccttatac    14700
aatactgtcg ctccaggagc aaactgatgt cgtgagctta aactagttct tgatgcagat    14760
gacgttttaa gcacagaagt taaaagagtg ataacttctt cagcttcaaa tatcacccca    14820
gcttttttct gctcatgaag gttagatgcc tgctgcttaa gtaattcctc tttatctgta    14880
aaggcttttt gaagtgcatc acctgaccgg gcagatagtt caccggggtg agaaaaaaga    14940
gcaacaactg atttaggcaa tttggcggtg ttgatacagc gggtaataat cttacgtgaa    15000
atattttccg catcgccag cgcagaaata tttccagcaa attcattctg caatcggctt     15060
gcataacgct gaccacgttc ataagcactt gttgggcgat aatcgttacc caatctggat    15120
aatgcagcca tctgctcatc atccagctcg ccaaccagaa cacgataatc actttcggta    15180
agtgcagcag ctttacgacg gcgactccca tcggcaattt ctatgacacc agatactctt    15240
cgaccgaacg ccggtgtctg ttgaccagtc agtagaaaag aagggatgag atcatccagt    15300
gcgtcctcag taagcagctc ctggtcacgt tcattacctg accatacccg agaggtcttc    15360
tcaacactat cacccggag cacttcaaga gtaaacttca catcccgacc acatacaggc    15420
aaagtaatgg cattaccgcg agccattact cctacgcgcg caattaacga atccaccatc    15480
ggggcagctg gtgtcgataa cgaagtatct tcaaccggtt gagtattgag cgtatgtttt    15540 ggataacag gcgcacgctt cattatctaa tctcccagcg tggtttaatc agacgatcga     15600
aaatttcatt gcagacaggt tcccaaatag aaagagcatt tctccaggca ccagttgaag    15660
agcgttgatc aatggcctgt tcaaaaacag ttctcatccg gatctgacct ttaccaactt    15720
catccgtttc acgtacaaca tttttttagaa ccatgcttcc ccaggcatcc cgaatttgct    15780
cctccatcca cggggactga gagccattac tattgctgta tttggtaagc aaaatacgta    15840
catcaggctc gaacccttta agatcaacgt tcttgagcag atcacgaagc atatcgaaaa    15900
actgcagtgc ggaggtgtag tcaaacaact cagcaggcgt gggaacaatc agcacatcag    15960
cagcacatac gacattaatc gtgccgatac ccaggttagg cgcgctgtca ataactatga    16020
catcatagtc atgagcaaca gtttcaatgg ccagtcggag catcaggtgt ggatcggtgg    16080
gcagtttacc ttcatcaaat ttgcccatta actcagtttc aatacggtgc agagccagac    16140
aggaaggaat aatgtcaagc cccggccagc aagtgggctt tattgcataa gtgacatcgt    16200 cctttttcccc aagatagaaa ggcaggagag tgtcttctgc atgaatatga agatctggta    16260
cccatccgtg atacattgag gctgttccct gggggtcgtt accttccacg agcaaaacac    16320
gtagccccct cagagccaga tcctgagcaa gatgaacaga aactgaggtt ttgtaaacgc    16380 caccttatg ggcagcaacc ccgatcaccg gtggaaatac gtcttcagca cgtcgcaatc     16440
gcgtaccaaa cacatcacgc atatgattaa tttgttcaat tgtataacca acacgttgct    16500
caacccgtcc tcgaatttcc atatccgggt gcggtagtcg ccctgctttc tcggcatctc    16560
tgatagcctg agaagaaacc ccaactaaat ccgctgcttc acctattctc cagcgccggg    16620 ttatttttcct cgcttccggg ctgtcatcat taaactgtgc aatggcgata gccttcgtca    16680
tttcatgacc agcgtttatg cactggttaa gtgtttccat gagtttcatt ctgaacatcc    16740
tttaatcatt gctttgcgtt ttttttattaa atcttgcaat ttactgcaaa gcaacaacaa    16800
aatcgcaaag tcatcaaaaaa accgcaaagt tgtttaaaat aagagcaaca ctacaaaagg    16860
```

```
agataagaag agcacatacc tcagtcactt attatcacta gcgctcgccg cagccgtgta   16920
accgagcata gcgagcgaac tggcgaggaa gcaaagaaga actgttctgt cagatagctc   16980
ttacgctcag cgcaagaaga aatatccacc gtgggaaaaa ctccaggtag aggtacacac   17040
gcggatagcc aattcagagt aataaactgt gataatcaac cctcatcaat gatgacgaac   17100 taaccccga tatcaggtca catgacgaag ggaagagaa ggaaatcaac tgtgacaaac   17160
tgccctcaaa tttggcttcc ttaaaaatta cagttcaaaa agtatgagaa aatccatgca   17220
ggctgaagga aacagcaaaa ctgtgacaaa ttaccctcag taggtcagaa caaatgtgac   17280
gaaccaccct caaatctgtg acagataacc ctcagactat cctgtcgtca tggaagtgat   17340
atcgcggaag gaaaatacga tatgagtcgt ctggcggcct ttcttttct caatgtatga   17400 gaggcgcatt ggagttctgc tgttgatctc attaacacag acctgcagga agcggcggcg   17460
gaagtcaggc atacgctggt aactttgagg cagctggtaa cgctctatga tccagtcgat   17520
tttcagagag acgatgcctg agccatccgg cttacgatac tgacacaggg attcgtataa   17580
acgcatggca tacggattgg tgatttcttt tgtttcacta agccgaaact gcgtaaaccg   17640
gttctgtaac ccgataaaga agggaatgag atatgggttg atatgtacac tgtaaagccc   17700
tctggatgga ctgtgcgcac gtttgataaa ccaaggaaaa gattcatagc cttttcatc   17760 gccggcatcc tcttcagggc gataaaaaac cacttccttc cccgcgaaac tcttcaatgc   17820
ctgccgtata tccttactgg cttccgcaga ggtcaatccg aatatttcag catatttagc   17880
aacatggatc tcgcagatac cgtcatgttc ctgtagggtg ccatcagatt ttctgatctg   17940
gtcaacgaac agatacagca tacgtttttg atcccgggag agactatatg ccgcctcagt   18000
gaggtcgttt gactggacga ttcgcgggct attttacgt ttcttgtgat tgataaccgc   18060
tgtttccgcc atgacagatc catgtgaagt gtgacaagtt tttagattgt cacactaaat   18120 aaaaagagt caataagcag ggataacttt gtgaaaaac agcttcttct gagggcaatt   18180
tgtcacaggg ttaagggcaa tttgtcacag acaggactgt catttgaggg tgatttgtca   18240
cactgaaagg gcaatttgtc acaacaccct ctctagaacc agcatggata aaggcctaca   18300
aggcgctcta aaaagaaga tctaaaaact ataaaaaaa taattataaa aatatccccg   18360
tggataagtg gataaccca agggaagttt tttcaggcat cgtgtgtaag cagaatatat   18420
aagtgctgtt ccctggtgct tcctcgctca ctcgaccggg agggtcgag aaggggggc   18480 acccccttc ggcgtgcgcg gtcacgcgca cagggcgcag ccctggttaa aaacaaggtt   18540
tataaatatt ggtttaaaag caggttaaaa gacaggttag cggtggccga aaacgggcg   18600 gaaacccttg caaatgctgg attttctgcc tgtggacagc ccctcaaatg tcaataggtg   18660
cgcccctcat ctgtcagcac tctgccctc aagtgtcaag gatcgcgccc ctcatctgtc   18720
agtagtcgcg cccctcaagt gtcaataccg cagggcactt atccccaggc ttgtccacat   18780
catctgtggg aaactcgcgt aaaatcaggc gttttcgccg atttgcgagg ctggccagct   18840
ccacgtcgcc ggccgaaatc gagcctgccc ctcatctgtc aacgccgcgc cgggtgagtc   18900
ggcccctcaa gtgtcaacgt ccgccctca tctgtcagtg agggccaagt tttccgcgag   18960
gtatccacaa cgccggcggc cggccgcggt gtctcgcaca cggcttcgac ggcgtttctg   19020
gcgcgtttgc agggccatag acggccgcca gcccagcggc gagggcaacc agccgagggc   19080
ttcgccctgt cgctcgactg cggcgagcac tactggctgt aaaaggacag accacatcat   19140
ggttctgtgt tcattaggtt gttctgtcca ttgctgacat aatccgctcc acttcaacgt   19200
```

| | |
|---|---|
| aacaccgcac gaagatttct attgttcctg aaggcatatt caaatcgttt tcgttaccgc | 19260 |
| ttgcaggcat catgacagaa cactacttcc tataaacgct acacaggctc ctgagattaa | 19320 |
| taatgcggat ctctacgata tgggagatt ttcccgactg tttcgttcgc ttctcagtgg | 19380 |
| ataacagcca gcttctctgt ttaacagaca aaaacagcat atccactcag ttccacattt | 19440 |
| ccatataaag gccaaggcat ttattctcag gataattgtt tcagcatcgc aaccgcatca | 19500 |
| gactccggca tcgcaaactg cacccggtgc cgggcagcca catccagcgc aaaaaccttc | 19560 |
| gtgtagactt ccgttgaact gatggactta tgtcccatca ggctttgcag aactttcagc | 19620 |
| ggtataccgg catacagcat gtgcatcgca taggaatggc ggaacgtatg tggtgtgacc | 19680 |
| ggaacagaga acgtcacacc gtcagcagca gcggcggcaa ccgcctcccc aatccaggtc | 19740 |
| ctgaccgttc tgtccgtcac ttcccagatc cgcgctttct ctgtccttcc tgtgcgacgg | 19800 |
| ttacgccgct ccatgagctt atcgcgaata aatacctgtg acggaagatc acttcgcaga | 19860 |
| ataaataaat cctggtgtcc ctgttgatac cgggaagccc tgggccaact tttggcgaaa | 19920 |
| atgagacgtt gatcggcacg taagaggttc aactttcac cataatgaaa taagatcact | 19980 |
| accgggcgta ttttttgagt tatcgagatt tcaggagct aaggaagcta aaatggagaa | 20040 |
| aaaaatcact ggatatacca ccgttgatat atcccaatgg catcgtaaag aacatttga | 20100 |
| ggcatttcag tcagttgctc aatgtaccta taaccagacc gttcagctgg atattacggc | 20160 |
| cttttttaaag accgtaaaga aaaataagca caagttttat ccggccttta ttcacattct | 20220 |
| tgcccgcctg atgaatgctc atccggaatt tcgtatggca atgaaagacg gtgagctggt | 20280 |
| gatatgggat agtgttcacc cttgttacac cgttttccat gagcaaactg aaacgttttc | 20340 |
| atcgctctgg agtgaatacc acgacgattt ccggcagttt ctacacatat attcgcaaga | 20400 |
| tgtggcgtgt tacggtgaaa acctggccta tttccctaaa gggtttattg agaatatgtt | 20460 |
| tttcgtctca gccaatccct gggtgagttt caccagtttt gatttaaacg tggccaatat | 20520 |
| ggacaacttc ttcgccccg ttttcaccat gggcaaatat tatacgcaag gcgacaaggt | 20580 |
| gctgatgccg ctggcgattc aggttcatca tgccgtttgt gatggcttcc atgtcggcag | 20640 |
| aatgcttaat gaattacaac agtactgcga tgagtggcag gcgggggcgt aattttttta | 20700 |
| aggcagttat tggtgccctt aaacgcctgg ttgctacgcc tgaataagtg ataataagcg | 20760 |
| gatgaatggc agaaattcga tgataagctg tcaaacatga gaattggtcg accctgtgga | 20820 |
| atgtgtgtca gttagggtgt ggaaagtccc caggctcccc agcaggcaga agtatgcaaa | 20880 |
| gcatgcatct caattagtca gcaaccaggt gtggaaagtc cccaggctcc ccagcaggca | 20940 |
| gaagtatgca aagcatgcat ctcaattagt cagcaaccat agtcccgccc ctaactccgc | 21000 |
| ccatcccgcc cctaactccg cccagttccg cccattctcc gccccatggc tgactaattt | 21060 |
| tttttattta tgcagaggcc gaggccgcct c | 21091 |

<210> SEQ ID NO 6
<211> LENGTH: 21094
<212> TYPE: DNA
<213> ORGANISM: Artificial Sequence
<220> FEATURE:
<223> OTHER INFORMATION: Synthetic construct pShuttle/ChimeriVax-WN

<400> SEQUENCE: 6

| | |
|---|---|
| agtaaatcct gtgtgctaat tgaggtgcat tggtctgcaa atcgagttgc taggcaataa | 60 |
| acacatttgg attaattta atcgttcgtt gagcgattag cagagaactg accagaacat | 120 |
| gtctggtcgt aaagctcagg gaaaaaccct gggcgtcaat atggtacgac gaggagttcg | 180 |

```
ctccttgtca aacaaaataa aacaaaaaac aaaacaaatt ggaaacagac ctggaccttc      240
aagaggtgtt caaggattta tcttttctt tttgttcaac attttgactg gaaaaaagat       300
cacagcccac ctaaagaggt tgtggaaaat gctggaccca agacaaggct tggctgttct      360
aaggaaagtc aagagagtgg tggccagttt gatgagagga ttgtcctcga ggaaacgccg      420
ttcccatgat gttctgactg tgcaattcct aattttggga atgctgttga tgacgggtgg     480
agttaccctc tctaacttcc aagggaaggt gatgatgacg gtaaatgcta ctgacgtcac      540
agatgtcatc acgattccaa cagctgctgg aaagaaccta tgcattgtca gagcaatgga     600
tgtgggatac atgtgcgatg atactatcac ttatgaatgc ccagtgctgt cggctggtaa     660
tgatccagaa gacatcgact gttggtgcac aaagtcagca gtctacgtca ggtatggaag     720
atgcaccaag acacgccact caagacgcag tcggaggtca ctgacagtgc agacacacgg     780
agaaagcact ctagcgaaca agaaggggc ttggatggac agcaccaagg ccacaaggta      840
tttggtaaaa acagaatcat ggatcttgag gaaccctgga tatgccctgg tggcagccgt     900
cattggttgg atgcttggga gcaacaccat gcagagagtt gtgtttgtcg tgctattgct     960
tttggtggcc ccagcttaca gcttcaactg ccttggaatg agcaacagag acttcttgga    1020
aggagtgtct ggagcaacat gggtggattt ggttctcgaa ggcgacagct gcgtgactat    1080
catgtctaag gacaagccta ccatcgatgt gaagatgatg aatatggagg cggccaacct    1140
ggcagaggtc cgcagttatt gctatttggc taccgtcagc gatctctcca ccaaagctgc    1200
gtgcccgacc atgggagaag ctcacaatga caaacgtgct gacccagctt ttgtgtgcag    1260
acaaggagtg gtgacaggg gctggggcaa cggctgcgga ttctttggaa aaggatccat     1320
tgacacatgc gccaaatttg cctgctctac caaggcaata ggaagaacca tcttgaaaga    1380
gaatatcaag tacgaagtgg ccattttgt ccatggacca actactgtgg agtcgcacgg     1440
aaactactcc acacaggttg gagccactca ggcaggagaa ttcagcatca ctcctgcggc    1500
gccttcatac acactaaagc ttggagaata tggagaggtg acagtggact gtgaaccacg    1560 gtcaggggatt gacaccaatg catactacgt gatgactgtt ggaacaaaga cgttcttggt    1620
ccatcgtgag tggttcatgg acctcaacct cccttggagc agtgctggaa gtactgtgtg    1680
gaggaacaga gagacgttaa tggagtttga ggaaccacac gccacgaagc agtctgtgat    1740
agcattgggc tcaaagagg gagctctgca tcaagctttg gctggagcca ttcctgtgga    1800
attttcaagc aacactgtca agttgacgtc gggtcatttg aagtgtagag tgaagatgga    1860
aaaattgcag ttgaagggaa caacctatgg cgtctgttca aaggcttca agtttcttgg      1920 gactcccgtc gacacaggtc acggcactgt ggtgttggaa ttgcagtaca ctggcacgga    1980
tggaccttgc aaagttccta tctcgtcagt ggcttcattg aacgacctaa cgccagtggg    2040
cagattggtc actgtcaacc ctttttgtttc agtggccacg ccaacgcta aggtcctgat    2100 tgaattggaa ccacccttg gagactcata catagtggtg ggcagaggag aacaacagat    2160
caatcaccat tggcacaagt ctggaagcag cattggcaaa gcctttacaa ccaccctcaa    2220
aggagcgcag agactagccg ctctaggaga cacagcttgg gactttggat cagttggagg    2280
ggtgttcacc tcagttgggc gcgctgtcca tcaagtgttc ggaggagcat tccgctcact    2340
gttcggaggc atgtcctgga taacgcaagg attgctgggg gctctcctgt tgtggatggg    2400
catcaatgct cgtgataggt ccatagctct cacgtttctc gcagttggag gagttctgct    2460
cttcctctcc gtgaacgtgg gcgccgatca aggatgcgcc atcaactttg gcaagagaga    2520
```

```
gctcaagtgc ggagatggta tcttcatatt tagagactct gatgactggc tgaacaagta    2580
ctcatactat ccagaagatc ctgtgaagct tgcatcaata gtgaaagcct cttttgaaga    2640
agggaagtgt ggcctaaatt cagttgactc ccttgagcat gagatgtgga gaagcagggc    2700
agatgagatc aatgccattt ttgaggaaaa cgaggtggac atttctgttg tcgtgcagga    2760
tccaaagaat gtttaccaga gaggaactca tccatttttcc agaattcggg atggtctgca    2820
gtatggttgg aagacttggg gtaagaacct tgtgttctcc ccagggagga agaatggaag    2880
cttcatcata gatggaaagt ccaggaaaga atgcccgttt tcaaaccggg tctggaattc    2940
tttccagata gaggagtttg ggacgggagt gttcaccaca cgcgtgtaca tggacgcagt    3000
cttttgaatac accatagact gcgatggatc tatcttgggt gcagcggtga acggaaaaaa    3060
gagtgcccat ggctctccaa cattttggat gggaagtcat gaagtaaatg ggacatggat    3120
gatccacacc ttggaggcat tagattacaa ggagtgtgag tggccactga cacatacgat    3180
tggaacatca gttgaagaga gtgaaatgtt catgccgaga tcaatcggag gcccagttag    3240
ctctcacaat catatccctg gatacaaggt tcagacgaac ggaccttgga tgcaggtacc    3300
actagaagtg aagagagaag cttgcccagg gactagcgtg atcattgatg gcaactgtga    3360
tggacgggga aaatcaacca gatccaccac ggatagcggg aaagttattc ctgaatggtg    3420
ttgccgctcc tgcacaatgc cgcctgtgag cttccatggt agtgatgggt gttggtatcc    3480
catgaaaatt aggccaagga aaacgcatga agccatctg gtgcgctcct gggttacagc    3540
tggagaaata catgctgtcc cttttggttt ggtgagcatg atgatagcaa tggaagtggt    3600
cctaaggaaa agacagggac caaagcaaat gttggttgga ggagtagtgc tcttgggagc    3660
aatgctggtc gggcaagtaa ctctccttga tttgctgaaa ctcacagtgg ctgtgggatt    3720
gcatttccat gagatgaaca atggaggaga cgccatgtat atggcgttga ttgctgcctt    3780
ttcaatcaga ccagggctgc tcatcggctt tgggctcagg acctatggca gccctcggga    3840
acgccttgtg ctgaccctag gagcagccat ggtggagatt gccttgggtg gcgtgatggg    3900
cggcctgtgg aagtatctaa atgcagtttc tctctgcatc ctgacaataa atgctgttgc    3960
ttctaggaaa gcatcaaata ccatcttgcc cctcatggct ctgttgacac cggtcaccat    4020
ggctgaggtg agacttgccg caatgttctt ttgtgccatg gttatcatag ggtccttca    4080
ccagaatttc aaggacacct ccatgcagaa gactataccct ctggtggccc tcacactcac    4140
atcttacctg ggcttgacac aacctttttt gggcctgtgt gcatttctgg caacccgcat    4200
atttgggcga aggagtatcc cagtgaatga ggcactcgca gcagctggtc tagtgggagt    4260
gctggcagga ctggcttttc aggagatgga gaacttcctt ggtccgattg cagttggagg    4320
actcctgatg atgctggtta gcgtggctgg gagggtggat gggctagagc tcaagaagct    4380
tggtgaagtt tcatgggaag aggaggcgga gatcagcggg agttccgccc gctatgatgt    4440
ggcactcagt gaacaagggg agttcaagct gctttctgaa gagaaagtgc catgggacca    4500
ggttgtgatg acctcgctgg ccttggttgg ggctgccctc catccatttg ctcttctgct    4560
ggtccttgct gggtggctgt ttcatgtcag gggagctagg agaagtgggg atgtcttgtg    4620
ggatattccc actcctaaga tcatcgagga atgtgaacat ctggaggatg ggatttatgg    4680
catattccag tcaaccttct gggggcctc ccagcgagga gtgggagtgg cacagggagg    4740
ggtgttccac acaatgtggc atgtcacaag aggagcttc cttgtcagga atggcaagaa    4800
gttgattcca tcttgggctt cagtaaagga agaccttgtc gcctatggtg gctcatggaa    4860
gttggaaggc agatgggatg gagaggaaga ggtccagttg atcgcggctg ttccaggaaa    4920
```

```
gaacgtggtc aacgtccaga caaaaccgag cttgttcaaa gtgaggaatg ggggagaaat    4980
cggggctgtc gctcttgact atccgagtgg cacttcagga tctcctattg ttaacaggaa    5040
cggagaggtg attgggctgt acggcaatgg catccttgtc ggtgacaact ccttcgtgtc    5100
cgccatatcc cagactgagg tgaaggaaga aggaaaggag gagctccaag agatcccgac    5160
aatgctaaag aaaggaatga caactgtcct tgattttcat cctggagctg gaagacaag     5220 acgtttcctc ccacagatct tggccgagtg cgcacggaga cgcttgcgca ctcttgtgtt    5280
ggcccccacc agggttgttc tttctgaaat gaaggaggct tttcacggcc tggacgtgaa    5340
attccacaca caggcttttt ccgctcacgg cagcgggaga gaagtcattg atgccatgtg    5400
ccatgccacc ctaacttaca ggatgttgga accaactagg gttgttaact gggaagtgat    5460
cattatggat gaagcccatt ttttggatcc agctagcata gccgctagag gttgggcagc    5520
gcacagagct agggcaaatg aaagtgcaac aatcttgatg acagccacac cgcctgggac    5580
tagtgatgaa tttccacatt caaatggtga atagaagat gttcaaacgg acatacccag     5640
tgagccctgg aacacagggc atgactggat cctagctgac aaaaggccca cggcatggtt    5700
ccttccatcc atcagagctg caaatgtcat ggctgcctct ttgcgtaagg ctggaaagag    5760
tgtggtggtc ctgaacagga aaacctttga gagagaatac cccacgataa agcagaagaa    5820
acctgacttt atattggcca ctgacatagc tgaaatggga gccaaccttt gcgtggagcg    5880
agtgctggat tgcaggacgg ctttttaagcc tgtgcttgtg gatgaaggga ggaaggtggc    5940 aataaagg ccacttcgta tctccgcatc ctctgctgct caaggaggg ggcgcattgg     6000 gagaaatccc aacagagatg gagactcata ctactattct gagcctacaa gtgaaaataa    6060
tgcccaccac gtctgctggt tggaggcctc aatgctcttg acaacatgg aggtgagggg     6120 tggaatggtc gccccactct atggcgttga aggaactaaa acaccagttt cccctggtga    6180
aatgagactg agggatgacc agaggaaagt cttcagagaa ctagtgagga attgtgacct    6240
gcccgtttgg ctttcgtggc aagtggccaa ggctggtttg aagacgaatg atcgtaagtg    6300
gtgttttgaa ggccctgagg aacatgagat cttgaatgac agcggtgaaa cagtgaagtg    6360
cagggctcct ggaggagcaa agaagcctct gcgcccaagg tggtgtgatg aaagggtgtc    6420
atctgaccag agtgcgctgt ctgaatttat taagtttgct gaaggtagga ggggagctgc    6480
tgaagtgcta gttgtgctga gtgaactccc tgatttcctg gctaaaaaag gtggagaggc    6540
aatggatacc atcagtgtgt tcctccactc tgaggaaggc tctagggctt accgcaatgc    6600
actatcaatg atgcctgagg caatgacaat agtcatgctg tttatactgg ctggactact    6660
gacatcggga atggtcatct ttttcatgtc tcccaaaggc atcagtagaa tgtctatggc    6720
gatgggcaca atgccggct gtggatatct catgttcctt ggaggcgtca acccactca     6780 catctcctat gtcatgctca tattctttgt cctgatggtg gttgtgatcc ccgagccagg    6840
gcaacaaagg tccatccaag acaaccaagt ggcatacctc attattggca tcctgacgct    6900
ggtttcagcg gtggcagcca acgagctagg catgctggag aaaaccaaag aggacctctt    6960
tgggaagaag aacttaattc catctagtgc ttcaccctgg agttggccgg atcttgacct    7020
gaagccagga gctgcctgga cagtgtacgt tggcattgtt acaatgctct ctccaatgtt    7080
gcaccactgg atcaaagtcg aatatggcaa cctgtctctg tctggaatag cccagtcagc    7140
ctcagtcctt tctttcatgg acaaggggat accattcatg aagatgaata tctcggtcat    7200
aatgctgctg gtcagtggct ggaattcaat aacagtgatg cctctgctct gtggcatagg    7260
```

```
gtgcgccatg ctccactggt ctctcatttt acctggaatc aaagcgcagc agtcaaagct    7320
agcacagaga agggtgttcc atggcgttgc cgagaaccct gtggttgatg ggaatccaac    7380
agttgacatt gaggaagctc ctgaaatgcc tgcccttttat gagaagaaac tggctctata   7440
tctccttctt gctctcagcc tagcttctgt tgccatgtgc agaacgccct tttcattggc    7500
tgaaggcatt gtcctagcat cagctgcctt agggccgctc atagagggaa acaccagcct    7560
tctttggaat ggacccatgg ctgtctccat gacaggagtc atgaggggga atcactatgc    7620
ttttgtggga gtcatgtaca atctatggaa gatgaaaact ggacgccggg ggagcgcgaa    7680
tggaaaaact ttgggtgaag tctggaagag ggaactgaat ctgttggaca agcgacagtt    7740
tgagttgtat aaaaggaccg acattgtgga ggtggatcgt gatacggcac gcaggcattt    7800
ggccgaaggg aaggtggaca ccggggtggc ggtctccagg gggaccgcaa agttaaggtg    7860
gttccatgag cgtggctatg tcaagctgga aggtaggggtg attgacctgg ggtgtggccg    7920
cggaggctgg tgttactacg ctgctgcgca aaaggaagtg agtggggtca aggatttac    7980 tcttggaaga gacggccatg agaaacccat gaatgtgcaa agtctgggat ggaacatcat    8040
caccttcaag gacaaaactg atatccaccg cctagaacca gtgaaatgtg acacccttt    8100 gtgtgacatt ggagagtcat catcgtcatc ggtcacagag ggggaaagga ccgtgagagt    8160
tcttgatact gtagaaaaat ggctggcttg tggggttgac aacttctgtg tgaaggtgtt    8220
agctccatac atgccagatg ttcttgagaa actggaattg ctccaaagga ggtttggcgg    8280
aacagtgatc aggaaccctc tctccaggaa ttccactcat gaaatgtact acgtgtctgg    8340
agcccgcagc aatgtcacat ttactgtgaa ccaaacatcc cgcctcctga tgaggagaat    8400
gaggcgtcca actggaaaag tgaccctgga ggctgacgtc atcctcccaa ttgggacacg    8460
cagtgttgag acagacaagg gaccctgga caaagaggcc atagaagaaa gggttgagag    8520
gataaaatct gagtacatga cctcttggtt ttatgacaat gacaacccct acaggacctg    8580
gcactactgt ggctcctatg tcacaaaaac ctcaggaagt cgcggcagca tggtaaatgg    8640
tgttattaaa attctgacat atccatggga caggatagag gaggtcacaa gaatggcaat    8700
gactgacaca ccccttttg acagcaaag agtgtttaaa gaaaaagttg acaccagagc    8760
aaaggatcca ccagcgggaa ctaggaagat catgaaagtt gtcaacaggt ggctgttccg    8820
ccacctggcc agagaaaaga accccagact gtgcacaaag gaagaattta ttgcaaaagt    8880
ccgaagtcat gcagccattg agcttaccct ggaagaacaa gaacagtgga agactgccaa    8940
tgaggctgtc caagacccaa agttctggga actggtggat gaagaaagga gctgcacca    9000 acaaggcagg tgtcggactt gtgtgtacaa catgatgggg aaaagagaga gaagctgtc    9060 agagtttggg aaagcaaagg gaagccgtgc catatggtat atgtggctgg gagcgcggta    9120
tcttgagttt gaggccctgg gattcctgaa tgaggaccat tgggcttcca gggaaaactc    9180
aggaggagga gtgaaggca ttggcttaca ataccctagga tatgtgatca gagacctggc    9240
tgcaatggat ggtggtggat ctacgcgga tgacaccgct ggatgggaca cgcgcatcac    9300
agaggcagac cttgatgatg aacaggagat cttgaactac atgagcccac atcacaaaaa    9360
actggcacaa gcagtgatgg aaatgacata caagaacaaa gtggtgaaag tgttgagacc    9420
agccccagga gggaaagcct acatggatgt cataagtcga cgagaccaga gggatccgg    9480 gcaggtagtg acttatgctc tgaacacaat caccaacttg aaagtccaat tgatcagaat    9540
ggcagaagca gagatggtga tacatcacca acatgttcaa gattgtgatg aatcagttct    9600
gaccaggctg gaggcatggc tcactgagca cggatgtgac agactgaaga ggatggcggt    9660
```

| | | | | |
|---|---|---|---|---|
| gagtggagac | gactgtgtgg | tccggcccat | cgatgacagg | ttcggcctgg | ccctgtccca | 9720 |
| tctcaacgcc | atgtccaagg | ttagaaagga | catatctgaa | tggcagccat | caaagggtg | 9780 |
| gaatgattgg | gagaatgtgc | ccttctgttc | ccaccacttc | catgaactac | agctgaagga | 9840 |
| tggcaggagg | attgtggtgc | cttgccgaga | acaggacgag | ctcattggga | gaggaagggt | 9900 |
| gtctccagga | aacggctgga | tgatcaagga | aacagcttgc | ctcagcaaag | cctatgccaa | 9960 |
| catgtggtca | ctgatgtatt | ttcacaaaag | ggacatgagg | ctactgtcat | tggctgtttc | 10020 |
| ctcagctgtt | cccacctcat | gggttccaca | aggacgcaca | acatggtcga | ttcatgggaa | 10080 |
| aggggagtgg | atgaccacgg | aagacatgct | tgaggtgtgg | aacagagtat | ggataaccaa | 10140 |
| caacccacac | atgcaggaca | agacaatggt | gaaaaatgg | agagatgtcc | cttatctaac | 10200 |
| caagagacaa | gacaagctgt | gcggatcact | gattggaatg | accaataggg | ccacctgggc | 10260 |
| ctcccacatc | catttagtca | tccatcgtat | ccgaacgctg | attggacagg | agaaatacac | 10320 |
| tgactaccta | acagtcatgg | acaggtattc | tgtggatgct | gacctgcaac | tgggtgagct | 10380 |
| tatctgaaac | accatctaac | aggaataacc | gggatacaaa | ccacgggtgg | agaaccggac | 10440 |
| tccccacaac | ctgaaaccgg | gatataaacc | acggctggag | aaccgggctc | cgcacttaaa | 10500 |
| atgaaacaga | aaccgggata | aaaactacgg | atggagaacc | ggactccaca | cattgagaca | 10560 |
| gaagaagttg | tcagcccaga | accccacacg | agttttgcca | ctgctaagct | gtgaggcagt | 10620 |
| gcaggctggg | acagccgacc | tccaggttgc | gaaaaacctg | gtttctggga | cctcccaccc | 10680 |
| cagagtaaaa | agaacggagc | ctccgctacc | accctcccac | gtggtggtag | aaagacgggg | 10740 |
| tctagaggtt | agaggagacc | ctccagggaa | caaatagtgg | gaccatattg | acgccaggga | 10800 |
| aagaccggag | tggttctctg | cttttcctcc | agaggtctgt | gagcacagtt | tgctcaagaa | 10860 |
| taagcagacc | tttggatgac | aaacacaaaa | ccactggccg | gcatggtccc | agcctcctcg | 10920 |
| ctggcgccgg | ctgggcaaca | ttccgagggg | accgtcccct | cggtaatggc | gaatgggacg | 10980 |
| aattctgaac | cagtcctaaa | acgagtaaat | aggaccggca | attcttcaag | caataaacag | 11040 |
| gaataccaat | tattaaaaga | taacttagtc | agatcgtaca | ataaagcttt | gaagaaaaat | 11100 |
| gcgccttatt | caatctttgc | tataaaaaat | ggcccaaaat | ctcacattgg | aagacatttg | 11160 |
| atgacctcat | ttcttcaat | gaagggccta | acggagttga | ctaatgttgt | gggaaattgg | 11220 |
| agcgataagc | gtgcttctgc | cgtggccagg | acaacgtata | ctcatcagat | aacagcaata | 11280 |
| cctgatcact | acttcgcact | agtttctcgg | tactatgcat | atgatccaat | atcaaaggaa | 11340 |
| atgatagcat | tgaaggatga | gactaatcca | attgaggagt | ggcagcatat | agaacagcta | 11400 |
| aagggtagtg | ctgaaggaag | catacgatac | cccgcatgga | atgggataat | atcacaggag | 11460 |
| gtactagact | acctttcatc | ctacataaat | agacgcatat | aagtacgcat | ttaagcataa | 11520 |
| acacgcacta | tgccgttctt | ctcatgtata | tatatataca | ggcaacacgc | agatataggt | 11580 |
| gcgacgtgaa | cagtgagctg | tatgtgcgca | gctcgcgttg | catttcgga | agcgctcgtt | 11640 |
| ttcggaaacg | ctttgaagtt | cctattccga | agttcctatt | ctctagaaag | tataggaact | 11700 |
| tcagagcgct | tttgaaaacc | aaaagcgctc | tgaagacgca | ctttcaaaaa | accaaaaacg | 11760 |
| caccggactg | taacgagcta | ctaaaatatt | gcgaataccg | cttccacaaa | cattgctcaa | 11820 |
| aagtatctct | tgctatata | tctctgtgct | atatccctat | ataacctacc | catccacctt | 11880 |
| tcgctccttg | aacttgcatc | taaactcgac | ctctacattt | tttatgttta | tctctagtat | 11940 |
| tactctttag | acaaaaaaat | tgtagtaaga | actattcata | gagtgaatcg | aaaacaatac | 12000 |

```
gaaaatgtaa acatttccta tacgtagtat atagagacaa aatagaagaa accgttcata   12060
attttctgac caatgaagaa tcatcaacgc tatcactttc tgttcacaaa gtatgcgcaa   12120
tccacatcgg tatagaatat aatcggggat gcctttatct tgaaaaaatg cacccgcagc   12180
ttcgctagta atcagtaaac gcgggaagtg gagtcaggct ttttttatgg aagagaaaat   12240
agacaccaaa gtagccttct tctaaccttta acggacctac agtgcaaaaa gttatcaaga   12300
gactgcatta tagagcgcac aaaggagaaa aaaagtaatc taagatgctt tgttagaaaa   12360
atagcgctct cgggatgcat ttttgtagaa caaaaagaa gtatagattc tttgttggta   12420
aaatagcgct ctcgcgttgc atttctgttc tgtaaaaatg cagctcagat tctttgtttg   12480
aaaaattagc gctctcgcgt tgcattttg ttttacaaaa atgaagcaca gattcttcgt   12540
tggtaaaata gcgctttcgc gttgcatttc tgttctgtaa aaatgcagct cagattcttt   12600
gtttgaaaaa ttagcgctct cgcgttgcat ttttgttcta caaaatgaag cacagatgct   12660
tcgttaacaa agatatgcta ttgaagtgca agatggaaac gcagaaaatg aaccggggat   12720
gcgacgtgca agattaccta tgcaatagat gcaatagttt ctccaggaac cgaaatacat   12780
acattgtctt ccgtaaagcg ctagactata tattattata caggttcaaa tatactatct   12840
gtttcaggga aaactcccag gttcggatgt tcaaaattca atgatgggta acaagtacga   12900
tcgtaaatct gtaaaacagt ttgtcggata ttaggctgta tctcctcaaa gcgtattcga   12960
atatcattga gaagctgcag gcaagtgcac aaacaatact taaataaata ctactcagta   13020
ataacctatt tcttagcatt tttgacgaaa tttgctattt tgttagagtc ttttacacca   13080
tttgtctcca cacctccgct tacatcaaca ccaataacgc catttaatct aagcgcatca   13140
ccaacatttt ctggcgtcag tccaccagct aacataaaat gtaagctttc ggggctctct   13200
tgccttccaa cccagtcaga aatcgagttc caatccaaaa gttcacctgt cccacctgct   13260
tctgaatcaa acaagggaat aaacgaatga ggtttctgtg aagctgcact gagtagtatg   13320
ttgcagtctt ttggaaatac gagtctttta ataactggca aaccgaggaa ctcttggtat   13380
tcttgccacg actcatctcc atgcagttgg acgatatcaa tgccgtaatc attgaccaga   13440
gccaaaacat cctccttagg ttgattacga aacacgccaa ccaagtattt cggagtgcct   13500
gaactatttt tatatgcttt tacaagactt gaaattttcc ttgcaataac cgggtcaatt   13560
gttctctttc tattgggcac acatataata cccagcaagt cagcatcgga atctagagca   13620
cattctgcgg cctctgtgct ctgcaagccg caaactttca ccaatggacc agaactacct   13680
gtgaaattaa taacagacat actccaagct gcctttgtgt gcttaatcac gtatactcac   13740
gtgctcaata gtcaccaatg ccctccctct tggccctcct cctttctttt tttcgaccgc   13800
tagcgtcgac agcgacacac ttgcatcgga tgcagcccgg ttaacgtgcc ggcacggcct   13860
gggtaaccag gtattttgtc cacataaccg tgcgcaaaat gttgtggata agcaggacac   13920
agcagcaatc cacagcaggc atacaaccgc acaccgaggt tactccgttc tacaggttac   13980
gacgacatgt caatacttgc ccttgacagg cattgatgga atcgtagtct cacgctgata   14040
gtctgatcga caatacaagt gggaccgtgg tcccagaccg ataatcagac cgacaacacg   14100
agtgggatcg tggtcccaga ctaataatca gaccgacgat acgagtggga ccgtggtccc   14160
agactaataa tcagaccgac gatacgagtg ggaccgtggt tccagactaa taatcagacc   14220
gacgatacga gtgggaccgt ggtcccagac taataatcag accgacgata cgagtgggac   14280
catggtccca gactaataat cagaccgacg atacgagtgg gaccgtggtc ccagtctgat   14340
tatcagaccg acgatacgag tgggaccgtg gtcccagact aataatcaga ccgacgatac   14400
```

```
gagtgggacc gtggtcccag actaataatc agaccgacga tacgagtggg accgtggtcc   14460
cagtctgatt atcagaccga cgatacaagt ggaacagtgg gcccagagag aatattcagg   14520
ccagttatgc tttctggcct gtaacaaagg acattaagta aagacagata aacgtagact   14580
aaaacgtggt cgcatcaggg tgctggcttt tcaagttcct taagaatggc ctcaattttc   14640
tctatacact cagttggaac acgggacctg tccaggttaa gcaccatttt atcgcccttg   14700
tacaatactg tcgctccagg agcaaactga tgtcgtgagc ttaaactagt tcttgatgca   14760
gatgacgttt taagcacaga agttaaaaga gtgataactt cttcagcttc aaatatcacc   14820
ccagcttttt tctgctcatg aaggttagat gcctgctgct taagtaattc ctctttatct   14880
gtaaaggctt tttgaagtgc atccctgac cgggcagata gttcaccggg gtgagaaaaa   14940
agagcaacaa ctgatttagg caatttggcg gtgttgatac agcgggtaat aatcttacgt   15000
gaaatatttt ccgcatcagc cagcgcagaa atatttccag caaattcatt ctgcaatcgg   15060
cttgcataac gctgaccacg ttcataagca cttgttgggc gataatcgtt acccaatctg   15120
gataatgcag ccatctgctc atcatccagc tcgccaacca gaacacgata atcactttcg   15180
gtaagtgcag cagcttttacg acggcgactc ccatcggcaa tttctatgac accagatact   15240
cttcgaccga acgccggtgt ctgttgacca gtcagtagaa aagaagggat gagatcatcc   15300
agtgcgtcct cagtaagcag ctcctggtca cgttcattac ctgaccatac ccgagaggtc   15360
ttctcaacac tatcaccccg gagcacttca agagtaaact tcacatcccg accacataca   15420
ggcaaagtaa tggcattacc gcgagccatt actcctacgc gcgcaattaa cgaatccacc   15480
atcggggcag ctggtgtcga taacgaagta tcttcaaccg gttgagtatt gagcgtatgt   15540
tttggaataa caggcgcacg cttcattatc taatctccca gcgtggttta atcagacgat   15600
cgaaaatttc attgcagaca ggttcccaaa tagaaagagc atttctccag gcaccagttg   15660
aagagcgttg atcaatggcc tgttcaaaaa cagttctcat ccggatctga cctttaccaa   15720
cttcatccgt ttcacgtaca acatttttta gaaccatgct tccccaggca tcccgaattt   15780
gctcctccat ccacggggac tgagagccat tactattgct gtatttggta agcaaaatac   15840
gtacatcagg ctcgaaccct ttaagatcaa cgttcttgag cagatcacga agcatatcga   15900
aaaactgcag tgcggaggtg tagtcaaaca actcagcagg cgtgggaaca atcagcacat   15960
cagcagcaca tacgacatta atcgtgccga tacccaggtt aggcgcgctg tcaataacta   16020
tgacatcata gtcatgagca acagtttcaa tggccagtcg gagcatcagg tgtggatcgg   16080
tgggcagttt accttcatca aatttgccca ttaactcagt ttcaatacgg tgcagagcca   16140
gacaggaagg aataatgtca agccccggcc agcaagtggg ctttattgca taagtgacat   16200
cgtccttttc cccaagatag aaaggcagga gagtgtcttc tgcatgaata tgaagatctg   16260
gtacccatcc gtgatacatt gaggctgttc cctggggtc gttaccttcc acgagcaaaa   16320
cacgtagccc cttcagagcc agatcctgag caagatgaac agaaactgag gttttgtaaa   16380
cgccaccttt atgggcagca accccgatca ccggtggaaa tacgtcttca gcacgtcgca   16440
atcgcgtacc aaaacacatca cgcatatgat taatttgttc aattgtataa ccaacacgtt   16500
gctcaacccg tcctcgaatt tccatatccg ggtgcggtag tcgccctgct ttctcggcat   16560
ctctgatagc ctgagaagaa accccaacta aatccgctgc ttcacctatt ctccagcgcc   16620
gggttatttt cctcgcttcc gggctgtcat cattaaactg tgcaatggcg atagccttcg   16680
tcatttcatg accagcgttt atgcactggt taagtgtttc catgagtttc attctgaaca   16740
```

```
tcctttaatc attgctttgc gttttttat  taaatcttgc aatttactgc aaagcaacaa   16800
caaaatcgca aagtcatcaa aaaccgcaa  agttgtttaa aataagagca acactacaaa   16860
aggagataag aagagcacat acctcagtca cttattatca ctagcgctcg ccgcagccgt   16920
gtaaccgagc atagcgagcg aactggcgag gaagcaaaga agaactgttc tgtcagatag   16980
ctcttacgct cagcgcaaga agaaatatcc accgtgggaa aaactccagg tagaggtaca   17040
cacgcggata gccaattcag agtaataaac tgtgataatc aaccctcatc aatgatgacg   17100
aactaacccc cgatatcagg tcacatgacg aagggaaaga gaaggaaatc aactgtgaca   17160
aactgccctc aaatttggct tccttaaaaa ttacagttca aaaagtatga gaaaatccat   17220
gcaggctgaa ggaaacagca aaactgtgac aaattaccct cagtaggtca gaacaaatgt   17280
gacgaaccac cctcaaatct gtgacagata accctcagac tatcctgtcg tcatggaagt   17340
gatatcgcgg aaggaaaata cgatatgagt cgtctggcgg cctttctttt tctcaatgta   17400
tgagaggcgc attggagttc tgctgttgat ctcattaaca cagacctgca ggaagcggcg   17460
gcggaagtca ggcatacgct ggtaactttg aggcagctgg taacgctcta tgatccagtc   17520
gattttcaga gagacgatgc ctgagccatc cggcttacga tactgacaca gggattcgta   17580
taaacgcatg gcatacggat tggtgatttc ttttgtttca ctaagccgaa actgcgtaaa   17640
ccggttctgt aacccgataa agaagggaat gagatatggg ttgatatgta cactgtaaag   17700
ccctctggat ggactgtgcg cacgtttgat aaaccaagga aaagattcat agccttttc    17760 atcgccggca tcctcttcag ggcgataaaa aaccacttcc ttccccgcga aactcttcaa   17820
tgcctgccgt atatccttac tggcttccgc agaggtcaat ccgaatattt cagcatattt   17880
agcaacatgg atctcgcaga taccgtcatg ttcctgtagg gtgccatcag attttctgat   17940
ctggtcaacg aacagataca gcatacgttt ttgatcccgg gagagactat atgccgcctc   18000
agtgaggtcg tttgactgga cgattcgcgg gctatttta cgtttcttgt gattgataac    18060 cgctgttttcc gccatgacag atccatgtga agtgtgacaa gttttagat tgtcacacta     18120 aataaaaaag agtcaataag cagggataac tttgtgaaaa acagcttct tctgagggca     18180 atttgtcaca gggttaaggg caatttgtca cagacaggac tgtcatttga gggtgatttg   18240
tcacactgaa agggcaattt gtcacaacac cttctctaga accagcatgg ataaaggcct   18300
acaaggcgct ctaaaaaaga agatctaaaa actataaaaa aataattat aaaaatatcc    18360 ccgtggataa gtggataacc ccaagggaag tttttttcagg catcgtgtgt aagcagaata   18420
tataagtgct gttccctggt gcttcctcgc tcactgaccc ggggagggttc gagaaggggg   18480 ggcacccccc ttcggcgtgc gcggtcacgc gcacagggcg cagccctggt taaaaacaag   18540
gtttataaat attggtttaa aagcaggtta aagacaggt tagcggtggc cgaaaaacgg    18600
gcggaaaccc ttgcaaatgc tggattttct gcctgtggac agcccctcaa atgtcaatag   18660
gtgcgcccct catctgtcag cactctgccc ctcaagtgtc aaggatcgcg cccctcatct   18720
gtcagtagtc gcgcccctca gtgtcaata ccgcagggca cttatcccca ggcttgtcca    18780
catcatctgt gggaaactcg cgtaaaatca ggcgttttcg ccgatttgcg aggctggcca   18840
gctccacgtc gccggccgaa atcgagcctg ccctcatct gtcaacgccg cgcgggtga     18900 gtcggccct caagtgtcaa cgtccgcccc tcatctgtca gtgagggcca gttttccgc     18960 gaggtatcca caacgccggc ggccggccgc ggtgtctcgc acacggcttc gacggcgttt   19020
ctggcgcgtt tgcagggcca tagacggccg ccagcccagc ggcgagggca accagccgag   19080
ggcttcgccc tgtcgctcga ctgcggcgag cactactggc tgtaaaagga cagaccacat   19140
```

```
catggttctg tgttcattag gttgttctgt ccattgctga cataatccgc tccacttcaa    19200
cgtaacaccg cacgaagatt tctattgttc ctgaaggcat attcaaatcg ttttcgttac    19260
cgcttgcagg catcatgaca gaacactact tcctataaac gctacacagg ctcctgagat    19320
taataatgcg gatctctacg ataatgggag attttcccga ctgtttcgtt cgcttctcag    19380
tggataacag ccagcttctc tgtttaacag acaaaaacag catatccact cagttccaca    19440
tttccatata aaggccaagg catttattct caggataatt gtttcagcat cgcaaccgca    19500
tcagactccg gcatcgcaaa ctgcacccgg tgccgggcag ccacatccag cgcaaaaacc    19560
ttcgtgtaga cttccgttga actgatggac ttatgtccca tcaggctttg cagaactttc    19620
agcggtatac cggcatacag catgtgcatc gcataggaat ggcggaacgt atgtggtgtg    19680
accggaacag agaacgtcac accgtcagca gcagcggcgg caaccgcctc cccaatccag    19740
gtcctgaccg ttctgtccgt cacttcccag atccgcgctt tctctgtcct tcctgtgcga    19800
cggttacgcc gctccatgag cttatcgcga ataaatacct gtgacggaag atcacttcgc    19860
agaataaata aatcctggtg tccctgttga taccgggaag ccctgggcca acttttggcg    19920
aaaatgagac gttgatcggc acgtaagagg ttccaacttt caccataatg aaataagatc    19980
actaccgggc gtattttttg agttatcgag attttcagga gctaaggaag ctaaaatgga    20040
gaaaaaatc actggatata ccaccgttga tatatcccaa tggcatcgta agaacattt    20100
tgaggcattt cagtcagttg ctcaatgtac ctataaccag accgttcagc tggatattac    20160
ggccttttta aagaccgtaa agaaaaataa gcacaagttt tatccggcct ttattcacat    20220
tcttgcccgc ctgatgaatg ctcatccgga atttcgtatg gcaatgaaag acggtgagct    20280
ggtgatatgg gatagtgttc acccttgtta caccgttttc catgagcaaa ctgaaacgtt    20340
ttcatcgctc tggagtgaat accacgacga tttccggcag tttctacaca tatattcgca    20400
agatgtggcg tgttacggtg aaaacctggc ctatttccct aaagggttta ttgagaatat    20460
gttttttcgtc tcagccaatc cctgggtgag tttcaccagt tttgatttaa acgtggccaa    20520
tatggacaac ttcttcgccc ccgttttcac catgggcaaa tattatacgc aaggcgacaa    20580
ggtgctgatg ccgctggcga ttcaggttca tcatgccgtt tgtgatggct tccatgtcgg    20640
cagaatgctt aatgaattac aacagtactg cgatgagtgg cagggcgggg cgtaattttt    20700
ttaaggcagt tattggtgcc cttaaacgcc tggttgctac gcctgaataa gtgataataa    20760
gcggatgaat ggcagaaatt cgatgataag ctgtcaaaca tgagaattgg tcgaccctgt    20820
ggaatgtgtg tcagttaggg tgtggaaagt ccccaggctc cccagcaggc agaagtatgc    20880
aaagcatgca tctcaattag tcagcaacca ggtgtggaaa gtccccaggc tccccagcag    20940
gcagaagtat gcaaagcatg catctcaatt agtcagcaac catagtcccg ccctaactc    21000
cgcccatccc gcccctaact ccgcccagtt ccgcccattc tccgcccat ggctgactaa    21060
ttttttttat ttatgcagag gccgaggccg cctc                                21094
```

<210> SEQ ID NO 7
<211> LENGTH: 17639
<212> TYPE: DNA
<213> ORGANISM: Artificial Sequence
<220> FEATURE:
<223> OTHER INFORMATION: Synthetic construct pShuttle/EV71

<400> SEQUENCE: 7

```
ttaaaacagc ctgtgggttg cacccactca cagggcccac tgggcgctag tacactggta    60
```

```
tctcggtacc tttgtacgcc tgttttatac cccctccctg atttgcaact tagaagcaac    120
gcaaaccaga tcaatagtag gtgtgacata ccagtcgcat cttgatcaag cacttctgta    180
tccccggacc gagtatcaat agactgtgca cacggttgaa ggagaaaacg tccgttaccc    240
ggctaactac ttcgagaaac ctagtaacgc cattgaagtt gcagagtgtt tcgctcagca    300 ctcccccgt gtagatcagg tcgatgagtc accgcattcc ccacgggcga ccgtggcggt    360
ggctgcgttg gcggcctgcc tatggggtaa cccataggac gctctaatac ggacatggcg    420
tgaagagtct attgagctag ttagtagtcc tccggcccct gaatgcggtt aatcctaact    480
gcggagcaca tacccttaat ccaaagggca gtgtgtcgta acgggcaact ctgcagcgga    540
accgactact ttgggtgtcc gtgtttcttt ttattcttgt attggctgct tatggtgaca    600
attaaagaat tgttaccata tagctattgg attggccatc cagtgtcaaa cagagctatt    660
gtatatctct ttgttggatt tacacctctc actcttgaaa cgttacacac cctcaattac    720
attatactgc tgaacacgaa gcgatgggct cccaggtctc cacacagcga tccggctcgc    780
atgagaattc caactcagcc acggaaggct ccactataaa ttacacaacc attaattact    840
acaaagactc gtatgctgcc actgctggaa agcaaagtct caaacaagat cctgacaagt    900
ttgcgaaccc tgtgaaggac atctttactg aaatggcagc gcccttaaag tctccctctg    960
ctgaagcatg tggctatagc gaccgagtgg cacagcttac cattggaaat tccaccatta    1020
ctacacaaga agcagcaaac ataatagttg ggtatggtga gtggccttca tactgctctg    1080
ataatgatgc aacagcggta gacaaaccta cacggcctga tgtctcagta aatagatttt    1140
acacgctaga cactaagcta tgggagaaat catccaaggg gtggtactgg aagttcccag    1200
atgtactgac tgaaaccgga gttttggtc aaaatgcaca atttcactac ttataccgtt    1260
cagggttctg catccacgtt caatgtaacg ctagcaaatt tcaccaaggg gcgctactcg    1320
ttgcggtatt gcccgagtat gtcattggaa cagtggcagg cggcacaggc acagagaaca    1380
gtcaccctcc ttatatacaa acccaacccg gcgctgatgg atttgaatta caacatccat    1440
atgttcttga tgctggaatt ccaatatctc agttgacagt gtgccctcac cagtggatca    1500
atttacgaac caacaattgt gccaccataa tagtgccata catgaacaca ctacctttg    1560 attccgcatt gaaccactgt aatttcggac tattggtggt gcctatcagc ccgctggatt    1620
tcgaccaagg ggcgacaccg gtaattccta tcactatcac gttggctccg atgtgttctg    1680
agtttgcggg tctcaggcag gcagttgcgc agggtttccc cactgaattg aaacctggca    1740
ctaatcagtt cttaaccacg gatgatggtg tgtcagcacc tatattgcca aatttccacc    1800
ccaccccgtg cattcacata cctggcgagg ttagaaactt actagaactg tgccaggtag    1860
aaaccatttt agaagtcaac aatgtgccca ccaacgcaac cagttgatg gaaaggctac    1920 ggtttccagt gtcagcccaa gcagggaaag gtgagttgtg tgcagtgttc agggccgacc    1980
ctgggaggga tggtccttgg caatccacca tgctaggcca gttgtgtgga tattacaccc    2040
aatggtcagg gtctttggaa gtcactttta tgttcaccgg atcctttatg gcaactggta    2100
aaatgcttat agcttacaca ccccagggg gccctttgcc taaagataga gccacagcta    2160
tgctggggac gcacgtcatc tgggactttg gcttgcaatc gtccgtcacc ctcgtcatac    2220
catggatcag taacactcac tatagggcgc atgctcgaga tggggtgttt gattactaca    2280
ccacaggttt ggttagtata tggtaccaaa caaattatgt agtccctatt ggagcaccta    2340
atactgccta tataatagcg ttggcagcag cccaaaagaa tttcactatg aaattgtgca    2400
aggacaccag tgacatttg caaacggcca ctattcaagg ggacagagtg gcagatgtga    2460
```

```
ttgagagctc tataggagat agtgtgagta aggccctcac ccaagcttta cctgcaccca    2520
caggccaaaa cacccaagtg agcagtcatc gcttagacac tggaaaagta ccagcacttc    2580
aagccgccga aatcggagct tcgtcgaatg ctagtgatga gagtatgatt gagactcggt    2640
gtgttcttaa ctcacatagc acagctgaaa ccacccttga tagtttcttc agtagagcag    2700
gcttagttgg ggagatagat cttcctctaa agggcaccac caatccgaac gggtatgcca    2760
actgggacat agacataacc ggttatgcgc agatgcgcag aaaagtggaa ctattcacct    2820
atatgcgctt tgacgcagag ttcactttg tcgcgtgcac acctaccgga gaggtcgttc     2880
cacagctgct tcaatacatg tttgttccac ccggggcccc caaaccagac tccagagact    2940
ctttggcttg gcaaacggcc acgaacccct cagttttgt caaattatcc gacccaccag      3000
cacaagtctc agtgccattt atgtcacctg caagcgcata ccaatggttt tatgacggat    3060
accctacatt tggagagcac aagcaagaga aggatctcga gtatgggca tgcccgaata     3120 acatgatggg cacattctca gtgcggactg tgggatcgtc acagtcaaaa tatcccttag    3180
tcatcagaat atacatgaga atgaagcacg tcagagcgtg gatacctcgg ccgatgcgca    3240
atcagaacta tttgttcaaa tccaacccaa actatgctgg taattccatt aaaccaactg    3300
gtaccagccg aacggcaatc actacgctcg ggaaattcgg tcagcagtct ggggctattt    3360
atgtgggcaa cctagggta gtaaacagac cctagccac ccatactgac tgggccaact       3420
tggtgtggga agacagctct agagacctcc tagtttcttc aactaccgct caagggtgtg    3480
acaccattgc tcgatgtaac tgccaaaccg gagtgtatta ctgtaactct cgcagaaaac    3540
actatccagt cagttttcg aaacctagtt tggtgtttgt agaagctagt gagtattatc      3600
cagctagata tcagtcccat cttatgcttg ctgagggcca ttcagaacct ggtgattgtg    3660
gcggtattct tagatgccaa cacggtgtgg tgggaattgt ctccactggc ggaagtggcc    3720
ttgtgggatt tgctgacgtt agagatcttc tgtggctaga tgaggaagcg atggagcagg    3780
gggtatctga ttacatcaaa ggtctcggtg atgccttcgg cacaggtttc actgacgcag    3840
tgtctaggga agtggaagcg ttgaagaacc acttaatcgg ctccgaaggg gctgttgaga    3900
agatcttgaa gaacttggtg aagctaattt cagccttagt tatagtcatc agaagtgatt    3960
atgatatggt caccctcaca gccacactag ctctgatcgg gtgccacggg agtccttggg    4020
cgtggatcaa atcaaagaca gcttccatac tgggcattcc catggcacaa aaacagagtg    4080
cctcatggct aaagaagttc aatgacatgg caaatgctgc aaaagggctt gagtggattt    4140
ccaacaagat cagtaagttc attgactggc ttaaagagaa gatcattcca gctgccaaag    4200
agaaagttga gttttgaac aacctaaaac agctcccctt gttggagaac caggtctcca     4260
atcttgaaca gtctgctgcc tcacaagaag acttagaagc tatgtttggt aatgtgtcat    4320
atctggctca cttttgccgc aaattccaac cactctacgc aactgaggcc aagagagtct    4380
acgctttaga gaaaaggatg aataactaca tgcagttcaa gagcaaacac cgtattgaac    4440
ctgtatgctt gatcatcaga ggttccccag gaacgggcaa atcgctcgcc acaggcatta    4500
tagctagagc cattgctgac aagtatcgct ctagtgtata ctcactcccc ccagacccag    4560
atcactttga tgggtataag caacaggtgg tcacggtcat ggatgatctc tgccagaacc    4620
cggacggaaa agacatgtcc ctattttgtc aaatggtttc tacagtagat tttataccac    4680
ccatggcatc actagaggag aaaggagtgt ccttcacctc taagtttgtc attgcatcga    4740
ccaatgctag taacatcata gtccccacag tttcagattc agatgcaatt cgcaggcgat    4800
```

-continued

```
tctatatgga ctgcgatata gaagtgacag attcttacaa gacagacctc ggtcggctgg    4860
acgcaggtag agctgccaag ctttgtacag aaaataacac tgctaatttc aagagatgca    4920
gcccactggt gtgtggtaag gctattcagc tgagagacag gaagtccaaa gtgagatata    4980
gcgtcgacac cgtggtatcg gaactgatca gagagtacaa caatagatct gctattggga    5040
atactataga agcactcttt caaggacccc ctaaattcag gcctataaga attagtctcg    5100
aagaaaagcc agcccagat gccattggtg atttgctcgc tagtgtcgat agcgaggagg    5160
tccgacagta ctgcagggaa caagggtgga taatcccgga acaccaact aatgtggaac    5220 gtcacctcaa tagagcagta ttggtaatgc agtccatcgc cactgtggtt gcagttgtgt    5280
ctcttgttta tgtcatttat aagctgtttg ccgggttcca gggtgcttac tctggagcgc    5340
ccaagcaaat tctcaagaag cccgtgttaa gaacagccac ggtccaaggg cccagcttag    5400
acttcgcctt gtctcttttg aggcgcaaca ttagacaagc gcaaactgac caaggacact    5460
tcaccatgct aggagtgcga gatcgcctag ccatcctgcc gcgccactcg caaccaggga    5520
agaccatctg ggtagagcat aaattaatca atgtactaga tgcagttgag ttggtggatg    5580
agcaaggtgt aaacttggaa ctcacactgg taactttgga caccaatgaa aaatttaggg    5640
atatcaccaa gtttatccca gaagtgatca ccggggcgag tgacgcaact ctagtcatca    5700
acactgagca catgccctca atgtttgtgc cggtgggtga cgttgtgcag tacgggtttc    5760
tgaaccttag tggtaaaccc acacacagaa ccatgatgta taacttcccc acgaaggcag    5820
gacagtgtgg gggggtggtt acctcagttg gtaagatcat tggaatccac attggcggga    5880
atggacgcca gggcttttgc gctggcctaa agaggagtta ttttgccagc gagcaaggag    5940
agatccagtg gatgaagcct aacagagaaa ccgggaggtt gaatattaat ggtccaaccc    6000
gaactaagct ggaacccagt gtattccatg atgtgttcga gggcaacaag gaaccagcgg    6060
tcctgactag taaggacccc agacttgagg ttgattttga gcaagctttg ttctccaagt    6120
atgtgggtaa caccctgcat gaacctgatg agtacgtgac acaggctgct ctccactacg    6180
caaatcagct gaagcaactg gacatcaaca ccagcaagat gagcatggaa gaagcgtgct    6240
atggcacaga atatttagaa gctatagact tgcacaccag tgctggatac ccttatagtg    6300
ctttgggcat caagaaaaga gacatcctcg acccagttac cagagacacc tccaggatga    6360
agttatatat ggataagtat gggttggact tgccttattc cacttatgta aaggatgagc    6420
ttagatctct agataagatc agaaaaggga agtctcgcct gattgaggct agcagcttaa    6480
atgattctgt ctaccttaga atgactttg gacacctta tgaagtgttt cacgccaacc    6540
cagggactgt aacaggatct gcagttgggt gcaaccctga tgtattttgg agcaagttac    6600
caattttgtt accgggttca ctcttttgcat ttgactactc aggatatgat gcaagcctta    6660
gtcctgtgtg gttcagagct ctagagttgg ttctgagaga gatcggttac tcggaggagg    6720
ctgtgtcact catagaaggg atcaatcaca cccaccacgt gtaccgaaac aagacatatt    6780
gtgtacttgg tggaatgccc tcaggctgct ccggtacttc catttcaat tccatgatta    6840 acaacataat catcagaacc ctcctgatta aaacattcaa aggtatagac ttagatgagc    6900
tgaaaatggt agcttatgga gatgacgtgt tggccagcta cccgtttcct attgattgct    6960
tggaattggc taaaacaggc aaagaatatg gctgactat gactcctgct gataaatcac    7020 cttgttttcaa tgaggttacc tgggagaatg caaccttctt aaaacgcggt tttctaccgg    7080
accatcagtt cccttttctg atccatccca ctatgcccat gagggaaatc catgagtcca    7140
tccgctggac caaggacgcg cgcaatactc aagatcatgt gcgctcccctt tgtctcctgg    7200
```

```
catggcataa tggaaaagag gagtatgaga aatttgtgag tacaattaga tcagtccca    7260 ttggaagggc tttagcaata ccaaattttg agaacttgag aagaaattgg ctcgagttat    7320
tttaaactta cagctcaatg ctgaacccca ccagaaatct ggtcgtgtca atgactggtg    7380
ggggtaaatt tgttataacc agaatagcaa aaaaaaaaaa aaaaaaaaaa aaaaaaaaaa    7440
ggccggcatg gtcccagcct cctcgctggc gccggctggg caacattccg aggggaccgt    7500
cccctcggta atggcgaatg ggacgaattc tgaaccagtc ctaaaacgag taaataggac    7560
cggcaattct tcaagcaata aacaggaata ccaattatta aaagataact tagtcagatc    7620
gtacaataaa gctttgaaga aaaatgcgcc ttattcaatc tttgctataa aaaatggccc    7680
aaaatctcac attggaagac atttgatgac ctcatttctt tcaatgaagg gcctaacgga    7740
gttgactaat gttgtgggaa attggagcga taagcgtgct tctgccgtgg ccaggacaac    7800
gtatactcat cagataacag caataccctga tcactacttc gcactagttt ctcggtacta    7860
tgcatatgat ccaatatcaa aggaaatgat agcattgaag gatgagacta atccaattga    7920
ggagtggcag catatagaac agctaaaggg tagtgctgaa ggaagcatac gatacccgc    7980 atggaatggg ataatatcac aggaggtact agactacctt tcatcctaca taatagacg    8040 catataagta cgcatttaag cataaacacg cactatgccg ttcttctcat gtatatatat    8100
atacaggcaa cacgcagata taggtgcgac gtgaacagtg agctgtatgt gcgcagctcg    8160
cgttgcattt tcggaagcgc tcgttttcgg aaacgctttg aagttcctat tccgaagttc    8220
ctattctcta gaaagtatag gaacttcaga gcgcttttga aaaccaaaag cgctctgaag    8280
acgcactttc aaaaaccaa aaacgcaccg gactgtaacg agctactaaa atattgcgaa    8340
taccgcttcc acaaacattg ctcaaaagta tctctttgct atatatctct gtgctatatc    8400
cctatataac ctacccatcc accttctgct ccttgaactt gcatctaaac tcgacctcta    8460 catttttat gtttatctct agtattactc tttagacaaa aaaattgtag taagaactat    8520
tcatagagtg aatcgaaaac aatacgaaaa tgtaaacatt tcctatacgt agtatataga    8580
gacaaaatag aagaaccgt tcataatttt ctgaccaatg aagaatcatc aacgctatca    8640 cttttctgttc acaaagtatg cgcaatccac atcggtatag aatataatcg gggatgcctt    8700
tatcttgaaa aaatgcaccc gcagcttcgc tagtaatcag taaacgcggg aagtggagtc    8760
aggctttttt tatggaagag aaaatagaca ccaaagtagc cttcttctaa ccttaacgga    8820
cctacagtgc aaaaagttat caagagactg cattatagag cgcacaaagg agaaaaaaag    8880
taatctaaga tgctttgtta gaaaatagc gctctcggga tgcattttg tagaacaaa    8940 aagaagtata gattctttgt tggtaaaata gcgctctcgc gttgcatttc tgttctgtaa    9000
aaatgcagct cagattcttt gtttgaaaaa ttagcgctct cgcgttgcat ttttgtttta    9060
caaaaatgaa gcacagattc ttcgttggta aaatagcgct ttcgcgttgc atttctgttc    9120
tgtaaaaatg cagctcagat tctttgtttg aaaaattagc gctctcgcgt tgcatttttg    9180
ttctacaaaa tgaagcacag atgcttcgtt aacaaagata tgctattgaa gtgcaagatg    9240
gaaacgcaga aaatgaaccg gggatgcgac gtgcaagatt acctatgcaa tagatgcaat    9300
agtttctcca ggaaccgaaa tacatacatt gtcttccgta aagcgctaga ctatatatta    9360
ttatacaggt tcaaatatac tatctgtttc agggaaaact cccaggttcg atgttcaaa    9420 attcaatgat gggtaacaag tacgatcgta aatctgtaaa acagtttgtc ggatattagg    9480
ctgtatctcc tcaaagcgta ttcgaatatc attgagaagc tgcaggcaag tgcacaaaca    9540
```

```
atacttaaat aaatactact cagtaataac ctatttctta gcattttfga cgaaatttgc   9600
tattttgtta gagtctttta caccatttgt ctccacacct ccgcttacat caacaccaat   9660
aacgccattt aatctaagcg catcaccaac attttctggc gtcagtccac cagctaacat   9720
aaaatgtaag ctttcggggc tctcttgcct tccaacccag tcagaaatcg agttccaatc   9780
caaaagttca cctgtcccac ctgcttctga atcaaacaag ggaataaacg aatgaggttt   9840
ctgtgaagct gcactgagta gtatgttgca gtcttttgga aatacgagtc ttttaataac   9900
tggcaaaccg aggaactctt ggtattcttg ccacgactca tctccatgca gttggacgat   9960
atcaatgccg taatcattga ccagagccaa aacatcctcc ttaggttgat tacgaaacac  10020
gccaaccaag tatttcggag tgcctgaact attttatat gcttttacaa gacttgaaat  10080
tttccttgca ataaccgggt caattgttct cttttctattg ggcacacata taatacccag  10140
caagtcagca tcggaatcta gagcacattc tgcggcctct gtgctctgca agccgcaaac  10200
tttcaccaat ggaccagaac tacctgtgaa attaataaca gacatactcc aagctgcctt  10260
tgtgtgctta atcacgtata ctcacgtgct caatagtcac caatgccctc cctcttggcc  10320
ctcctccttt tcttttttcg accgctagcg tcgacagcga cacacttgca tcggatgcag  10380
cccggttaac gtgccggcac ggcctgggta accaggtatt ttgtccacat aaccgtgcgc  10440
aaaatgttgt ggataagcag gacacagcag caatccacag caggcataca accgcacacc  10500
gaggttactc cgttctacag gttacgacga catgtcaata cttgcccttg acaggcattg  10560
atggaatcgt agtctcacgc tgatagtctg atcgacaata caagtgggac cgtggtccca  10620
gaccgataat cagaccgaca acacgagtgg gatcgtggtc ccagactaat aatcagaccg  10680
acgatacgag tgggaccgtg gtcccagact aataatcaga ccgacgatac gagtgggacc  10740
gtggttccag actaataatc agaccgacga tacgagtggg accgtggtcc cagactaata  10800
atcagaccga cgatacgagt gggaccatgg tcccagacta ataatcagac cgacgatacg  10860
agtgggaccg tggtcccagt ctgattatca gaccgacgat acgagtggga ccgtggtccc  10920
agactaataa tcagaccgac gatacgagtg gaccgtggt cccagactaa taatcagacc  10980
gacgatacga gtgggaccgt ggtcccagtc tgattatcag accgacgata caagtggaac  11040
agtgggccca gagagaatat tcaggccagt tatgcttcct ggcctgtaac aaaggacatt  11100
aagtaaagac agataaacgt agactaaaac gtggtcgcat caggtgctg gcttttcaag  11160
ttccttaaga atggcctcaa ttttctctat acactcagtt ggaacacggg acctgtccag  11220
gttaagcacc attttatcgc ccttatacaa tactgtcgct ccaggagcaa actgatgtcg  11280
tgagcttaaa ctagttcttg atgcagatga cgttttaagc acagaagtta aaagagtgat  11340
aacttcttca gcttcaaata tcaccccagc tttttttctgc tcatgaaggt tagatgcctg  11400
ctgcttaagt aattcctctt tatctgtaaa ggcttttga agtgcatcac ctgaccgggc  11460
agatagttca ccggggtgag aaaaaagagc aacaactgat ttaggcaatt tggcggtgtt  11520
gatacagcgg gtaataatct tacgtgaaat attttccgca tcagccagcg cagaaatatt  11580
tccagcaaat tcattctgca atcggcttgc ataacgctga ccacgttcat aagcacttgt  11640
tgggcgataa tcgttaccca atctggataa tgcagccatc tgctcatcat ccagctcgcc  11700
aaccagaaca cgataatcac tttcggtaag tgcagcagct ttacgacggc gactcccatc  11760
ggcaatttct atgacaccag atactcttcg accgaacgcc ggtgtctgtt gaccagtcag  11820
tagaaaagaa gggatgagat catccagtgc gtcctcagta agcagctcct ggtcacgttc  11880
attacctgac catacccgag aggtcttctc aacactatca ccccggagca cttcaagagt  11940
```

```
aaacttcaca tcccgaccac atacaggcaa agtaatggca ttaccgcgag ccattactcc    12000
tacgcgcgca attaacgaat ccaccatcgg ggcagctggt gtcgataacg aagtatcttc    12060
aaccggttga gtattgagcg tatgttttgg aataacaggc gcacgcttca ttatctaatc    12120
tcccagcgtg gtttaatcag acgatcgaaa atttcattgc agacaggttc ccaaatagaa    12180
agagcatttc tccaggcacc agttgaagag cgttgatcaa tggcctgttc aaaaacagtt    12240
ctcatccgga tctgaccttt accaacttca tccgtttcac gtacaacatt ttttagaacc    12300
atgcttcccc aggcatcccg aatttgctcc tccatccacg gggactgaga gccattacta    12360
ttgctgtatt tggtaagcaa aatacgtaca tcaggctcga acctttaag atcaacgttc    12420 ttgagcagat cacgaagcat atcgaaaaac tgcagtgcgg aggtgtagtc aaacaactca    12480
gcaggcgtgg gaacaatcag cacatcagca gcacatacga cattaatcgt gccgataccc    12540
aggttaggcg cgctgtcaat aactatgaca tcatagtcat gagcaacagt ttcaatggcc    12600
agtcggagca tcaggtgtgg atcggtgggc agtttacctt catcaaattt gcccattaac    12660
tcagtttcaa tacggtgcag agccagacag gaaggaataa tgtcaagccc cggccagcaa    12720
gtgggcttta ttgcataagt gacatcgtcc ttttccccaa gatagaaagg caggagagtg    12780
tcttctgcat gaatatgaag atctggtacc catccgtgat acattgaggc tgttccctgg    12840
gggtcgttac cttccacgag caaaacacgt agcccttca gagccagatc ctgagcaaga    12900
tgaacagaaa ctgaggtttt gtaaacgcca cctttatggg cagcaacccc gatcaccggt    12960
ggaaatacgt cttcagcacg tcgcaatcgc gtaccaaaca catcacgcat atgattaatt    13020
tgttcaattg tataaccaac acgttgctca acccgtcctc gaatttccat atccgggtgc    13080
ggtagtcgcc ctgctttctc ggcatctctg atagcctgag aagaaacccc aactaaatcc    13140
gctgcttcac ctattctcca gcgccgggtt attttcctcg cttccgggct gtcatcatta    13200
aactgtgcaa tggcgatagc cttcgtcatt tcatgaccag cgtttatgca ctggttaagt    13260
gtttccatga gtttcattct gaacatcctt taatcattgc tttgcgtttt tttattaaat    13320
cttgcaattt actgcaaagc aacaacaaaa tcgcaaagtc atcaaaaaac cgcaaagttg    13380
tttaaaataa gagcaacact acaaaaggag ataagaagag cacatacctc agtcacttat    13440
tatcactagc gctcgccgca gccgtgtaac cgagcatagc gagcgaactg gcgaggaagc    13500
aaagaagaac tgttctgtca gatagctctt acgctcagcg caagaagaaa tatccaccgt    13560
gggaaaaact ccaggtagag gtacacacgc ggatagccaa ttcagagtaa taaactgtga    13620
taatcaaccc tcatcaatga tgacgaacta accccgata tcaggtcaca tgacgaaggg    13680
aaagagaagg aaatcaactg tgacaaactg ccctcaaatt tggcttcctt aaaaattaca    13740
gttcaaaaag tatgagaaaa tccatgcagg ctgaaggaaa cagcaaaact gtgacaaatt    13800
accctcagta ggtcagaaca aatgtgacga accaccctca aatctgtgac agataaccct    13860
cagactatcc tgtcgtcatg gaagtgatat cgcggaagga aaatacgata tgagtcgtct    13920
ggcggccttt cttttttctca atgtatgaga ggcgcattgg agttctgctg ttgatctcat    13980
taacacagac ctgcaggaag cggcggcgga agtcaggcat acgctggtaa ctttgaggca    14040
gctggtaacg ctctatgatc cagtcgattt tcagagagac gatgcctgag ccatccggct    14100
tacgatactg acacagggat tcgtataaac gcatggcata cggattggtg atttcttttg    14160
tttcactaag ccgaaactgc gtaaaccggt tctgtaaccc gataaagaag ggaatgagat    14220
atgggttgat atgtacactg taaagccctc tggatggact gtgcgcacgt ttgataaacc    14280
```

```
aaggaaaaga ttcatagcct tttcatcgc cggcatcctc ttcagggcga taaaaaacca  14340
cttccttccc cgcgaaactc ttcaatgcct gccgtatatc cttactggct tccgcagagg  14400
tcaatccgaa tatttcagca tatttagcaa catggatctc gcagataccg tcatgttcct  14460
gtagggtgcc atcagatttt ctgatctggt caacgaacag atacagcata cgttttgat   14520 cccgggagag actatatgcc gcctcagtga ggtcgtttga ctggacgatt cgcgggctat  14580
ttttacgttt cttgtgattg ataaccgctg tttccgccat gacagatcca tgtgaagtgt  14640
gacaagtttt tagattgtca cactaaataa aaaagagtca ataagcaggg ataactttgt  14700
gaaaaaacag cttcttctga gggcaatttg tcacagggtt aagggcaatt tgtcacagac  14760
aggactgtca tttgagggtg atttgtcaca ctgaaagggc aatttgtcac aacaccttct  14820
ctagaaccag catggataaa ggcctacaag gcgctctaaa aaagaagatc taaaaactat  14880 aaaaaaata attataaaaa tatccccgtg gataagtgga taaccccaag ggaagttttt  14940
tcaggcatcg tgtgtaagca gaatatataa gtgctgttcc ctggtgcttc ctcgctcact  15000
cgaccgggag ggttcgagaa gggggggcac ccccttcgg cgtgcgcggt cacgcgcaca  15060
gggcgcagcc ctggttaaaa acaaggttta taaatattgg tttaaaagca ggttaaaaga  15120
caggttagcg gtgccgaaa aacgggcgga aacccttgca aatgctggat tttctgcctg  15180
tggacagccc ctcaaatgtc aataggtgcg cccctcatct gtcagcactc tgcccctcaa  15240
gtgtcaagga tcgcgcccct catctgtcag tagtcgcgcc cctcaagtgt caataccgca  15300
gggcacttat ccccaggctt gtccacatca tctgtgggaa actcgcgtaa aatcaggcgt  15360
tttcgccgat ttgcgaggct ggccagctcc acgtcgccgg ccgaaatcga gcctgcccct  15420
catctgtcaa cgccgcgccg ggtgagtcgg cccctcaagt gtcaacgtcc gcccctcatc  15480
tgtcagtgag ggcaagtttt tccgcgaggt atccacaacg ccggcggccg gccgcggtgt  15540
ctcgcacacg gcttcgacgg cgtttctggc gcgtttgcag ggccatagac ggccgccagc  15600
ccagcggcga gggcaaccag ccgagggctt cgccctgtcg ctcgactgcg gcgagcacta  15660
ctggctgtaa aaggacagac cacatcatgg ttctgtgttc attaggttgt tctgtccatt  15720
gctgacataa tccgctccac ttcaacgtaa caccgcacga agatttctat tgttcctgaa  15780
ggcatattca aatcgttttc gttaccgctt gcaggcatca tgacagaaca ctacttccta  15840
taaacgctac acaggctcct gagattaata atgcggatct ctacgataat gggagatttt  15900
cccgactgtt tcgttcgctt tcagtggat aacagccagc ttctctgttt aacagacaaa   15960
aacagcatat ccactcagtt ccacatttcc atataaaggc caaggcattt attctcagga  16020
taattgtttc agcatcgcaa ccgcatcaga ctccggcatc gcaaactgca cccggtgccg  16080
ggcagccaca tccagcgcaa aaaccttcgt gtagacttcc gttgaactga tggacttatg  16140
tcccatcagg ctttgcagaa ctttcagcgg tataccggca tacagcatgt gcatcgcata  16200
ggaatggcgg aacgtatgtg gtgtgaccgg aacagagaac gtcacaccgt cagcagcagc  16260
ggcggcaacc gcctccccaa tccaggtcct gaccgttctg tccgtcactt cccagatccg  16320
cgctttctct gtccttcctg tgcgacggtt acgccgctcc atgagcttat cgcgaataaa  16380
tacctgtgac ggaagatcac ttcgcagaat aaataaatcc tggtgtccct gttgataccg  16440
ggaagccctg ggccaacttt tggcgaaaat gagacgttga tcggcacgta agaggttcca  16500
actttcacca taatgaaata agatcactac cgggcgtatt ttttgagtta tcgagatttt  16560
caggagctaa ggaagctaaa atggagaaaa aaatcactgg atataccacc gttgatatat  16620
cccaatggca tcgtaaagaa cattttgagg catttcagtc agttgctcaa tgtacctata  16680
```

-continued

```
accagaccgt tcagctggat attacggcct ttttaaagac cgtaaagaaa aataagcaca    16740
agttttatcc ggcctttatt cacattcttg cccgcctgat gaatgctcat ccggaatttc    16800
gtatggcaat gaaagacggt gagctggtga tatgggatag tgttcaccct tgttacaccg    16860
ttttccatga gcaaactgaa acgttttcat cgctctggag tgaataccac gacgatttcc    16920
ggcagtttct acacatatat tcgcaagatg tggcgtgtta cggtgaaaac ctggcctatt    16980
tccctaaagg gtttattgag aatatgtttt tcgtctcagc caatccctgg gtgagtttca    17040
ccagttttga tttaaacgtg gccaatatgg acaacttctt cgcccccgtt ttcaccatgg    17100
gcaaatatta tacgcaaggc gacaaggtgc tgatgccgct ggcgattcag gttcatcatg    17160
ccgtttgtga tggcttccat gtcggcagaa tgcttaatga attacaacag tactgcgatg    17220
agtggcaggg cggggcgtaa ttttttttaag gcagttattg gtgcccttaa acgcctggtt    17280
gctacgcctg aataagtgat aataagcgga tgaatggcag aaattcgatg ataagctgtc    17340
aaacatgaga attggtcgac cctgtggaat gtgtgtcagt tagggtgtgg aaagtcccca    17400
ggctccccag caggcagaag tatgcaaagc atgcatctca attagtcagc aaccaggtgt    17460
ggaaagtccc caggctcccc agcaggcaga agtatgcaaa gcatgcatct caattagtca    17520
gcaaccatag tcccgcccct aactccgccc atcccgcccc taactccgcc cagttccgcc    17580
cattctccgc cccatggctg actaattttt tttatttatg cagaggccga ggccgcctc    17639
```

```
<210> SEQ ID NO 8
<211> LENGTH: 36
<212> TYPE: DNA
<213> ORGANISM: Artificial sequence
<220> FEATURE:
<223> OTHER INFORMATION: synthetic primer

<400> SEQUENCE: 8
atccaccggt ccacaaccat ggcctcctcc gaggac                                36

<210> SEQ ID NO 9
<211> LENGTH: 39
<212> TYPE: DNA
<213> ORGANISM: Artificial sequence
<220> FEATURE:
<223> OTHER INFORMATION: synthetic primer

<400> SEQUENCE: 9
tgatctagag tcgcggccgc tttaggcgcc ggtggagtg                             39

<210> SEQ ID NO 10
<211> LENGTH: 22
<212> TYPE: DNA
<213> ORGANISM: Artificial sequence
<220> FEATURE:
<223> OTHER INFORMATION: synthetic primer

<400> SEQUENCE: 10
agtggttttg tgtttgtcat cc                                               22

<210> SEQ ID NO 11
<211> LENGTH: 51
<212> TYPE: DNA
<213> ORGANISM: Artificial sequence
<220> FEATURE:
<223> OTHER INFORMATION: synthetic primer

<400> SEQUENCE: 11
```
ggatgacaaa cacaaaacca ctggccggca tggtcccagc ctcctcgctg g         51

<210> SEQ ID NO 12
<211> LENGTH: 46
<212> TYPE: DNA
<213> ORGANISM: Artificial sequence
<220> FEATURE:
<223> OTHER INFORMATION: synthetic primer

<400> SEQUENCE: 12
ggtcccagcc tcctcgctgg cgccggctgg gcaacattcc gagggg              46

<210> SEQ ID NO 13
<211> LENGTH: 47
<212> TYPE: DNA
<213> ORGANISM: Artificial sequence
<220> FEATURE:
<223> OTHER INFORMATION: synthetic primer

<400> SEQUENCE: 13
gtcccattcg ccattaccga ggggacggtc ccctcggaat gttgccc             47

<210> SEQ ID NO 14
<211> LENGTH: 60
<212> TYPE: DNA
<213> ORGANISM: Artificial sequence
<220> FEATURE:
<223> OTHER INFORMATION: synthetic primer

<400> SEQUENCE: 14
cccgggcggc cgcgcatacg atttaggtga cactatagag taaatcctgt gtgctaattg   60

<210> SEQ ID NO 15
<211> LENGTH: 40
<212> TYPE: DNA
<213> ORGANISM: Artificial sequence
<220> FEATURE:
<223> OTHER INFORMATION: synthetic primer

<400> SEQUENCE: 15
atgcatgcgg ccgcgtcgac ggtcgaaaaa agaaaaggag                     40

<210> SEQ ID NO 16
<211> LENGTH: 38
<212> TYPE: DNA
<213> ORGANISM: Artificial sequence
<220> FEATURE:
<223> OTHER INFORMATION: synthetic primer

<400> SEQUENCE: 16
atgcatgccg gcgaattctg aaccagtcct aaaacgag                       38

<210> SEQ ID NO 17
<211> LENGTH: 51
<212> TYPE: DNA
<213> ORGANISM: Artificial sequence
<220> FEATURE:
<223> OTHER INFORMATION: synthetic primer

<400> SEQUENCE: 17
cccgggcggc cgctaatacg actcactata gggagttgtt agtctacgtg g        51

<210> SEQ ID NO 18
<211> LENGTH: 17
<212> TYPE: DNA
<213> ORGANISM: Artificial sequence

```
<220> FEATURE:
<223> OTHER INFORMATION: synthetic primer

<400> SEQUENCE: 18
accccgcctc aatcctc                                                    17

<210> SEQ ID NO 19
<211> LENGTH: 27
<212> TYPE: DNA
<213> ORGANISM: Artificial sequence
<220> FEATURE:
<223> OTHER INFORMATION: synthetic primer

<400> SEQUENCE: 19
ggtttctggg acctcccacc ccagagt                                         27

<210> SEQ ID NO 20
<211> LENGTH: 17
<212> TYPE: DNA
<213> ORGANISM: Artificial sequence
<220> FEATURE:
<223> OTHER INFORMATION: synthetic primer

<400> SEQUENCE: 20
ctgtaggcac catcaat                                                    17

<210> SEQ ID NO 21
<211> LENGTH: 30
<212> TYPE: DNA
<213> ORGANISM: Artificial sequence
<220> FEATURE:
<223> OTHER INFORMATION: synthetic primer

<400> SEQUENCE: 21
gtcgacgcta gcgattgatg gtgcctacag                                      30

<210> SEQ ID NO 22
<211> LENGTH: 49
<212> TYPE: DNA
<213> ORGANISM: Artificial sequence
<220> FEATURE:
<223> OTHER INFORMATION: synthetic primer

<400> SEQUENCE: 22
ggaggctggg accatgccgg ccaggtcacc ggtagctctt gatccggca                 49

<210> SEQ ID NO 23
<211> LENGTH: 49
<212> TYPE: DNA
<213> ORGANISM: Artificial sequence
<220> FEATURE:
<223> OTHER INFORMATION: synthetic primer

<400> SEQUENCE: 23
tgccggatca agagctaccg gtgacctggc cggcatggtc ccagcctcc                 49

<210> SEQ ID NO 24
<211> LENGTH: 60
<212> TYPE: DNA
<213> ORGANISM: Artificial sequence
<220> FEATURE:
<223> OTHER INFORMATION: synthetic primer

<400> SEQUENCE: 24
ctccgcccag ttccgcccat tctccgcccc atggctgact aatttttttt atttatgcag    60
```

<210> SEQ ID NO 25
<211> LENGTH: 60
<212> TYPE: DNA
<213> ORGANISM: Artificial sequence
<220> FEATURE:
<223> OTHER INFORMATION: synthetic primer

<400> SEQUENCE: 25
gactaatttt ttttatttat gcagaggccg aggccgcctc agtaaatcct gtgtgctaat    60

<210> SEQ ID NO 26
<211> LENGTH: 60
<212> TYPE: DNA
<213> ORGANISM: Artificial sequence
<220> FEATURE:
<223> OTHER INFORMATION: synthetic primer

<400> SEQUENCE: 26
gactaatttt ttttatttat gcagaggccg aggccgcctc agttgttagt ctacgtggac    60

<210> SEQ ID NO 27
<211> LENGTH: 55
<212> TYPE: DNA
<213> ORGANISM: Artificial sequence
<220> FEATURE:
<223> OTHER INFORMATION: synthetic primer

<400> SEQUENCE: 27
ccctcggaat gttgcccagc cggcgccagc gaggaggctg ggaccatgcc ggcca    55

<210> SEQ ID NO 28
<211> LENGTH: 43
<212> TYPE: DNA
<213> ORGANISM: Artificial sequence
<220> FEATURE:
<223> OTHER INFORMATION: synthetic primer

<400> SEQUENCE: 28
gaggctggga ccatgccggc cagtggtttt gtgtttgtca tcc    43

<210> SEQ ID NO 29
<211> LENGTH: 45
<212> TYPE: DNA
<213> ORGANISM: Artificial sequence
<220> FEATURE:
<223> OTHER INFORMATION: synthetic primer

<400> SEQUENCE: 29
gaggctggga ccatgccggc cagaacctgt tgattcaaca gcacc    45

<210> SEQ ID NO 30
<211> LENGTH: 60
<212> TYPE: DNA
<213> ORGANISM: Artificial sequence
<220> FEATURE:
<223> OTHER INFORMATION: synthetic primer

<400> SEQUENCE: 30
cgaggaggct gggaccatgc cggccaggtc accgtttaaa cggccgaggc ggcctcggcc    60

<210> SEQ ID NO 31
<211> LENGTH: 60
<212> TYPE: DNA
<213> ORGANISM: Artificial sequence
<220> FEATURE:
<223> OTHER INFORMATION: synthetic primer

<400> SEQUENCE: 31
tttatgcaga ggccgaggcc gcctcggccg tttaaacggt gacctggccg gcatggtccc    60

<210> SEQ ID NO 32
<211> LENGTH: 21
<212> TYPE: DNA
<213> ORGANISM: Artificial sequence
<220> FEATURE:
<223> OTHER INFORMATION: synthetic primer

<400> SEQUENCE: 32
gaggcggcct cggcctctgc a    21

<210> SEQ ID NO 33
<211> LENGTH: 21
<212> TYPE: DNA
<213> ORGANISM: Artificial sequence
<220> FEATURE:
<223> OTHER INFORMATION: synthetic primer

<400> SEQUENCE: 33
tggccggcat ggtcccagcc t    21

<210> SEQ ID NO 34
<211> LENGTH: 60
<212> TYPE: DNA
<213> ORGANISM: Artificial sequence
<220> FEATURE:
<223> OTHER INFORMATION: synthetic primer

<400> SEQUENCE: 34
gactaatttt ttttatttat gcagaggccg aggccgcctc agttgttagt ctgtgtggac    60

<210> SEQ ID NO 35
<211> LENGTH: 45
<212> TYPE: DNA
<213> ORGANISM: Artificial sequence
<220> FEATURE:
<223> OTHER INFORMATION: synthetic primer

<400> SEQUENCE: 35
gaggctggga ccatgccggc cagaacctgt tggatcaaca acacc    45

<210> SEQ ID NO 36
<211> LENGTH: 36
<212> TYPE: DNA
<213> ORGANISM: Artificial sequence
<220> FEATURE:
<223> OTHER INFORMATION: synthetic primer

<400> SEQUENCE: 36
ttatgcatag tcaggcacgt catatggata ggatcc    36

<210> SEQ ID NO 37
<211> LENGTH: 44
<212> TYPE: DNA
<213> ORGANISM: Artificial sequence
<220> FEATURE:
<223> OTHER INFORMATION: synthetic primer

<400> SEQUENCE: 37
tcgactaata cgactcacta tagggggagc gcgaatggaa aaac    44

<210> SEQ ID NO 38

```
<211> LENGTH: 47
<212> TYPE: DNA
<213> ORGANISM: Artificial sequence
<220> FEATURE:
<223> OTHER INFORMATION: synthetic primer

<400> SEQUENCE: 38
cgcgcatacg atttaggtga cactataggt atcaagaact ctcacgg          47

<210> SEQ ID NO 39
<211> LENGTH: 21
<212> TYPE: DNA
<213> ORGANISM: Artificial sequence
<220> FEATURE:
<223> OTHER INFORMATION: synthetic primer

<400> SEQUENCE: 39
agtaaatcct gtgtgctaat t                                       21

<210> SEQ ID NO 40
<211> LENGTH: 20
<212> TYPE: DNA
<213> ORGANISM: Artificial sequence
<220> FEATURE:
<223> OTHER INFORMATION: synthetic primer

<400> SEQUENCE: 40
ggcaatcacg actcgttgcg                                         20

<210> SEQ ID NO 41
<211> LENGTH: 23
<212> TYPE: DNA
<213> ORGANISM: Artificial sequence
<220> FEATURE:
<223> OTHER INFORMATION: synthetic primer

<400> SEQUENCE: 41
agatggtatc ttcatattta gag                                     23

<210> SEQ ID NO 42
<211> LENGTH: 22
<212> TYPE: DNA
<213> ORGANISM: Artificial sequence
<220> FEATURE:
<223> OTHER INFORMATION: synthetic primer

<400> SEQUENCE: 42
acatttgctt tggtccctgt ct                                      22

<210> SEQ ID NO 43
<211> LENGTH: 60
<212> TYPE: DNA
<213> ORGANISM: Artificial sequence
<220> FEATURE:
<223> OTHER INFORMATION: synthetic primer

<400> SEQUENCE: 43
ctccgcccag ttccgcccat tctccgcccc atggctgact aatttttttt atttatgcag    60

<210> SEQ ID NO 44
<211> LENGTH: 58
<212> TYPE: DNA
<213> ORGANISM: Artificial sequence
<220> FEATURE:
<223> OTHER INFORMATION: synthetic primer

<400> SEQUENCE: 44
```

```
gactaatttt ttttatttat gcagaggccg aggccgcctc ttaaaacagc ggatgggt      58
```

<210> SEQ ID NO 45
<211> LENGTH: 60
<212> TYPE: DNA
<213> ORGANISM: Artificial sequence
<220> FEATURE:
<223> OTHER INFORMATION: synthetic primer

<400> SEQUENCE: 45

```
gaggctggga ccatgccggc cttttttttt tttttttttt tttttttttt tataaactcc    60
```

<210> SEQ ID NO 46
<211> LENGTH: 58
<212> TYPE: DNA
<213> ORGANISM: Artificial sequence
<220> FEATURE:
<223> OTHER INFORMATION: synthetic primer

<400> SEQUENCE: 46

```
gactaatttt ttttatttat gcagaggccg aggccgcctc ttaaaacagc ctgtgggt      58
```

<210> SEQ ID NO 47
<211> LENGTH: 60
<212> TYPE: DNA
<213> ORGANISM: Artificial sequence
<220> FEATURE:
<223> OTHER INFORMATION: synthetic primer

<400> SEQUENCE: 47

```
gaggctggga ccatgccggc cttttttttt tttttttttt tttttttttt tgctattctg    60
```

<210> SEQ ID NO 48
<211> LENGTH: 54
<212> TYPE: DNA
<213> ORGANISM: Artificial sequence
<220> FEATURE:
<223> OTHER INFORMATION: synthetic primer

<400> SEQUENCE: 48

```
ccctcggaat gttgcccagc cggcgccagc gaggaggctg ggaccatgcc ggcc           54
```

<210> SEQ ID NO 49
<211> LENGTH: 48
<212> TYPE: DNA
<213> ORGANISM: Artificial sequence
<220> FEATURE:
<223> OTHER INFORMATION: synthetic primer

<400> SEQUENCE: 49

```
agaggccgag gccgcctcgg ccgtttaaac ggtgacctgg ccggcatg                 48
```

<210> SEQ ID NO 50
<211> LENGTH: 19
<212> TYPE: DNA
<213> ORGANISM: Artificial sequence
<220> FEATURE:
<223> OTHER INFORMATION: synthetic primer

<400> SEQUENCE: 50

```
cggatatcag taaatcctg                                                 19
```

<210> SEQ ID NO 51
<211> LENGTH: 19
<212> TYPE: DNA

```
<213> ORGANISM: Artificial sequence
<220> FEATURE:
<223> OTHER INFORMATION: synthetic primer

<400> SEQUENCE: 51
cacaaaacca ctctgtagg                                              19
```

BACTERIAL ARTIFICIAL CHROMOSOMES

REFERENCE TO SEQUENCE LISTING
SUBMITTED VIA EFS-WEB

This application includes an electronically submitted sequence listing in .txt format. The .txt file contains a sequence listing entitled "2016-03-24 19893.9 ST25.txt" created on Mar. 24, 2016 and is 129,679 bytes in size. The sequence listing contained in this .txt file is part of the specification and is hereby incorporated by reference herein in its entirety.

FIELD OF THE INVENTION

The present invention relates to a plasmid vector system suitable for manipulating, maintaining and propagating infectious cDNA of RNA virus genomes as well as to the use of such vector systems.

BACKGROUND OF THE INVENTION

Previously, copy DNA (cDNA) of several flaviviruses and other RNA viruses has been cloned in different low copy bacterial vectors to overcome their intrinsic toxicity (due to the large size and cryptic expression of the viral sequences) (Bredenbeek et al. (2003) *J. Gen. Virol.* 84, 1261-1268; Durbin, et al. (2006) *Hum Vaccin.* 2, 255-260; Fan and Bird (2008) *J. Virol. Methods.* 149, 309-315; Li et al. (2011) *PLoS One* 6, e18197; Pu et al. (2011) *J. Virol.* 85, 2927-2941; Rice et al. (1989) *New Biol.* 1, 285-296) Almazán et al. (2008) *Methods Mol Biol.* 454, 275-91). The cloned cDNAs have been used as templates for production of infectious recombinant viruses, either by in vitro synthesis and transfection of the RNA genomes (Bredenbeek et al., 2003, cited above), or by incorporating the viral cDNA in an expression cassette, which comprise a promoter such as the CMV-IE (Cytomegalovirus Immediate Early) promoter allowing the transcription of the viral RNA from transfected plasmid DNAs (Enjuanes et al. (2001) *J. Biotechnol.* 88, 183-204; Hall et al. (2003) *Proc. Natl. Acad. Sci. USA.* 100, 10460-10464). Such viral expression cassettes directing the expression of attenuated foot-and-mouth disease (Ward et al. (1997) *J. Virol.* 71, 7442-7447) and Kunjin viruses (Hall et al. (2003) *Proc Natl Acad Sci USA.* 100, 10460-10464) have been used as experimental DNA vaccines. Although the low copy number vector systems comprising a viral expression cassette can be maintained in the bacterial host cell in a stable manner, they have the important disadvantage that they only allow the purification of infective viral cDNA in amounts that are merely sufficient for small scale experimental use. Therefore, their use as a routine source of infective viral cDNA is impossible, for instance in the production of a life cDNA vaccine.

The production of viral DNA vaccines requires a substantial amplification of cloning vectors to obtain sufficient DNA, but these amplification methods are subject to severe constraints. In order to avoid mutations, vectors comprising viral DNA are propagated under conditions which prevent mutagenic events (recombination, mutations, improving mismatch repair, and the like). Bacterial Artificial Chromosomes (BAC) are known for their stability and can contain inserts up to 500 kb or more.

However the size of such a vector with foreign DNA is a serious burden for bacteria, and its replication requires a substantial metabolic effort. Furthermore, exhaustion of nucleotides can lead to increased mutations. Finally, unwanted expression of foreign DNA (so-called cryptic expression) may occur, which can lead to toxic recombinant proteins. The production of toxic proteins by cryptic transcripts is inherent to flavivirus DNA and can only be solved by lowering the copy number of plasmids. Indeed, the higher the copy number of a vector, the higher the concentration of toxic proteins. As a consequence, bacterial hosts may counterselect for mutants wherein these proteins are not expressed.

Pu et al. (2011) *J. Virol.* 85, 2927-2941, describes in detail various attempts to solve the intrinsic toxicity of flavivirus cDNA in bacteria. These include the in vivo ligation of plasmids comprising parts of the viral genome, specific hosts, mutants to avoid cryptic expression and also low copy number plasmids.

The use of BACs which occur as a single copy in a bacterium provides thus a solution for these problems.

The low copy number is not a drawback for those applications wherein BAC DNA is subsequently subcloned or amplified to increase the concentration and wherein the introduction of some mutations by these techniques is not critical for the envisaged experiments. However, such amplification methods cannot be applied in the manufacture of DNA vaccines, making BACs a non-preferred vehicle for large scale plasmid preparations for DNA vaccines. Very large scale cultures are required to obtain substantial amounts of BAC.

The use of inducible BAC vectors is known from Wild et al. (2002) *Genome Res.* 12, 1434-1444 whereby the copy number of the BAC increases from 1 copy per cell to up to 100 copies per cell, or even more. Although this system provides a method to increase the yield of BAC DNA, there is a legitimate concern that the strongly increased activity of the replication system upon induction will increase the mutation frequency. The manufacture of DNA vaccines thus requires a system wherein a high copy number of a vector is obtained, but wherein replication of the vectors occurs without intolerable introduction of mutations.

SUMMARY OF THE INVENTION

The present invention resolves the problem of the amplification of viral cDNA for the preparation of a vaccine in the vector systems of the prior art by providing a vector that can be stably maintained in the host cell at low copy number, but can be significantly amplified by modifying the culture conditions of its host, without unwanted mutagenesis events. It is a further object of the present invention to provide such vector that can be shuttled from and to both a yeast and bacterial host, thus providing a very versatile system amenable to manipulate the vector in both a yeast and bacterial genetic system.

The present invention demonstrates, against what was expected, that the inducible increase in copy number of a BAC vector provides DNA which has a surprisingly low mutation rate. Even more surprisingly, the few mutations that occur are mostly frameshift mutations or stop codons, leading to truncated versions upon expression. Point mutations, which are either without effect or which lead to modified amino acids, are underrepresented.

This unexpected effect leads to the advantageous effect that high amounts of vector are obtained and that the limited amount of errors that does occur leads to a non-functional viral genome, rather than to a mutated viral genome of which the virulence can be increased compared to originally cloned construct.

The present invention provides a bacterial artificial chromosome comprising an inducible bacterial ori sequence, which allows to induce the amplification of said bacterial artificial chromosome to a high copy number, for instance by modifying the culture conditions of the bacterial host. Bacterial artificial chromosomes as used herein further comprise a viral expression cassette comprising a cDNA of a RNA virus genome flanked by cis-regulatory elements, which upon introduction of said bacterial artificial chromosome in a mammalian cell promote the transcription of said viral cDNA and allow for the processing of the transcribed RNA into infectious viral RNA. Viral cDNA contained in the viral expression cassette can either correspond to that of a wild-type RNA virus genome or be a chimeric viral cDNA construct, wherein heterologous DNA sequences have been inserted and/or native viral sequences have been deleted, truncated, or mutated. Typically heterologous DNA sequences encode one or more peptides/proteins, which are heterologously expressed by the recombinant virus, following the introduction in a mammalian cell of a bacterial artificial chromosome according to the present invention that contains a viral expression cassette comprising such chimeric viral cDNA. The bacterial artificial chromosome can further comprise a yeast autonomously replicating sequence for shuttling to and maintaining said bacterial artificial chromosome in yeast. The possibility to shuttle to and maintain the bacterial artificial chromosome according to the present invention in a yeast cell provides the advantage that it is amenable for genetic manipulation in both the yeast and bacterial genetic systems. As such the present invention provides a single vector system suitable for manipulating, maintaining and propagating infectious cDNA of RNA virus genomes.

In absence of a stimulus of the inducible ori, the bacterial artificial chromosomes according to the present invention can be used for archiving and stable cloning of infectious viral cDNA in a bacterial host, while in presence of such stimulus said cDNA can readily be amplified and subsequently isolated to be used. The bacterial artificial chromosomes according to the present invention are particularly useful in the development, stable maintenance and production of viral cDNA to be used as a life vaccine against RNA viral pathogens. Alternatively, said bacterial artificial chromosomes are used for the maintenance and propagation of native or recombinant viruses from cDNA, for instance for research purposes.

In the present invention, BACs with an inducible bacterial ori are used for the preparation of a vaccine of a viral expression cassette comprising cDNA of an RNA virus and cis regulatory elements for the transcription of viral cDNA in mammalian cells and processing of the transcribed RNA into infectious viral RNA.

Surprisingly, the generation of multiple copies of the BAC comprising the viral DNA did not lead to the disadvantages that are known to occur with high copy number systems.

Generally, toxic proteins are produced in bacterial systems, due to the cryptic expression of viral sequences. Indeed, the generation of flavivirus infectious clones has been traditionally hindered by the toxicity of their full-length cDNAs in bacteria. Various approaches have been employed to overcome this problem, including the use of very-low-copy-number plasmids and bacterial artificial chromosomes (discussed in *Edmonds* (2013) *J. Virol.* 87, 2367-2372). This is a phenomenon which relates to the insert which is cloned into the BAC, and hampers bacterial growth and metabolism. Bacteria with mutants wherein cryptic expression does not take place have a growth advantage and will overgrow the original population. In the prior art this is reflected by the size of bacterial colonies. Non-mutated constructs produce toxic proteins and typically small colonies are obtained. Mutated constructs produce less or no toxic proteins which results in the occurrence of larger colonies.

Based upon this prior art knowledge it was expected that the induction of plasmid replication would thus result in an increase of toxic transcripts and a concomitant increase in mutants wherein cryptic expression does not take place.

Surprisingly the inducible replication system appears to be insensitive to the toxicity of cryptic proteins. Indeed, compared to the prior art high copy number systems, the bacterial colonies are somewhat larger, which indicates that the bacterial host is less sensitive to eventual toxic proteins. More importantly, very large colonies, representing mutated plasmids are not encountered.

The finding that the inducible system is insensitive towards toxic proteins is unexpected. There were no indications in the prior art which indicated that this system would not be sensitive to toxic proteins (or perhaps that toxic proteins are not produced).

A further disadvantage of the inducible system is inherent to the generation of multiple copies of the BAC. Indeed the authors of the inducible system explain that the most important feature of BAC clones is their stability resulting from their very low copy number. Wild et al. (2002) cited above shows that the copy number can be lowered even further by the addition of glucose. This single copy state improves stability of maintenance of BAC libraries by reducing the opportunity for intracellular recombination between clones. This demonstrates that the inducible system as published by Wild et al. does not lower the changes of unwanted recombination events which occur as soon as multiple copies of a BAC are present in a host cell. It is understood by the skilled person that induction and the subsequent high copy number will reintroduce recombination events. Consequently, the skilled person would refrain of using such systems for DNA preparations that are intended to be used for vaccination purposes.

In the present invention BACs have been amplified in the inducible on system and the amplified BAC has been tested for recombination events. Contrary to what would be expected, recombination events are rare.

Furthermore, apart from testing for recombination events, the amplifies BACs have been tested as well for the presence of other mutations. The mutation frequency which was encountered was very low, and moreover, the fraction of missense is surprisingly lower than theoretically expected. Mutations, if occurring are predominantly nonsense or frameshift mutations leading to non-functional viral RNA.

The present invention allows a significant upscale of DNA vaccine production. For example, the main manufacturers of the life-attenuated Yellow Fever vaccine are at present unable to meet the existing demands. With the technology of the present invention, it will be possible to produce DNA vaccines at significant lower costs and higher quantities than the current life-attenuated vaccine, thereby fulfilling a long felt need.

Also for other viral diseases such as JEV, WNV, measles, rubella and HIV vaccines there is a need for a vaccine preparation platform which can provide sufficient amounts of DNA.

A first aspect of the invention relates to uses of a bacterial artificial chromosome (BAC) for the preparation of a vaccine, wherein the BAC comprises:

an inducible bacterial ori sequence for amplification of said BAC to more than 10 copies per bacterial cell, and a viral expression cassette comprising a cDNA of an attenuated RNA virus genome and comprising cis-regulatory elements for transcription of said viral cDNA in mammalian cells and for processing of the transcribed RNA into infectious RNA virus.

Embodiments of cDNAs of an attenuated RNA virus genome are a chimeric viral cDNA construct of an RNA virus genome, wherein a heterologous DNA sequence has been inserted or wherein a native viral sequence has been deleted, truncated, or mutated.

Embodiments of the viral expression cassette comprise
a cDNA of a positive-strand RNA virus genome,
a RNA polymerase driven promoter preceding the 5' end of said cDNA for initiating the transcription of said cDNA, and
an element for RNA self-cleaving following the 3' end of said cDNA for cleaving the RNA transcript of said viral cDNA at a set position.

Embodiments of positive-strand RNA virus are flaviviruses, hepaciviruses, pestiviruses, togaviruses, picornaviruses, coronaviruses, hepeviruses, and caliciviruses.

In a typical embodiment the viral expression cassette comprises a cDNA of a yellow fever virus, for example a cDNA of the life-attenuated YFV-17D yellow fever virus vaccine.

In other embodiments the viral expression cassette comprises a cDNA of a virus belonging to the group of negative-strand RNA viruses, double-strand RNA viruses or ambisense RNA viruses.

In specific embodiments the bacterial artificial chromosome further comprises a yeast autonomously replicating sequence for shuttling to and maintaining said bacterial artificial chromosome in yeast.

An example of a yeast on sequence is the 2µ plasmid origin or the ARS1 (autonomously replicating sequence 1) or functionally homologous derivatives thereof.

In certain embodiments the RNA polymerase driven promoter is an RNA polymerase II promoter, such as Cytomegalovirus Immediate Early (CMV-IE) promoter, the Simian virus 40 promoter or functionally homologous derivatives thereof.

In other embodiments the RNA polymerase driven promoter is an RNA polymerase I or III promoter.

Examples of an element for RNA self-cleaving is the cDNA of the genomic ribozyme of hepatitis delta virus or functionally homologous RNA elements.

In a particular embodiment the viral expression cassette comprises a cDNA of the life-attenuated YFV-17D vaccine, wherein one or more of the cDNA sequences coding for the virion surface proteins are either deleted, truncated, or mutated so that such functional virion surface protein of YFV-17D is not expressed and wherein a cDNA sequences coding for a heterologous protein is inserted in the YFV-17D cDNA. An example of such heterologous protein is a virion surface protein of a flavivirus.

Embodiments of a viral expression cassette comprises a cDNA of the life-attenuated YFV-17D vaccine, wherein one or more unrelated cDNA sequences are inserted to be expressed as one or more heterologous protein within the viral polyprotein.

In other embodiments the viral expression cassette comprises a viral cDNA wherein foreign cDNA sequences are inserted to be heterologously expressed by the said recombinant viruses.

A further aspect relates to methods of preparing a vaccine against RNA viruses comprising the steps of: a) providing a bacterial host transfected with a BAC as described in the first aspect and in the various embodiments thereof b) amplifying the BAC by adding a compound which activates said inducible on c) isolating the amplified BAC,
d) formulating the BAC into a vaccine.

A further aspect relates to a BAC as described in the first aspect and in the various embodiments thereof for use as a vaccine.

Another aspect of the present invention relates to a BAC as described in the first aspect and in the various embodiments thereof for use in the prevention of a RNA virus infection.

A further aspect relates to uses of a BAC as described in the first aspect and in the various embodiments thereof as a life DNA vaccine.

Another aspect relates to uses of a BAC as described in the first aspect and in the various embodiments thereof for the propagation of native or recombinant viruses from said cDNA.

A further aspect relates bacterial artificial chromosome (BAC) as a BAC as described in the first aspect and in the various embodiments thereof for the preparation of a vaccine.

DETAILED DESCRIPTION OF THE INVENTION

Legends to the Figures

FIG. 1. Generation of the pShuttleBAC series of RNA virus expression plasmids. (A) Sketch showing the construction of the pShuttleBAC/Pme as starting vector construct. (B) Sketch showing the construction of the pShuttleBAC/Pme derived flaviviral expression vectors by insertion of the viral cDNAs by homologous recombination between the SV40 promoter (SV40p) and HDV ribozyme (HDrz).

Figure 2:
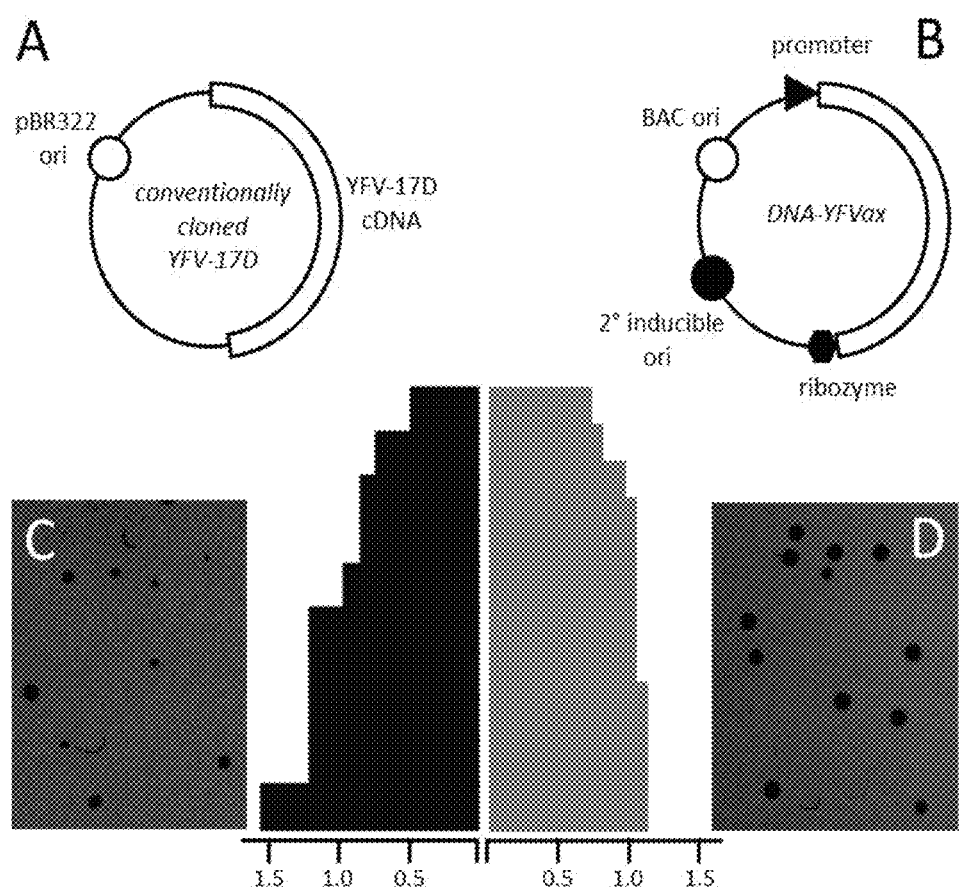

FIG. 2. Enhanced plasmid stability of pShuttleBAC constructs in *E. coli*. Generic plasmid maps showing the principle layout of prior art flaviviral cDNA plasmids (A) and the new pShuttleBAC series of vectors (B, DNA-YFVax). Upon transformation in *E. coli* a single colony of each (A) and (B) was grown overnight at 37° C. and plated on selective media. Generally constructs of type A grow into much smaller colony sizes as those of type B (FIGS. 2C and D, respectively). Moreover, type A constructs give rise to progeny of a wide range of colony sizes (histogram for normalized colony diameters, right panel of FIG. 2C) indicative for selection and segregation of mutant plasmid clones that occasionally render the cDNAs less toxic to *E. coli*. Clonal analysis identified multiple possible underlying mutations, including transposon insertion in the viral E/NS1 region. By contrast, plasmid clones comprising type B constructs of the pShuttleBAC series do not segregate and show a more homogenous colony size even after repeated passage in *E. coli* indicating high genetic stability.

Figure 3:
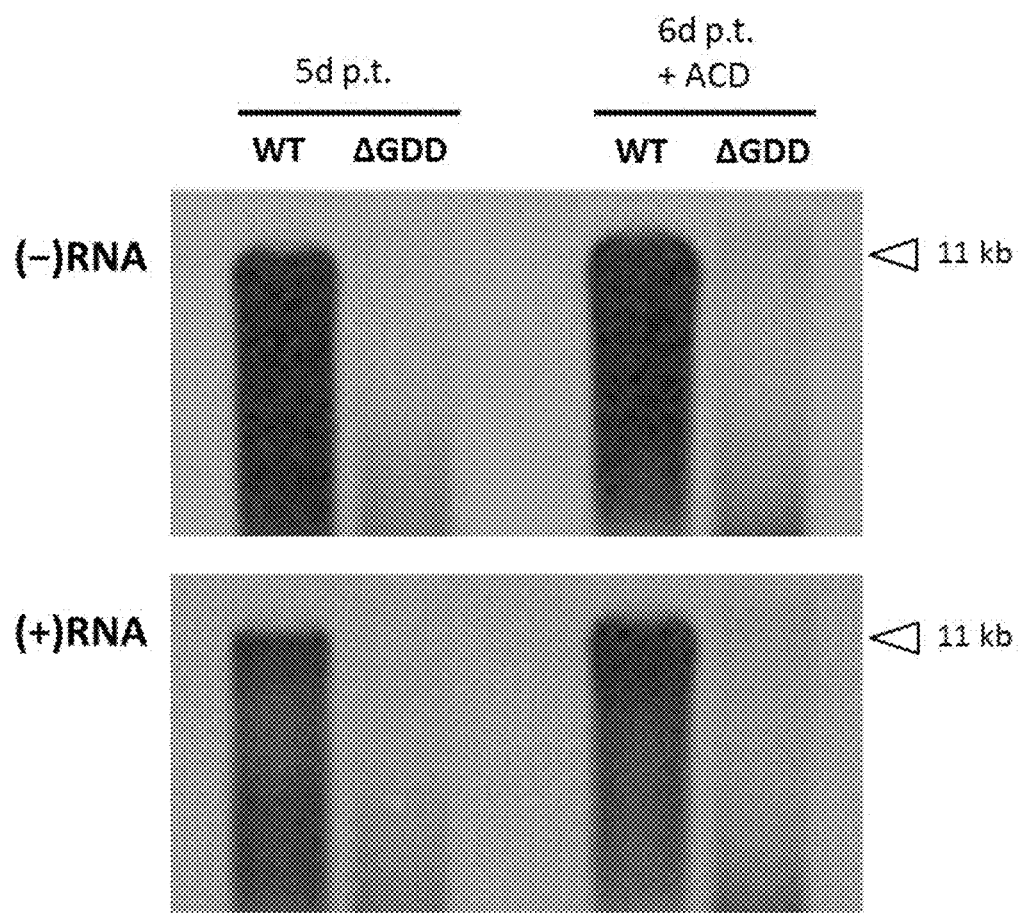

FIG. 3A. Detection of replicative intermediates of YFV-17D RNA replication after transfection of Vero-B cells with pShuttle/YF17D (wildtype, WT) and its replication deficient derivative pShuttle/YF17DΔGDD (ΔGDD) by Northern blot. Antisense oriented antigenomes, (−)-RNA (A upper panel, 11 kb) and sense orientated viral genomes, (+)-RNA (A lower panel, 11 kb), could be detected 5 days after transfection only in WT transfected cells. Ongoing replication in the presence of actinomycin D (ACD), an inhibitor of DNA directed RNA synthesis, confirms that after initial launching of YFV-17D genome transcription from pShuttle/YF17D, viral replication continues autonomously in a plasmid independent manner.

Figure 3B:
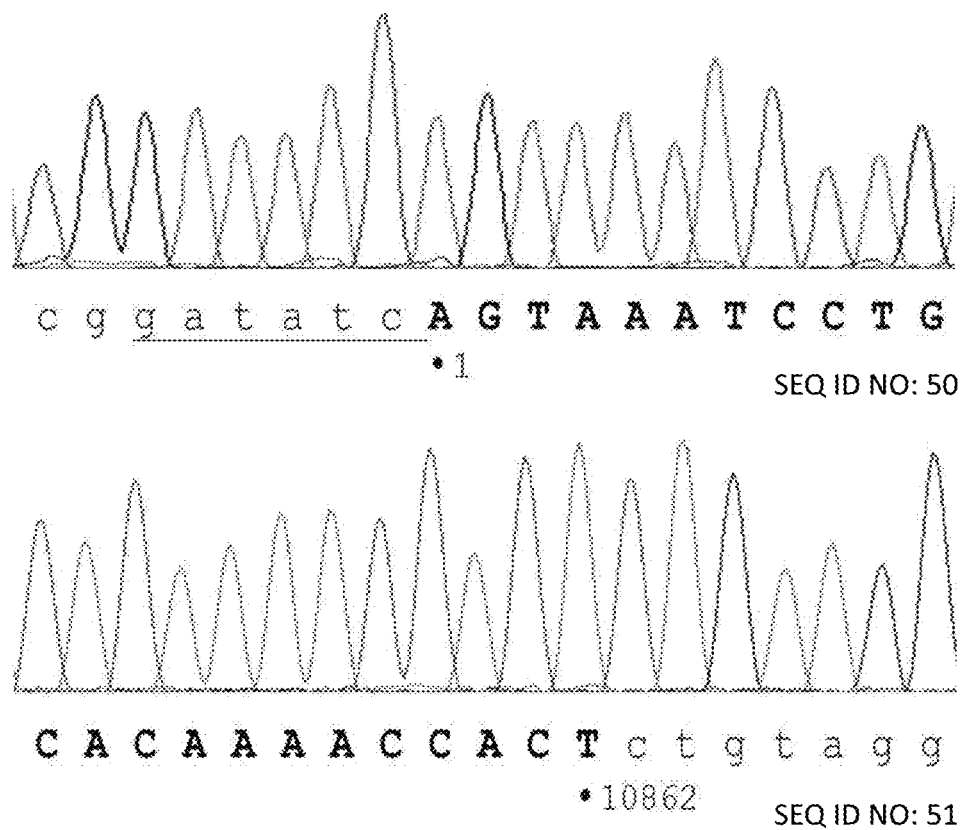

FIG. 3B. Detection of proper YFV-17D RNA transcript processing by 5'- and 3'-RACE (rapid amplification of cDNA ends). pShuttle/YF17D launches transcription of nascent YFV-17D RNAs (bold cases in FIG. 3B) that start and end with proper 5' and 3' ends (upper and lower panel, respectively) as confirmed by rapid amplification of cDNA ends (RACE).

Figure 4:
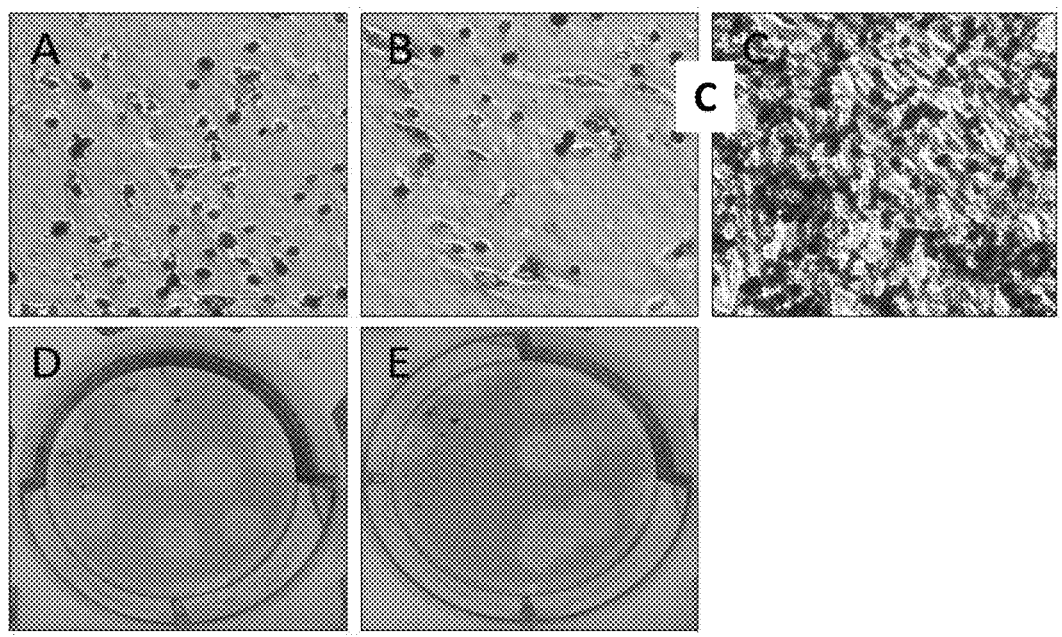

FIG. 4A-C. Similar CPE induced by YFV-17D of different origin. YFV-17D viruses derived from in vitro transcribed and capped RNA using pACNR-FLYF17DII as a template (A) or harvested after plasmid DNA transfection of pShuttle/YF17D (B) produce an identical virus induced cytopathic effect (CPE) on BHK-21 cells 5 days post infection (d p.i.); C, uninfected cells for comparison.

FIG. 4D-E. Similar plaque phenotype of YFV-17D of different origin. YFV-17D viruses derived from in vitro transcribed and capped RNA using pACNR-FLYF17DII as a template (D) or harvested after plasmid DNA transfection of pShuttle/YF17D (E) produce a comparable number (5 days p.i. $3 \times 10^5$ plaque forming units (pfu) $mL^{-1}$ vs $2 \times 10^5$ pfu $mL^{-1}$) and identical morphology of plaques (diameter 6.4±0.7 mM vs 6.1±1.1 mM; n=8, p-value=0.6 by t-test) on BHK-21 cells.

Figure 5:
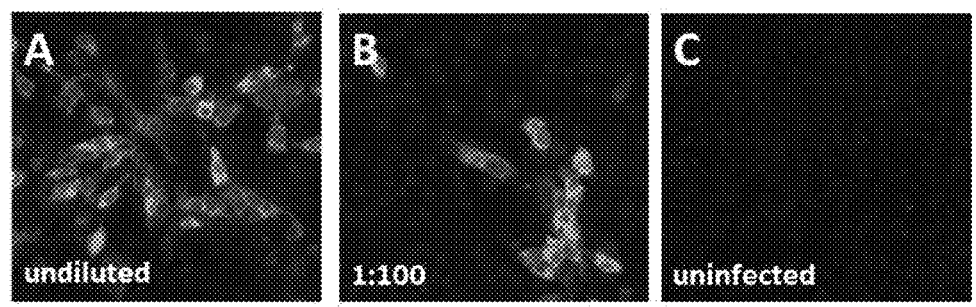

FIG. 5. Detection of infectious recombinant DENV2 by immunofluorescence assay (IFA). Recombinant DENV2 NGC produced by BHK-21 cells transfected with pShuttle/DV2 shows dose dependent infection of Vero-B cells, visualizes as viral foci by immunofluorescence staining for the viral E protein 5 days p.i. (A, undiluted supernatant, B, 100-fold diluted supernatant, C, uninfected cell control).

Figure 6:
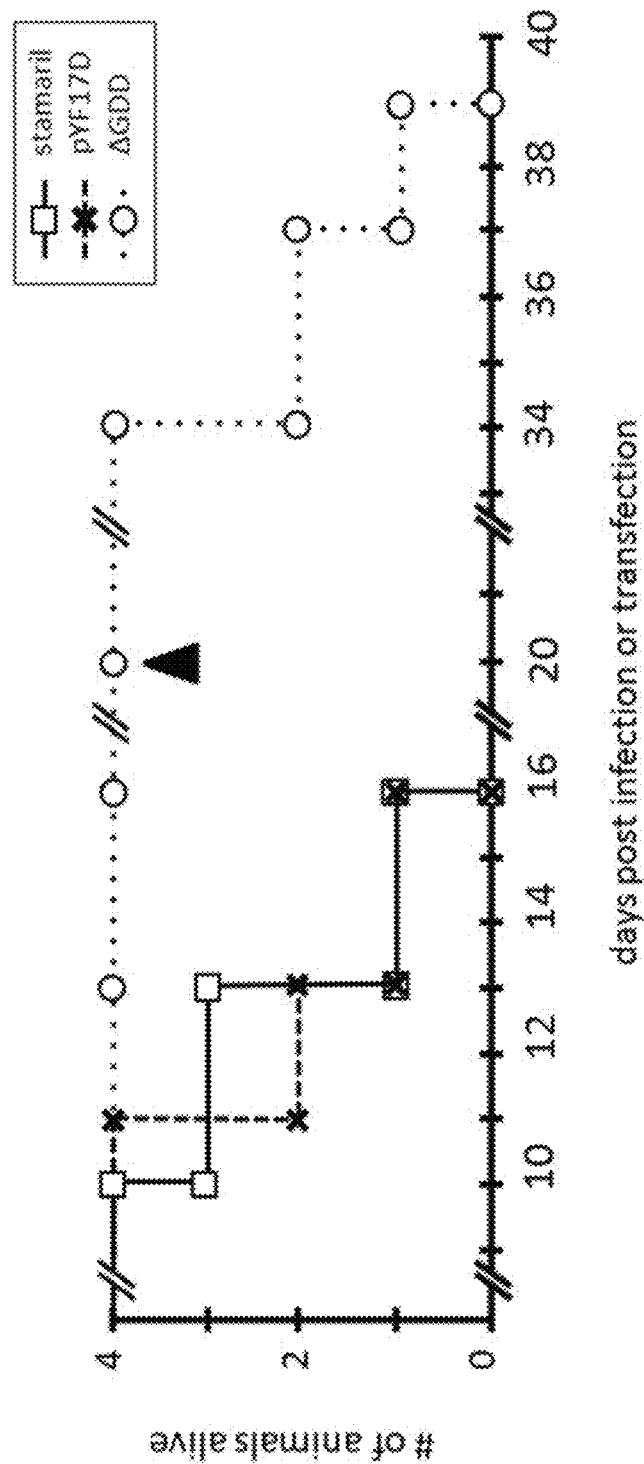

FIG. 6. Survival of AG129 mice infected with Stamaril (open squares) or transfected with pShuttle/YF17D (crosses). About 10 to 12 days after i.p. challenge, interferon type I and II receptor deficient (AG129) mice start losing weight and develop a uniform set of symptoms, namely ruffling of the fur, tremor and flaccid hind limb paralysis. Control animals transfected with the replication deficient NS5ΔGDD plasmid variant (ΔGDD, open circles) show no pathogenesis. However, they stay susceptible to a second Stamaril® challenge (filled triangle) 20 days after initial transfection and then die within a comparable timeframe and showing similar symptoms. Plasmid DNAs were transfected i.p. using calcium carbonate microflowers in 33% propylene glycol as carrier.

Figure 7:
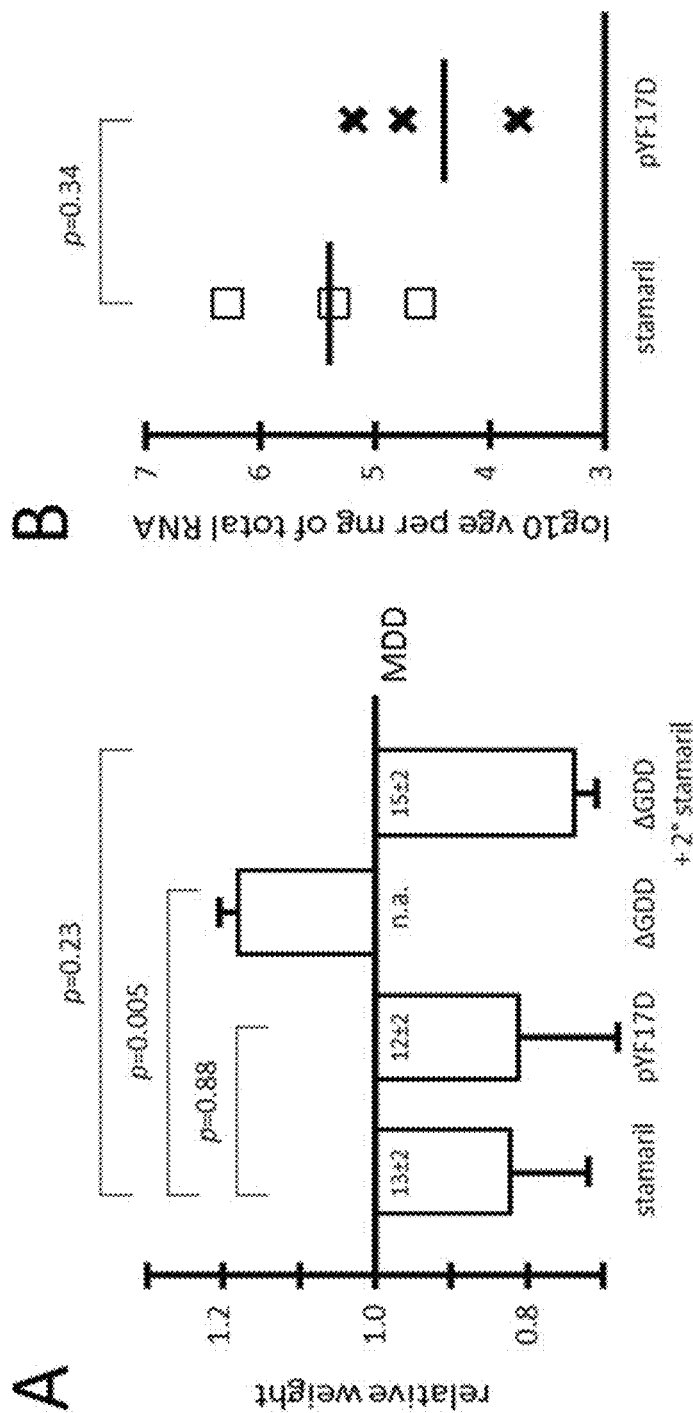

FIG. 7. Morbidity (A) and detection of YFV-17D RNA (B) from infected AG129 mice. (A) If infected either with Stamaril® or transfected with pShuttle/YF17D (pYF17D), AG129 mice loose about 20% of body weight before they have to be euthanized after an average of 12 to 13 days (MDD, mean day to death). By contrast, pShuttle/YF17DΔGDD (ΔGDD) transfected mice gain weight, before they are challenged with Stamaril® (ΔGDD+2° Stamaril) and die from YFV-17D infection within about two weeks. (B) Comparable amounts of YFV-17D RNA can be detected by means of qRT-PCR in brain samples of AG129 mice from (A) collected at death.

Figure 8:
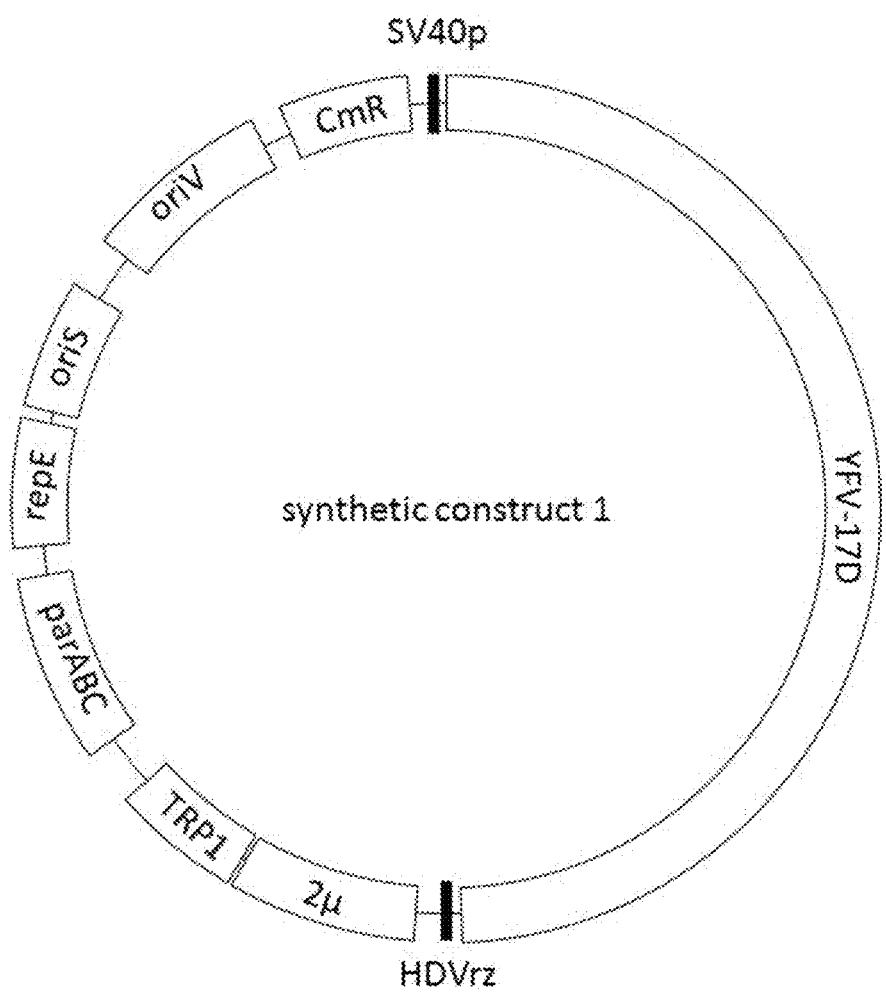

FIG. 8. Map of pShuttle/YF17D (synthetic construct #1). Legend: SV40p: Simian virus 40 promoter/origin, YFV-17D: yellow fever virus vaccine strain 17D cDNA, HDVrz: hepatitis delta virus ribozyme cDNA; 2μ: S. cerevisiae 2-micron origin; TRP1: TRP1 gene conferring prototrophic growth towards tryptophan; parABC: partitioning genes of F-plasmid; repE: repE gene of F-plasmid; oriS: origin of F-plasmid; oriV: origin of plasmid RK2; CmR: chloramphenicol resistance gene.

Figure 9:
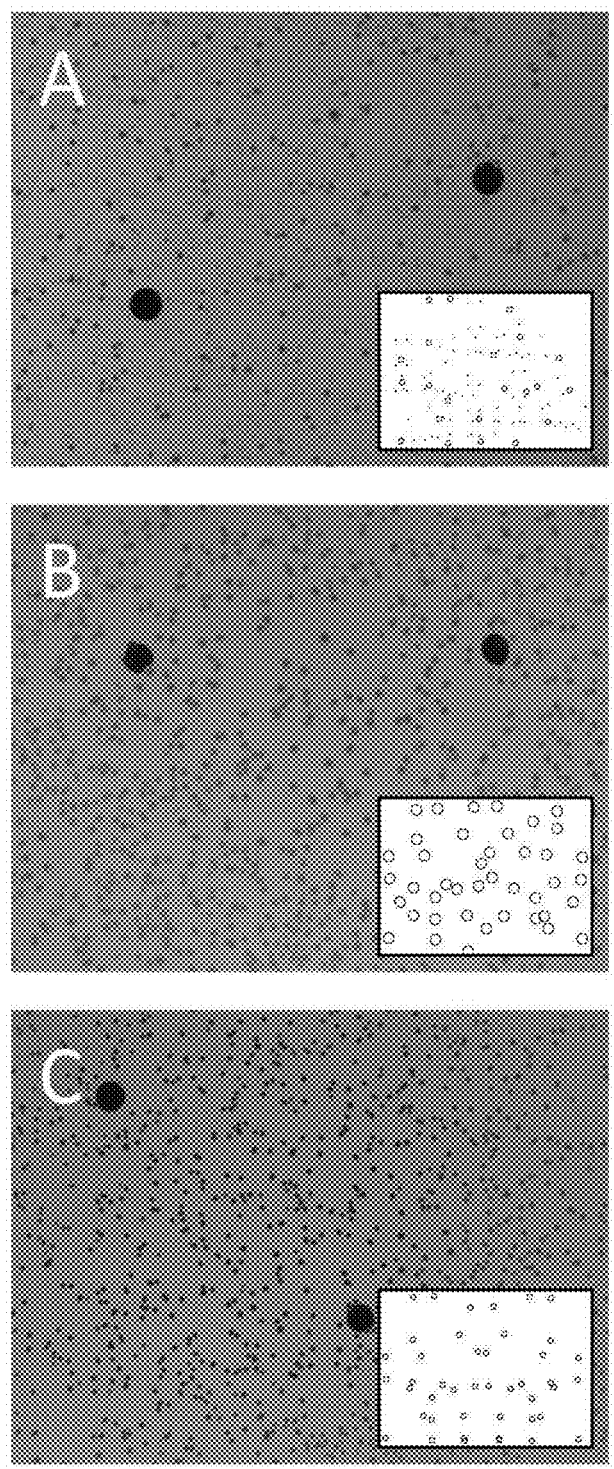

FIG. 9. E. coli colony growth after tranformation with different YFV-17D cDNA vectors. (A) E. coli EPI-300T colonies after transformation with pACNR-FLYF17DII and growth for 16 h at 37° C. A colony size distribution with two subpopulations with major size differences can be observed, microcolonies (diameter smaller than 0.2 mm) and macrocolonies (diameter around 0.4 mm). Microcolonies represent the majority. (B+C) E. coli EPI-300T colonies after transformation with pShuttle/YFV17D. Plating on plates without inducer (B), or with 0.01% L-arabinose (C) for induction of of high copy replication mediated by the inducible high-copy origin. Large black circles are zirkonia beads of 2.5 mm diameter embedded into the agar to serve as calibrators. Inset figures are schematic line drawings representing the colony outlines observed in each setting.

Figure 10:
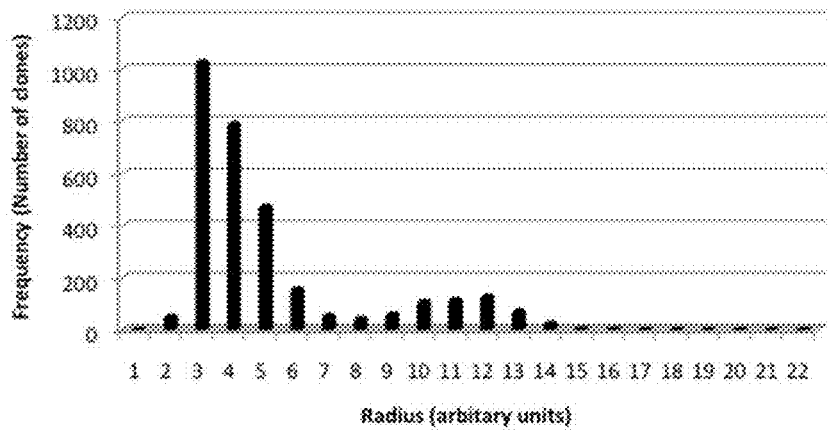
Figure 10:
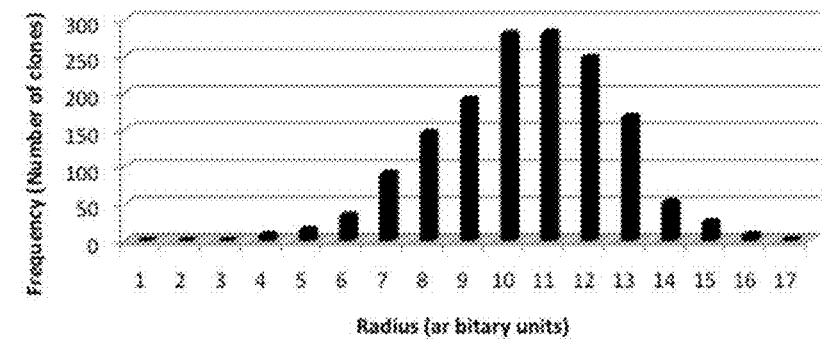
Figure 10:
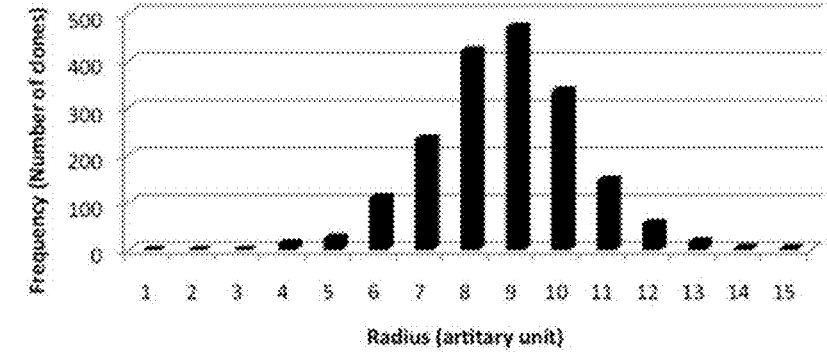

FIG. 10. Size distribution of E. coli colonies after transformation with different YFV-17D cDNA vectors. (A) E. coli EPI-300T colonies after transformation with pACNR-FLYF17DII. (B+C) E. coli EPI-300T colonies after transformation with pShuttle/YFV17D. Plating on plates without inducer (B), or with 0.01% L-arabinose (C) for induction of high copy replication mediated by the inducible high-copy origin.

Figure 11:
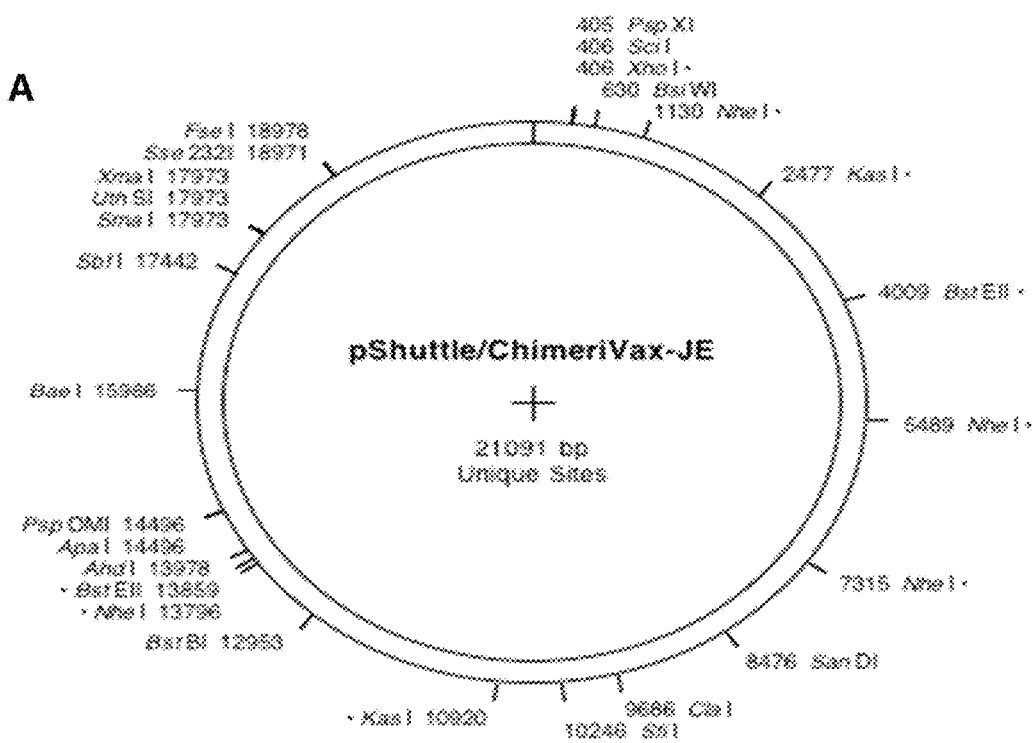
Figure 11:
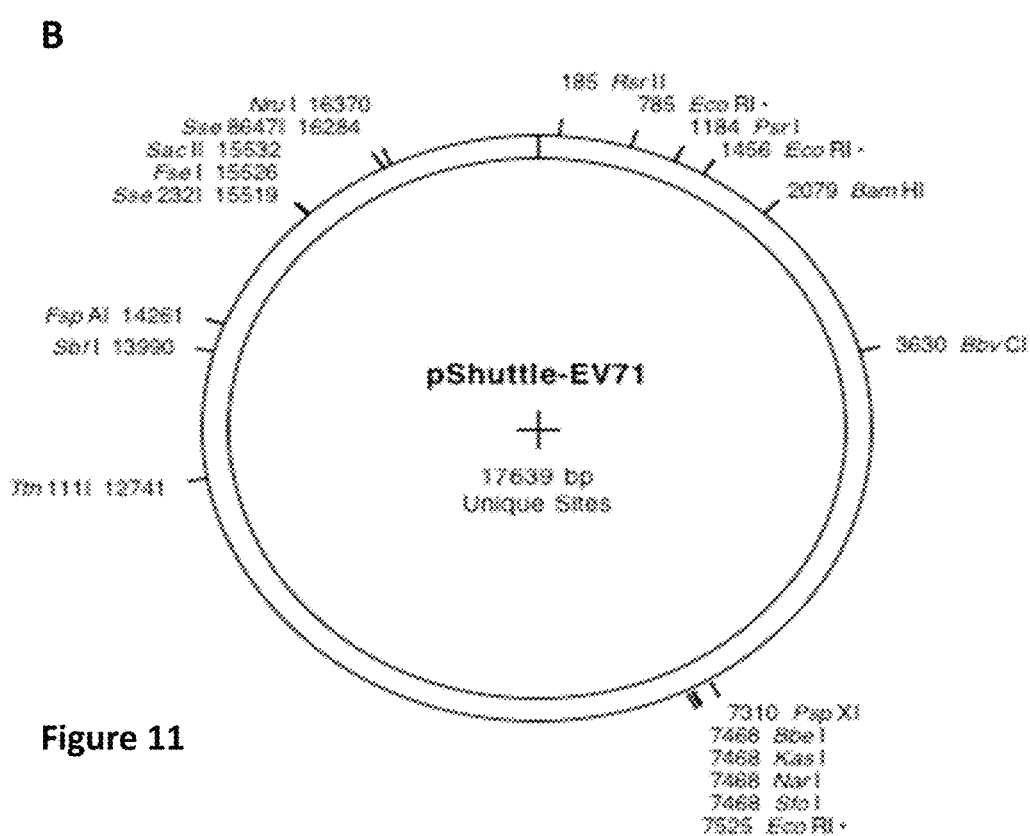

FIG. 11a. Map of pShuttle/ChimeriVax-JE. pShuttle/ChimeriVax-JE contains following the SV40 promotor/origin nt 1-481 and 2452-10862 of YFV-17D, in which 477-2477 of neuroattenuated JEV vaccine strain JE SA14-14-2 are inserted. The second last two last amino acids of the JEV E-ORF are mutated from a histidin to a glycin codon to generate a KasI site, the NS2A and NS4B-ORFs contain two adaptive G4055a and G7349a mutations found in Imojev® changing a methionine to valine in the YFV-17D NS2A and a lysine to glutamine in the NS4B ORFs, respectively. Additional silent mutations generate restriction markers at positions 406 (XhoI), 4009 (BstEII), and 7315 (NheI).

FIG. 11b. Map of pShuttle/ChimeriVax-WN. pShuttle/ChimeriVax-WN contains following the SV40 promotor/origin nt 1-481 and 2452-10862 of YFV-17D, in which 477-2477 of a neuroattenuated derivative of WNV strain NY-99 are inserted. The second last two last amino acids of the WN E-ORF are mutated from a histidin to a glycin codon to generate a KasI site, the NS2A and NS4B-ORFs contain two adaptive G4055a and G7349a mutations found in Imojev® changing a methionine to valine in the YFV-17D NS2A and a lysine to glutamine in the NS4B ORFs, respectively. Additional silent mutations generate restriction markers at positions 406 (XhoI), 4009 (BstEII), and 7315 (NheI).

Figure 12:
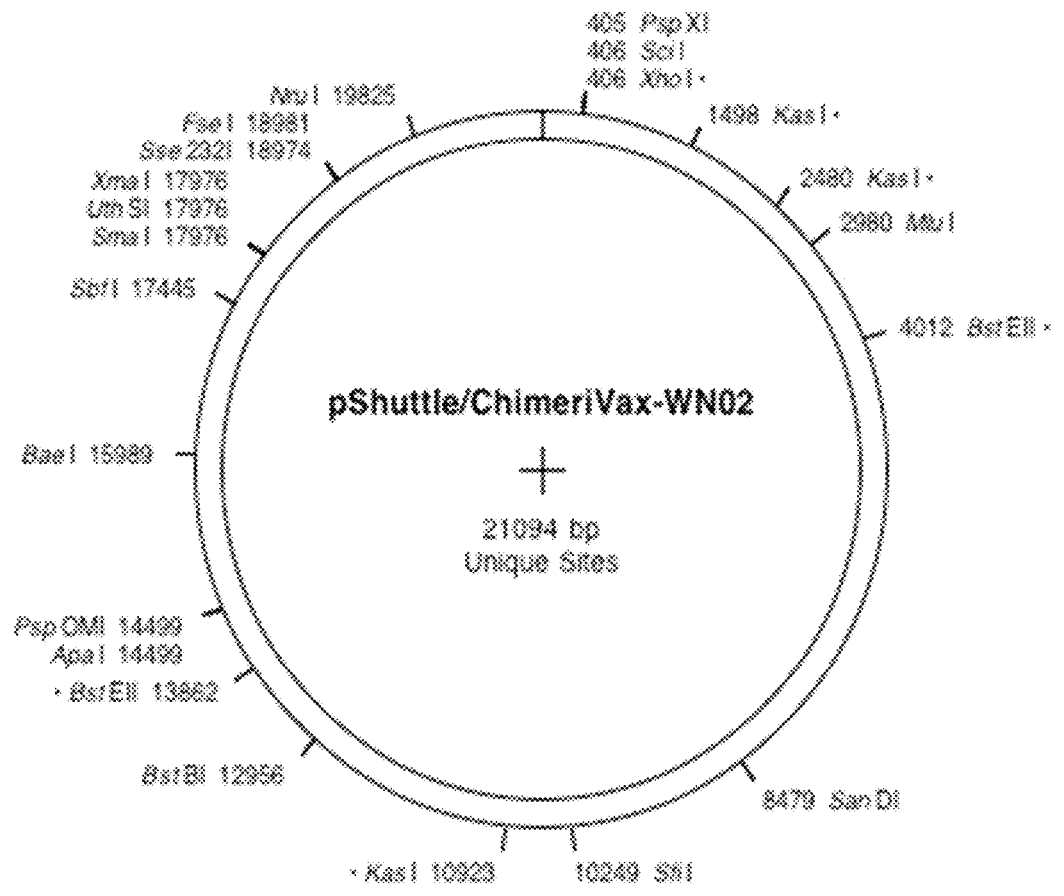

FIG. 12. Map of pShuttle/EV71. pShuttle/EV71 contains the cDNA of EV71 strain BrCr-TR (Genbank AB204852.1) inserted between the SV40 promotor/origin at its 5' terminus, and a 30 nt long polyA repeat plus the hepatitis delta virus ribozyme at its 3' end.

DEFINITIONS

The term "bacterial artificial chromosome (BAC)" refers to a plasmid DNA construct used to clone DNA sequences in bacterial cells, such as E. coli. Typically DNA sequences ranging from 30,000 to about 300,000 base pairs can be inserted into a BAC. The BAC, with the inserted DNA, can be taken up by bacterial cells. As the bacterial cells grow and divide, the BAC DNA is stably maintained within the bacterial cells at a very low copy number per bacterial cell, preferably not exceeding 3 copies per cell, such as at a single copy per cell. The replication of a BAC is initiated at an origin of replication (ori) sequence, typically the oriS sequence. This replication is stringently regulated by gene products, generally the repE and/or repF, encoded by the BAC. The BAC further encodes for proteins, such as parA, B and C, directing the partitioning of the BAC copies to the daughter cells during division. Typically, BAC vectors further comprise selectable markers, such as antibiotic resistance or reporter enzyme markers, such as lacZ allowing for blue white selection. An example of a generally used BAC is the pBeloBac11 (Shizuya et al. (1992) Proc. Natl. Acad. Sci. USA 89, 8794-8797.) The sequence of this vector was reported at GenBank Accession Number U51113. pBeloBac11 is a circular plasmid that includes oriS, the repE gene that produces a protein that initiates and regulates the replication at oriS, and partition genes par A, B, and C. For selection pBeloBac11 includes a chloramphenicol-resistance-encoding gene. The vector also includes a lacZα gene that can be disrupted or eliminated from the vector when an insert is cloned in the BAC.

The term "inducible bacterial ori sequence" refers to a plasmid on sequence that functions in a bacterial host cell and is responsive to amplification-mediating protein(s). Preferably, the replication function of the inducible on is severely suppressed or non-existing in absence of said amplification-mediating protein(s). It is further preferred that in presence of said amplification-mediating protein(s) the inducible on amplifies the plasmid to a high copy number, preferably to more than 20 copies per cell, more preferably to more than 100, for instance to more than 500 or 1000 copies per cell. For use in the present invention it is also preferred, although not essential, that the inducible on responds to a single amplification-mediating protein.

The oriV is particularly useful for use as an inducible bacterial ori in the present invention because of its broad host range, its known capacity to replicate DNA fragments of 100-kb or larger, its high copy number and its requirement for only one inducing protein. Examples of bacterial artificial chromosomes comprising an inducible oriV are pBeloBAC/oriV (Wild et al. (2002) *Genome Res.* 12, 1434-1444) and pBAC-LacZ (Addgene plasmid 13422: pBAC-lacZ, Adgene, Cambridge Mass., USA). The pBAC-lacZ plasmid is a mini-F' that can be replicated in standard *E. coli* strains, but because it is maintained as a single copy episome, it gives low DNA yields. pBAC-lacZ also contains a second, higher copy number origin of replication (oriV) that is only active in the presence of a trans-acting factor encoded by the trfA gene. Transformation of this plasmid in *E. coli* cells expressing trfA from an inducible promoter allows increasing the copy number of the pBAC-lacZ plasmid by inducing the trfA expression. TransforMax™ EPI300™ *E. coli* cells (Epicentre, Madison Wis., USA) contain an inducible mutant trfA gene whose gene product is required for initiation of replication from the oriV origin of replication. The expression of trfA can be induced by addition of L-arabinose to the culture medium, resulting in the activation of the oriV.

"Yeast origin of replication" refers to a sequence within a plasmid, such as a bacterial artificial chromosome, which allows the replication and maintenance of this plasmid in yeast cells. The origin of replication as present in 2μ plasmid (Huberman et al. (1987) *Cell* 51, 473-481; Brewer and Fangman (1987) *Cell* 51, 463-471; Hartley and Donelson (1980) *Nature* 286, 860-865.) has shown to be a suitable on for shuttling the bacterial artificial chromosomes according to the present invention to yeast. Other suitable yeast ORIs have been described (Liachko et al. (2013) *Genome Res.* 23, 698-704, for instance the ARS1 (autonomously replicating sequence 1) and functionally homologous derivatives thereof as used in Yeast Centromeric plasmids (YCp) or the synthetic CEN6/ARSH4 origin (Frazer and O'Keefe (2007) *Yeast.* 24, 777-789).

"viral expression cassette" in the context of the present invention refers to a cDNA of a RNA virus genome flanked by cis-regulatory elements, which upon introduction of said bacterial artificial chromosome in a mammalian cell promote the transcription of said viral cDNA and allow for processing of the transcribed RNA into infectious viral RNA, as described in more detail below.

"infectious viral RNA" refers to viral RNA which, upon introduction in its mammalian host, is sufficient to provide all viral functions required for viral replication and production of infectious viral progeny. This includes (i) serving as a transcriptional template for viral RNA synthesis and genome amplification, and (ii) serving as translational template for synthesis of viral proteins that are required for viral replication. Other accessory functions such as for instance decoying of host cell factors involved in innate antiviral response (Moon et al. (2012) *RNA.* 18, 2029-40. may have to be provided by the infectious viral RNA as well.

"Attenuation" in the context of the present invention relates to the change in the virulence of a pathogen by which the harmful nature of disease-causing organisms is weakened (or attenuated); attenuated pathogens can be used as life vaccines. Attenuated vaccines can be derived in several ways from living organisms that have been weakened, usually from cultivation under sub-optimal conditions (also called attenuation), or from genetic modification, which has the effect of reducing their ability to cause disease.

In a first aspect the present invention provides a bacterial artificial chromosome comprising an inducible bacterial ori sequence, which in presence of a stimulus induces the amplification of said bacterial artificial chromosome within a bacterial cell to a high copy number, preferably to more than 10 copies per cell, more preferably to more than 100, for instance to more than 500 or 1000 copies per cell. Generally, the amplification of said bacterial artificial chromosome as a result of said stimulus does not exceed more than 10,000, for instance no more than 5000 copies per cell. A bacterial artificial chromosome according to the present invention further comprises a viral expression cassette comprising a cDNA of a RNA virus genome flanked by cis-regulatory elements, which upon introduction of said bacterial artificial chromosome in a mammalian cell promote the transcription of said viral cDNA and allow for processing of the transcribed RNA into infectious viral RNA. The viral cDNA comprised in the viral expression cassette of a bacterial artificial chromosome according to the present invention can either be derived from a virus belonging to the group of the positive strand viruses, the negative strand viruses, double-strand RNA viruses or the viruses using an ambience RNA strategy for replication. Said viral cDNA contained in the viral expression cassette can either correspond to that of a wild-type RNA virus genome or be a chimeric viral cDNA construct wherein heterologous DNA sequences have been inserted and/or native viral sequences have been deleted. Preferably, said heterologous DNA sequences encode one or more proteins, which are heterologously expressed by the recombinant virus following the introduction in a mammalian cell of a bacterial artificial chromosome according to the present invention that contains a viral expression cassette comprising such chimeric viral cDNA. Optionally, the bacterial artificial chromosome according to the present invention further comprises a yeast autonomously replicating sequence for shuttling to and maintaining said bacterial artificial chromosome in yeast. The possibility to shuttle to and maintain the bacterial artificial chromosome according to the present invention in a yeast cell provides the advantage that it is amenable for genetic manipulation in both the yeast and bacterial genetic systems.

In absence of a stimulus of the inducible ori, the bacterial artificial chromosomes according to the present invention can be used for archiving and stable cloning of infectious viral cDNA in a bacterial host, while in presence of such stimulus said cDNA can be amplified and subsequently isolated to be used. The bacterial artificial chromosomes according to the present invention are particularly useful in the development, stable maintenance and production of viral cDNA to be used a life vaccine against RNA viral pathogens. Alternatively, said bacterial artificial chromosomes are used for the maintenance and propagation of native or recombinant viruses from cDNA, for instance for research purposes. The bacterial artificial chromosomes according to the present invention, particularly those comprising a yeast origin of replication, have the further advantage that they provide a versatile system for genetically engineering the viral cDNA. This versatility is particularly important in the research and development uses of said bacterial artificial chromosomes, for instance in the design of a cDNA life vaccine against a RNA viral pathogen or in research aiming at elucidating the role and function of certain viral gene products using a reverse genetic approach.

In case the bacterial artificial chromosome according to the present invention comprises a viral expression cassette comprising a cDNA of a positive strand RNA virus genome, it is preferred that said viral cDNA is preceded at its 5' end by an RNA polymerase driven promoter, which upon introduction in a mammalian cell initiates the transcription of the viral cDNA, while at its 3' end it is preferably followed by an element for RNA self-cleaving for cleaving the RNA transcript of said viral cDNA at a set position. Together these cis-regulatory elements allow for the transcription and processing of said viral cDNA into infectious viral RNA when introducing the bacterial artificial chromosome in a mammalian cell. Preferably, said RNA polymerase driven promoter is a RNA polymerase II operated promoter, such as for instance the Cytomegalovirus Immediate Early (CMV-IE) promoter (Thomsen et al. (1984) *Proc. Natl. Acad. Sci. USA* 81, 659-663), the Simian virus 40 promoter (Deboist and Chambon (1981) *Nature* 290, 304-310) or functionally homologous derivatives thereof such as the CMV-IE chicken beta-actin chimeric (CAG) promoter (Niwa et al. (1991) *Gene* 108, 193-199) or inducible versions of said RNA polymerase II operated promoters such as the tetracyline-operator minimal CMV-IE promoter (Gossen et al. (1995) *Science.* 268, 1766-1769; Baron and Bujard (2000) *Methods Enzymol.* 327, 401-421). Alternatively, said RNA polymerase driven promoter is a RNA polymerase I (Russel and Zomerdijk (2006) *Biochem. Soc. Symp.* 73, 203-216) or a RNA polymerase III promoter, such as the U6 or H1 promoter. It is further preferred that said element for RNA self-cleaving is the cDNA of the genomic ribozyme of hepatitis delta virus (Chadalavada et al., (2007) *RNA* 13, 2189-2201) or the cDNA of the functionally homologous hepatitis delta virus-like self-cleaving ribozymes RNA elements such as described in Webb and Luptak (2011) *RNA Biol.* 8, 719-727. Preferably, the viral cDNA of a positive stranded RNA virus contained in said viral expression cassette is derived from a virus belonging to either one of the following viral families the Flaviviridae, including yellow fever virus and other flaviviruses, the hepaciviruses including the hepatitis C virus, the pestiviruses, including the bovine viral diarrhea virus and the classical swine fever virus, the Togaviridae, including the alphavirus, Chikungunya and the rubivirus, rubella virus, the Picornaviridae, including the enteroviruses, such as poliovirus and rhinovirus, and the aphtoviruses, the Coronaviridae, including the HCoV-229E, the SARS-CoV, MERS-CoV (initially described as Novel coronavirus 2012/London1_novel CoV 2012) and the feline coronavirus, and the hepeviruses, including the hepatitis E virus, and the Caliciviridae, including the Norwalkvirus and norovirus. Said viral cDNA contained in the viral expression cassette can either correspond to that of a wild-type RNA virus genome or be a chimeric viral cDNA construct wherein heterologous DNA sequences have been inserted and/or native viral sequences have been deleted, truncated, or mutated. Preferably, said heterologous DNA sequences encode one or more peptides/proteins, which are heterologously expressed by the recombinant virus upon introduction in a mammalian of a bacterial artificial chromosome according to the present invention that contains a viral expression cassette comprising such chimeric viral cDNA.

In a particular embodiment of the present invention the bacterial artificial chromosome according to the present invention contains a viral expression cassette comprising the cDNA of the positive stranded life-attenuated yellow fever virus (YFV)-17D vaccine (FIG. 6). The bacterial artificial chromosomes according to this particular embodiment can be used for the stable cloning and propagation of YFV-17D cDNA. In addition such bacterial artificial chromosomes can serve as a DNA vaccine for live YFV-17D as an alternative for the presently used life attenuated YFV-17D virus vaccine (Stamaril® and similar preparations such as YF-Vax® and others). With respect to the existing YFV-17D virus vaccine the YFV-17 DNA vaccine according to the present invention has the advantage that it can be produced at a lower cost without the need for eukaryotic cell cultures or embryonated chicken eggs. Furthermore, its distribution does not require a cold-chain and it can be needle free administered.

In a more particular embodiment the bacterial artificial chromosome according to the present invention contains a viral expression cassette comprising the cDNA of the life-attenuated YFV-17D vaccine wherein heterologous DNA sequences have been inserted and/or native viral sequences have been deleted. For instance, with reference to U.S. Pat. No. 6,962,708, the nucleotide sequence encoding the prM-E protein in the cDNA of YFV-17D can either be deleted, truncated, or mutated so that the functional prM-E protein of YFV-17D is not expressed, while, a nucleotide sequence encoding the viral envelope protein of a second, different virus, so that the viral envelope protein of the second virus is expressed from the altered genome of the YFV-17D vaccine. Preferably, said second virus is also a flavivirus, such as Japanese Encephalitis (JE, e.g., JE SA14-14-2), Dengue (DEN, e.g., any of Dengue types 1-4; for example, Dengue-2 strain PUO-218) (Gruenberg et al. (1988) *J. Gen. Virol.* 67, 1391-1398.), Murray Valley Encephalitis (MVE), St. Louis Encephalitis (SLE), West Nile (WN), Tick-borne Encephalitis (TBE) (i.e., Central European Encephalitis (CEE) and Russian Spring-Summer Encephalitis (RSSE) viruses), and Hepatitis C (HCV) viruses. Additional flaviviruses for use as the second flavivirus include Kunjin virus, Powassan virus, Kyasanur Forest Disease virus, Zika virus, Usutu virus and Omsk Hemorrhagic Fever virus. Introduction of such bacterial artificial chromosome comprising a chimeric YFV-17D cDNA in a mammalian cell results in the production of a chimeric virus composed of the genes and gene products responsible for intracellular replication belonging to YFV-17D and the genes and gene products of the envelope of the second virus. Since the viral envelope contains antigenic determinants responsible for inducing neutralizing antibodies, the result of infection with the chimeric virus is that such antibodies are generated against the second virus. Alternatively, the nucleotide sequence encoding the prM-E and/or the NS1 protein in the cDNA of YFV-17D can either be deleted, truncated, or mutated so that the functional prM-E and/or NS1 protein of the YFV-17D is not expressed as such, while, a nucleotide sequence encoding for a peptide/protein containing a specific epitope/antigen so that said protein is expressed from the altered genome of the YFV-17D vaccine. Alternatively, cDNAs encoding for heterologous proteins can be inserted at other positions in the cDNA YFV-17D within the bacterial artificial chromosome according to the present invention such as insertions between E and NS1 genes (Bonaldo et al. (2007) *Virol. J.* 4, 115.), insertion in the C gene (Jones et al. (2005) *Virology* 331, 247-259; Schoggings et al. (2012) *Proc. Natl. Acad. Sci. USA* 109, 14610-14615) or the untranslated regions of the YFV-17D cDNA (Jones et al. (2005) cited above). Preferably, said epitope/antigen-containing protein is a tumor antigen, or an antigen of a viral, bacterial of parasitic pathogen. Introduction of such bacterial artificial chromosome comprising a chimeric YFV-17D cDNA in a mammalian cell results in the production of a chimeric virus composed of the genes and gene products responsible for intracellular replication belonging to YFV-17D and a gene and gene product of said epitope/antigen-containing protein. Since the viral envelope contains antigenic determinants responsible for inducing neutralizing antibodies, the result of infection with the chimeric virus is that such antibodies are generated against said epitope/antigen-containing protein.

In case the bacterial artificial chromosome according to the present invention comprises a viral expression cassette comprising cDNA of a negative strand RNA virus genome, the construct as previously described for positive strand RNA viruses has to be modified in a way that the viral genomic cDNA is present in its sense (antigenomic) orientation with respect to the cis elements driving its expression (Radecke et al. (1995) *EMBO J.* 14, 5773-5784), and that it further comprises in sense orientation the cDNA's encoding the viral gene products in sense orientation that together with the viral RNA make part of the viral replicase complex needed for the rescue of viral RNA replication. These cDNA's are flanked by the regulatory cis elements required for expressing these viral gene products that build the viral replicase complex from the plasmid. In the case of the unsegmented negative strand RNA viruses (Conzelmann (1998) *Annu. Rev. Genet.* 32, 123-162) these viral gene products are the N (NP), P and L proteins. Expression of the antigenomic cDNA of the negative strand RNA genome can be driven by either RNA polymerase I or II promoters (Martin et al., (2006) *J Virol.* 80, 5708-5715; while the expression cassette for the viral proteins that build the viral replicase complex may be either polycistronic as encountered naturally in the viruses themselves or monocistronic employing a set of different RNA polymerase promoters (Morita et al. (2012) *Biotechniques* 0, 1-5) for balanced expression of each replicase component. The rescue of negative strand RNA viruses with segmented RNA genomes from an artificial bacterial chromosomes according to the present inventions requires modification with respect to the system as described for negative strand RNA viruses with non-segmented RNA genomes; more particularly an expression cassettes for each genome segment (Neumann and Kawaoka (2004) *Curr. Top. Microbiol. Immunol.* 283, 43-60) driven by appropriate RNA polymerase I and II promoters (Fodor et al. (1999) *J. Virol.* 73, 9679-9682) needs to be incorporated. Due to the limited vector capacity of the plasmid vector systems used for this purpose according to the prior art all the functions required for the rescue of such viruses have to be provided in the prior art by co-transfection of several plasmids, for instance for the rescue of influenza viruses using up to 8 or 12 plasmids was previously described in Hoffmann et al. (2002) *Proc. Natl. Acad. Sci. USA* 99, 11411-11416 and Fodor et al. 1999 (cited above) respectively. The high vector capacity of bacterial artificial chromosomes according to the present invention to contain large inserts, allows expressing negative strand RNA virus genomes or genome segments plus additional viral protein coding sequences from a single bacterial artificial chromosomes in a similar way as for positive strand RNA virus genomes.

Preferably, said viral cDNA of a negative stranded RNA virus contained in said viral expression cassette and the additional expression cassettes needed for rescue of viral replication is derived from a virus belonging to either one of the following viral families the Orthomyxoviridae, including the influenza A, B and C virus, and the paramoxyviruses, including measles virus, mumps virus and respiratory syncytial virus. Said viral cDNA contained in the viral expression cassette can either correspond to that of a wild-type RNA virus genome or be a chimeric viral cDNA construct wherein heterologous DNA sequences have been inserted and/or native viral sequences have been deleted, truncated, or mutated. Preferably, said heterologous DNA sequences encode one or more peptides/proteins, which are heterologously expressed by the recombinant virus upon introduction in a mammalian of a bacterial artificial chromosome according to the present invention that contains a viral expression cassette comprising such chimeric viral cDNA.

In case the bacterial artificial chromosome according to the present invention comprises a viral expression cassette comprising the cDNAs of a double strand RNA virus genome the construct has to be modified such that all viral RNA genome segments needed for the rescue of viral RNA replication as described in Boyce et al. (2008) *J. Virol.* 82, 8339-8348), i.e. 10 RNAs in the case of the bluetongue virus, can be expressed from RNA polymerase II promoters, which allow proper processing, mainly capping, of the nascent transcripts. Alternatively RNA polymerase I and III promoters can be used for this purpose. Preferably, said viral cDNA of a double stranded RNA virus contained in said viral expression cassettes is derived from a virus belonging to either one of the following viral families the of the Reoviridae, including reovirus, rotavirus and bluetongue virus. Said viral cDNAs contained in the viral expression cassette can either correspond to that of a wild-type RNA virus genome or be a chimeric viral cDNA construct wherein heterologous DNA sequences have been inserted and/or native viral sequences have been deleted, truncated, or mutated. Preferably, said heterologous DNA sequences encode one or more peptides/proteins, which are heterologously expressed by the recombinant virus upon introduction in a mammalian of a bacterial artificial chromosome according to the present invention that contains a viral expression cassette comprising such chimeric viral cDNA.

In case the bacterial artificial chromosome according to the present invention comprises a viral expression cassette comprising a cDNA of a virus using an ambisence RNA strategy for replication the construct has to be modified in a way that all viral RNA genome segments needed for the rescue of viral RNA replication as described (Lowen et al. (2004) *Virology* 330, 493-500), are expressed from RNA polymerase I or II promoters. Preferably, said viral cDNA of a virus using an ambisence RNA strategy for replication contained in said viral expression cassette is derived from a virus belonging to either one of the following viral families the Bunyaviridae, including Rift Valley fever virus, Hantaan virus and Schmallenberg virus, and the Arenavirdae, including the Lassa virus. Said viral cDNA contained in the viral expression cassette can either correspond to that of a wild-type RNA virus genome or be a chimeric viral cDNA construct wherein heterologous DNA sequences have been inserted and/or native viral sequences have been deleted, truncated, or mutated. Preferably, said heterologous DNA sequences encode one or more peptides/proteins, which are heterologously expressed by the recombinant virus upon introduction in a mammalian of a bacterial artificial chromosome according to the present invention that contains viral expression cassettes comprising such chimeric viral cDNA.

As described above and illustrated by the examples, the present invention allows to generate high amounts of viral cDNA of a sufficiently high quality to be used in DNA vaccines.

The formulation of DNA into a vaccine preparation is known in the art and is described in detail in for example chapter 6 to 10 of "DNA Vaccines" *Methods in Molecular Medicine* Vol 127, (2006) Springer Saltzman, Shen and Brandsma (Eds.) Humana Press. Totoma, N.J. and in chapter 61 Alternative vaccine delivery methods, Pages 1200-1231, of Vaccines (6$^{th}$ Edition) (2013) (Plotkin et al. Eds.). Details on acceptable carrier, diluents, excipient and adjuvant suitable in the preparation of DNA vaccines can also be found in WO2005042014, as indicated below.

"Acceptable carrier, diluent or excipient" refers to an additional substance that is acceptable for use in human and/or veterinary medicine, with particular regard to immunotherapy.

By way of example, an acceptable carrier, diluent or excipient may be a solid or liquid filler, diluent or encapsulating substance that may be safely used in systemic or topic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N. J. USA, 1991) which is incorporated herein by reference.

Any safe route of administration may be employed for providing a patient with the DNA vaccine. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intramuscular and subcutaneous injection may be appropriate, for example, for administration of immunotherapeutic compositions, proteinaceous vaccines and nucleic acid vaccines.

It is also contemplated that microparticle bombardment or electroporation may be particularly useful for delivery of nucleic acid vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

DNA vaccines suitable for oral or parenteral administration may be presented as discrete units such as capsules, sachets or tablets each containing a pre-determined amount of plasmid DNA, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the DNA plasmids with liquid carriers or finely divided solid carriers or both, and then, if necessary, shaping the product into the desired presentation.

The above compositions may be administered in a manner compatible with the dosage formulation, and in such amount as is effective. The dose administered to a patient, should be sufficient to effect a beneficial response in a patient over an appropriate period of time. The quantity of agent (s) to be administered may depend on the subject to be treated inclusive of the age, sex, weight and general health condition thereof, factors that will depend on the judgement of the practitioner.

Typically the DNA vaccines are used for prophylactic or therapeutic immunisation of humans, but can for certain viruses also be applied on vertebrate animals (typically mammals, birds and fish) including domestic animals such as livestock and companion animals. The vaccination is envisaged of animals which are a live reservoir of viruses (zoonosis) such as monkeys, mice, rats, birds and bats.

In certain embodiments vaccines may include an adjuvant, i.e. one or more substances that enhances the immunogenicity and/or efficacy of a vaccine composition However, life vaccines may eventually be harmed by adjuvants that may stimulate innate immune response independent of viral replication. Non-limiting examples of suitable adjuvants include squalane and squalene (or other oils of animal origin); block copolymers; detergents such as Tween-80; Quill A, mineral oils such as Drakeol or Marcol, vegetable oils such as peanut oil; *Corynebacterium*-derived adjuvants such as *Corynebacterium parvum*; *Propionibacterium*-derived adjuvants such as *Propionibacterium* acne; *Mycobacterium bovis* (Bacille Calmette and Guerin or BCG); interleukins such as interleukin 2 and interleukin 12; monokines such as interleukin 1; tumour necrosis factor; interferons such as gamma interferon; combinations such as saponin-aluminium hydroxide or Quil-A aluminium hydroxide; liposomes; ISCOMt) and ISCOMATRIX (B) adjuvant; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol'EMA; acrylic copolymer emulsions such as Neocryl A640; vaccinia or animal poxvirus proteins; sub-viral particle adjuvants such as cholera toxin, or mixtures thereof.

The present invention is further illustrated by way of the following examples:

EXAMPLES

Example 1

Animals, Viruses, Cells, Bacteria and Yeasts Used in the Experimental Work Presented in Examples 2 and 3

Animals.

129/Sv mice with knockout of both interferon type I and II receptors (AG129 mice; B&K Universal Ltd/UK) were bred in house.

Viruses and Cells.

Vero-B (African green Monkey kidney; American Type Culture Collection (ATCC) CCL-81) and BHK-21 (Baby hamster kidney cells; ATCC CCL-10) cells were obtained from ATCC. All cells were cultured essentially as described (De Burghgraeve et al. (2012) *PLoS ONE* 7, e37244). Yellow fever virus vaccine strain 17D (Stamaril®) was purchased from Sanofi Pasteur MSD, Brussels, Belgium.

Bacteria and Yeast.

Bacterial strains used for routine cloning and propagation of pShuttle-BAC propagation were *E. coli* Top 10 (Invitrogen) and Epi300-T (Epicenter), respectively. Bacteria transformed with full length flavivirus cDNA plasmids pACNR-FL17DII, pACNR-DENV2, and p4 (see below) were routinely grown at 28° C. and plasmid DNA yields increased by chloramphenicol amplification. Shuttle plasmid containing Epi-300T cells were grown at 37° C. and amplified as described below. Yeast strain *Saccharomyces cerevisiae* YPH500 (genotype: MATα ura3-52 lys2-801_amber ade2-101_ochre trp1-Δ63 his3-Δ200 leu2-Δ1) was grown on selective media from Difco-BD Biosciences and Sigma-Aldrich. Transformation of competent yeast cells was carried out using the lithium acetate method, and yeasts were grown at 28° C.

Primers which are used in the experimental section are shown below:

TABLE 1 primer list

| # | primer name | 5' to 3' sequence | SEQ ID NO: |
|---|---|---|---|
| 16 | mRFP(+)_Age/BstX/Nco_Kozak | ATCCACCGGTCCACAACCatggcctcctc cgaggac | 8 |
| 17 | mRFP(-)_Not/Xba | TGATCTAGAGTCGCGGCCGCTTTAg gcgccggtggagtg | 9 |
| 55 | YF17D(-)10862 | AGTGGTTTTGTGTTTGTCATCC | 10 |
| 109 | YF3'-HDrz5'(+) | GGATGACAAACACAAAACCACtGG CCGGCATGGTCCCAGCCTCCTCGCT GG | 11 |
| 110 | HDrzMiddle(+) | GGTCCCAGCCTCCTCGCTGGCGCC GGCTGGGCAACATTCCGAGGGG | 12 |
| 111 | HDrz3'(-) | GTCCCATTCGCCATTACCGAGGGG ACGGTCCCCTCGGAATGTTGCCC | 13 |
| 173 | YF17D(+)1_SP6_Xma/Not | CCCGGGCGGCCGCgcatacgatttaggtgac actatagAGTAAATCCTGTGTGCTAATTG | 14 |
| 194 | Trp1(+)_Nsi/Not/Sal | atgcatgcggccgcgtcgacGGTCGAAAAAA GAAAAGGAG | 15 |
| 195 | 2micron(+)_Nsi/NgoM4/R1 | AtgcatgccggcgaattctgaaccagtcctaaaacgAG | 16 |
| 231 | DENV2(+)1_T7_Xma/Not_tataGGGAGTT | cccgggcggccgctaatacgactcactataGGGAG TTGTTAGTCTACGTGG | 17 |
| 334 | pBABEfwd | Accccgcctcaatcctc | 18 |
| 391 | YF17D(+)10627 | GGTTTCTGGGACCTCCCACCCCAG AGT | 19 |
| 393 | miRNA Cloning Linker 1 | /5rApp/CTGTAGGCACCATCAAT/3dd C/ | 20 |
| 394 | Linker1_reverse/Nhe/Sal | gtcgacgctagcGATTGATGGTGCCTACAG | 21 |
| 425 | HDrz_BstE_Hygro(-) | GGAGGCTGGGACCATGCCGGCCaG GTcACCggtagctcttgatccggca | 22 |

TABLE 1-continued primer list

| # | primer name | 5' to 3' sequence | SEQ ID NO: |
|---|---|---|---|
| 426 | Hygro_BstE_HDrz | tgccggatcaagagctaccGGTgACCtGGCCGGCATGGTCCCAGCCTCC | 23 |
| 453 | SV40(+)-76 | CtccgcccagttccgcccattctccgccccatggctgactaatttttttatttatgcagT | 24 |
| 454 | SV40/YF17D(+)1 | gactaatttttttatttatgcagaggccgaggccgcctcAGTAAATCCTGTGTGCTAAT | 25 |
| 455 | SV40/DV2(+)1 | gactaatttttttatttatgcagaggccgaggccgcctcAGTTGTTAGTCTACGTGGAC | 26 |
| 456 | HDrz(-)5' | CCCTCGGAATGTTGCCCAGCCGGCGCCAGCGAGGAGGCTGGGACCATGCCCGGCCa | 27 |
| 457 | YF17D(-)10862_HDrz | GAGGCTGGGACCATGCCGGCCaGTGGTTTTGTGTTTGTCATCC | 28 |
| 458 | DV2(-)10724_HDrz | GAGGCTGGGACCATGCCGGCCaGAACCTGTTGATTCAACAGCACC | 29 |
| 474 | SV40(-)_HDrz/Pme | CGAGGAGGCTGGGACCATGCCGGCCaGGTCACCgtttaaacGGCCgaggcggcctcggcc | 30 |
| 475 | HDrz(+)_Sfi/Pme/BstE | tttatgcagaggccgaggccgcctcGGCCgtttaaacGGTGACCtGGCCGGCATGGTCCC | 31 |
| 552 | SV40(-)-1 | Gaggcggcctcggcctctgca | 32 |
| 553 | HDrz(+)5' | tGGCCGGCATGGTCCCAGCCT | 33 |
| 856 | SV40/DV4(+)1 | gactaatttttttatttatgcagaggccgaggccgcctcAGTTGTTAGTCTGTGTGGAC | 34 |
| 857 | DV4(-)10649_HDrz | GAGGCTGGGACCATGCCGGCCaGAACCTGTTGGATCAACAACACC | 35 |
| 946 | HA-tag_H1(-) | ttaTGCATAGTCAGGCACGTCATATGGATAggatcc | 36 |
| 947 | YF17D(+)7637_T7p | TCGACTAATACGACTCACTATAGGGggagcgcgaatggaaaaac | 37 |
| 948 | YF17D(-)8136_Sp6p | CGCGCATACGATTTAGGTGACACTATAGgtatcaagaactctcacgg | 38 |
| 208 | | AGTAAATCCTGTGTGCTAATT | 39 |
| 94 | | GGCAATCACGACTCGTTGCG | 40 |
| 953 | | AGATGGTATCTTCATATTTAGAG | 41 |
| 954 | | ACATTTGCTTTGGTCCCTGTCT | 42 |
| 453 | SV40(+)-76 | ctccgcccagttccgcccattctccgccccatggctgactaatttttttatttatgcag | 43 |
| 988 | SV40/hRV14(+)1 | gactaatttttttatttatgcagaggccgaggccgcctcTTAAAACAGCGGATGGGT | 44 |
| 989 | hRV14pA(-)7214_30xA_HDrz | GAGGCTGGGACCATGCCGGCCttttttttttttttttttttttttttttttATAAACTCC | 45 |
| 991 | SV40/EV71(+)1 | gactaatttttttatttatgcagaggccgaggccgcctcTTAAAACAGCCTGTGGGT | 46 |
| 992 | EV71pA(-)7408_30xA_HDrz | GAGGCTGGGACCATGCCGGCCttttttttttttttttttttttttttttttGCTATTCTG | 47 |

TABLE 1-continued primer list

| # | primer name | 5' to 3' sequence | SEQ ID NO: |
|---|---|---|---|
| 990 | HDrz(-)5'#2 | CCCTCGGAATGTTGCCCAGCCGGC GCCAGCGAGGAGGCTGGGACCATG CCGGCC | 48 |

Example 2

Production of Bacterial Artificial Chromosomes According to the Present Invention Containing Viral cDNA of YFV-17D, Dengue Fever Type 2 (DENV2) and Dengue Fever Type 4 (Denv4), Respectively Bacterial artificial chromosomes containing viral cDNA of YFV-17D, Dengue fever type 2 (DENV2) and Dengue fever type 4 (Denv4), respectively were prepared as described below.

Material and Methods

Plasmid constructs (bacterial artificial chromosomes).

All plasmid constructs were generated by standard techniques and confirmed by Sanger sequencing. The inducible shuttle vector pShuttleBAC/Pme was generated in several steps as follows (FIG. 1). First, the lacZ gene present in pBAC/LacZ (Addgene plasmid #13422), a derivative of the arabinose-inducible pBeloBAC/oriV (Wild et al. (2002) Genome Res. 12, 1434-1444), was replaced by a synthetic DNA cassette containing (i) the Simian virus 40 (SV40) promoter/origin (SEQ ID 1) driving the hph gene conferring resistance to hygromycin B, (ii) the synthetic cDNA of the genomic ribozyme of hepatitis delta virus (HDrz) (Chadalavada et al. (2007) RNA 13, 2189-2201) (SEQ ID NO 2), and (iii) the Saccharomyces cerevisiae episomal 2µ plasmid origin and (iv) TRP1 gene conferring prototrophic growth for tryptophan. Building block (i) was PCR amplified from pBABE-hygro (Morgenstern et al. (1990) Nucleic Acids Res. 18, 3587-3996; Addgene plasmid #1765) using primers #334 and #425. Building block (ii-iv) was PCR amplified from pJet(-)/Trp1_2 micron-YF3'_HDrz_BstE using primers #426 and #231. Plasmid pJet(-)/Trp1_2 micron-YF3'_HDrz_BstE is a derivative of pJet1.2/blunt (CloneJET PCR cloning kit, Fermentas) that contains a fusion of the 3'-terminus of the YFV-17D cDNA (comprising viral nt 9466 through 10862) to (ii) the HDrz (assembled from DNA nucleotides #109, 110 and 111), and the (iii+iv) 2µ-TRP1 sequences that were originally derived from pRE637 (Esteban & Fujimura, (2003) Proc. Natl. Acad. Sci. USA 100, 2568-2573) using PCR primers #194 and #195. Building block (i) was fused to (ii-iv) by overlap extension PCR prior to cloning into the SalI sites of pBAC/LacZ to give rise to the pShuttleBAC/SV40_Hygro_HDrz intermediate construct. Subsequently, the hph gene stuffer element was replaced from pShuttleBAC/SV40_Hygro_HDrz for a multiple cloning site (SfiI-PmeI-BstEII) in the final pShuttleBAC/Pme shuttle vector (FIG. 1A) by a inverted PCR spanning the full plasmid using primers #474 and #475 and recirularization by T4 DNA ligase prior to transformation and cloning in E. coli.

The virus expression constructs pShuttle/YF17D, pShuttle/DV2 and pShuttle/DV4 were generated by pasting the cDNAs of YFV-17D (SEQ ID NO 3), DENV2 strain New Guinea-C(NGC) and DENV4 strain Dominica, respectively, into pShuttleBAC/Pme by homologous recombination in S. cerevisiae (FIG. 1B). To that end, the viral cDNAs were amplified by three rounds of PCR introducing terminal extensions containing the −76 bp of the SV40 promoter/origin (Ghosh et al. (1981) Proc. Natl. Acad. Sci. USA 78, 100-104) at their 5' and the 86 nt HDrz sequence (Chadalavada et al., (2007) RNA 13, 2189-2201) at their 3' ends. The first PCR (10 cycles) used virus specific primer combinations #454 plus #457, #455 plus #458 and #856 plus #857, respectively, followed by 10 cycles each using the SV40 and HDrz specific #453 plus #456, and finally #453 plus #111 primers. The respective viral cDNA templates were pACNR-FLYF1DII (Bredenbeek et al., (2003) cited above), pACNR-DENV2 and p4 (Durbin et al. (2001) Am J Trop Med Hyg. 65, 405-413). Plasmid pACNR-DENV2 is a derivative of pACNR-FLYF17D in which the YFV-17D sequence was replaced for the DENV2 NGC cDNA derived pDVWS601 (Gualano et al. (1998) Gen. Virol. 79, 437-446), yet containing additional, translationally silent AgeI and BstEII sites at nt positions 7537 and 10232 of the viral genome, respectively. The linearized vector part needed for recombination was made by an inverted PCR on pShuttleBAC/Pme that was prelinearized with PmeI using primers #552 plus #553. Vector amplicons were treated with DpnI prior to gel purification and transformation into yeast YPH500 to reduce background form carry-over of possibly uncut plasmid template. Yeast clones were grown in the absence of tryptophan to select for recombinant shuttle plasmids. Plasmid DNAs recovered from yeast minipreps were transferred into E. coli Epi300-T cells (Epicenter) and amplified as described (Wild et al. (2000) cited above) by addition of 0.1% (w/v) of L-arabinose to overnight cultures diluted 6-fold into fresh LB medium (supplemented with 20 mM magnesium chloride) and growth for 6 hrs at 37° C. with vigorous shaking.

A YFV-17D variant containing a non-converting lethal mutation in its NS5 ORF (RdRp ΔGDD) was generated by homologous recombination of a 3.6 kb long BglII-PstI restriction fragment derived from the yeast episomal plasmid (YEp) p404Gall/HA-NS5ΔGDD_ura3 comprising a appropriately mutated YFV-17D cDNA downstream of nt 9294 into pShuttle/YF17D linearized by ClaI (downstream of YFV-17D nt 9656) and KasI (upstream of the HDrz nt position +27) to yield pShuttle/YF17DΔGDD.

Results

A series of synthetic DNA constructs (pShuttleBAC series) has been assembled from several DNA building blocks to serve as RNA virus expression plasmids (FIG. 1). The co mMon vector construct pShuttleBAC/Pme is a bacterial artificial chromosome that contains a second origin (oriV) for conditional amplification in E. coli, and a yeast 2µ origin and TRP1 auxotropic marker for episomal replication in *Saccharomyces cerevisiae* (FIG. 1A). The cDNA of the YFV-17D vaccine has been inserted to yield pShuttle/ YF17D by homologous between the SV40 promoter and HDV ribozyme present in pShuttleBAC/Pme (FIG. 1B). The map of pShuttle/YF17D is shown in FIG. 8 (SEQ ID NO 4). The cDNAs of other flaviviruses have been inserted as well. In contrast to prior art flaviviral cDNA clones, such as pACNR-FLYF17DII, pShuttle/YF17D shows an superior genetic stability in *E. coli* (FIG. 2) yet can be induced to produce high plasmid DNA yields.

Example 3

In Vitro and In Vivo Characterization of the Bacterial Artificial Chromosome According to the Present Invention Comprising the cDNA of the YFV-17D Vaccine It was found that the characteristics of YFV-17D expressed from a bacterial artificial chromosome according to the present invention are identical to that of the original vaccine virus (such as efficiency of replication, virus yield and plaque phenotype). Moreover, when this naked YFV-71D plasmid DNA was injected i.p. in AG129 mice, it resulted in the same pathology, morbidity and mortality as the parent virus. This convenient, robust and reproducible system provides a DNA vaccine for YFV at low costs without the need for eukaryotic cell cultures or embryonated chicken eggs. It will no longer require a cold-chain and can be needle free administered.

Material and Methods

In Vitro Transcription, In Vitro Capping and Electroporation.

Plasmid pACNR-FLYF17DII (Bredenbeek et al. (2003) *J. Gen. Virol.* 84, 1261-1268) containing the full-length YFV-17D cDNA was linearized with AflII and purified by proteinase K digestion, phenol-chloroform extraction, and ethanol precipitation. Alternatively, full-length cDNA templates for in vitro transcription (IVT) were made by PCR of pACNR-FLYF17DII using primers #173 and #55 and KAPA High Fidelity DNA polymerase to overcome limited plasmid yields. Run-off RNA transcripts were produced in vitro by using Sp6 RNA polymerase (Ribomax Large Scale RNA production kit, Promega). Transcripts were capped using purified vaccinia virus 7-methyl guanosin transferase (Scriptcap 7mG capping system, Epicenter) and used for electroporation of BHK-21 cells using an excess of total RNA extracted from BHK-21 cells as carrier RNA. Cell culture medium was harvested at the time the transfected cells displayed nearly complete cytopathogenicity. Medium was cleared from cell debris by centrifugation and subsequently used to prepare virus stocks on BHK-21 cells.

Plasmid Transfection

Vero-B cells were seeded in medium containing 10% foetal calf serum into 6-well plates to 70% confluency and transfected the day after with 2.5 µg of plasmid DNA using Transit-LT1 reagent (Mirus) in a DNA-to-vehicle ratio of 1:3. Plasmid pmRFP 1 was co-transfected in a ration of 1:10 to serve as a visual control to assure equal transfection efficacies. For long-term maintenance and production of virus stocks medium was changed after incubation overnight to contain only 2% serum.

Mapping of Viral RNA Ends.

Proper processing of from the pShuttleBAC vector derived viral RNA was analysed by rapid amplification of cDNA ends (RACE). 5' RACE following a novel reverse ligation/amplification protocol has been published in great detail (Dallmeier & Neyts (2013) *Anal. Biochem.* 434, 1-3). 3' RACE of the non-polyadenylated YFV-17D genomic RNA was performed essentially as described before. In brief, 5 µL of DNase I treated total RNA of pShuttle/YF17D transfected Vero cells (approximately 1 µg of RNA) was ligated to the 5'-adenylated and 3'-dideoxycytosine (ddC) modified linker #393 (miRNA Cloning Linker 1, IDT DNA Technologies) by the activity of the K227Q mutant of T4 RNA ligase 2 (New England Biolabs) in the presence of 15% polyethylene glycol (PEG)-8000 in a total reaction volume of 10 µL overnight at 16° C. Ligation products were amplified by One-Step RT-PCR (Qiagen) using the YFV-17D and linker specific primers #391 and #394, respectively. Amplicons of 265 bp were gel purified and cloned into pJet1.2/ blunt (CloneJet PCR cloning kit, Fermentas) after polishing the 3' adenine overhangs generated by the Taq DNA polymerase and analysed by Sanger sequencing.

Detection of Intracellular Viral Replicative RNA Forms.

Northern blotting and detection of viral replicative intermediates after denaturing agarose gel electrophoresis was performed essentially as described (Dallmeier et al. (2008) *PLoS Pathog.* 4, e1000230) with slight modifications regarding the gel system and probe design employed. Briefly, 3 µg of total RNA were heat denatured and separated through a 1% agarose gel in 20 mM 3-(N-morpholino) propane sulfonic acid (MOPS), pH 7.0, 5 mM sodium acetate and 2 mM ethylenediaminetetraacetic acid (EDTA) containing 1% formamide and 0.01 µg ethidium bromide $mL^{-1}$ followed by capillary transfer on positively charged nylon membranes (Roche Diagnostics) in 20×SSC (3M sodium chloride, 300 mM sodium citrate, pH 7.0). Strand-specific DIG labelled single-stranded DNA probes complementary to the 5' end of the NS5 region of YFV-17D (nt 7637-8136) were generated according to Knuchel et al. (2000) *J. Histochem. Cytochem.* 48, 285-294, using primers #947 and #948. Hybridizations and immunodetection was according to the DIG application manual for filter hybridization (Roche Diagnostics).

Virus Quantification by Plaque Assay and RT-qPCR.

Infectious virus released from transfected cells was quantified by virus plaque assay 7 days p.i. of confluent monolayers of BHK-21 cells using a 1% microcristalline cellulose (Avicell) overlay in 0.5× maintenance medium as described before (Kaptein et al. (2010) *Antimicrob Agents Chemother.* 54, 5269-8520). For quantification of viral RNA loads in infected mouse tissues, snap frozen necropsies where disrupted in a Precellys bead mill in RLT buffer (RNeasy, Qiagen), and subsequently total RNA was extracted according to the manufacturer's instruction. Quantitative reverse transcriptase PCR (RT-qPCR) for the YFV-17D RNA was performed exactly as described (Kaptein et al. (2010) cited above) using primers and probes targeting an about 150 nt stretch of the NS3 gene and serial dilutions of same cloned YFV-17D cDNA fragment as standards.

Immunofluorescence Assay.

Cleared supernatants of pShuttle/DV2 transfected BHK-21 cells 7d p.t. were used to inoculate subconfluent Vero-B cultures that were fixed after 5 days in 4% paraformaldehyde and immunostained essentially as described previously (De Burghgraeve et al. (2012) *PLoS ONE* 7, e37244). Intracellular E protein expression was detected either by the DENV2 serotype specific monoclonal-antibody (mAb) 3H5.1 (Millipore), and a secondary Alexa Fluor-488 labelled Ab (Millipore). Following DAPI staining, cells were visualized using a FLoid Cell Imaging station (Life Technologies).

In Vivo Transfection of Mice.

10 to 20 µg plasmid DNA was mixed with 20 µg calcium carbonate microflowers as carrier (Fumoto et al. (2012) *Mol. Pharm.* 9, 1962-1970) in 33% propylene glycol and injected intraperitoneally into adult (about 20 g) AG129 mice. Alternatively, half a dose of life-attenuated YFV-17D vaccine (Stamaril®, Sanofi Pasteur MSD, Brussels) was injected intraperitoneally. Weight and behaviour was monitored on a daily basis.

Results

If transfected into mammalian cells, the transcription of properly processed YFV-17D RNA is launched from pShuttle/YF17D (FIG. 3B) that initiates intracellular self-sustained virus replication (FIG. 3A). Cells transfected with pShuttle/YF17D finally secrete infectious virions that phenotypically cannot be distinguished from the parental YFV-17D virus regarding their ability to induce a cytopathic effect in tissue culture (FIG. 4A-C), the virus yield and the plaque phenotype (FIG. 4D+E). The recombinant viruses thus generated can hence be considered to be biologically identical (quantitatively and qualitatively). Likewise, cells transfected with pShutte/DV2 produce recombinant infectious DENV2 New Guinea strain C (FIG. 5).

Intraperitoneal transfection of pShuttle/YF17D in AG129 mice, an established lethal in vivo mouse model of YFV-17D infection (Meier et al. (2009) *PLoS Pathog.* 5, e1000614; Thibodeaux et al. (2012) *Vaccine* 30, 3180-3187), causes similar virus induced mortality (FIG. 6) and morbidity (FIG. 7) as the genuine YFV vaccine Stamaril®. In conclusion, his convenient, robust and reproducible system may allow developing a DNA vaccine for YFV at low costs without the need for eukaryotic cell cultures or embryonated chicken eggs. It will no longer require a cold-chain and might be needle free administered.

Example 4

Morbidity and Mortality Induced by pShuttle/YF17D (DNA-YFVax) in AG129 Mice Infected by the Subcutaneous Route, and by a Needle-Free Jet Injection of Naked Plasmid DNA To assess the feasibility of other routes for the application of pShuttle/YF17D (DNA-YFVax) than the intraperitoneal route, groups (n=3) of 9 weeks old male AG129 mice (male, weight 22 to 25 g) were injected with 25 µg of DNA-YFVax in 100 µL phosphate buffered saline (PBS) either (i) subcutaneously (s.c.) using a syringe and a G27 needle, or (ii) transdermally (t.d.) by a needle-free jet injector (Injex-30, Injex Pharma GmbH, Berlin Germany) approved for human clinical use for t.d. application of, for instance, insulin or anaesthetics. AG129 injected i.p. with 25 µg DNA-YFVax formulated with calcium carbonate microcristals in 200 µL of 33% propylene glycol as before served as control group. Morbidity and mortality was scored as before, the experiment was terminated after 30 days (see table 2).

TABLE 2

Mortality in male AG129 mice injected with DNA-YFVax via different routes.

| group | mortality | day to death | MDD |
|---|---|---|---|
| intraperitoneal (with CaCO₃) | 0/3 | n.a. | n.a. |
| subcutaneous | 1/3 | 13 n.a., n.a. | n.a. |
| jet injection | 3/3 | 16, 16, 19 | 17 ± 2 |

MDD—mean day to death; n.a.—not applicable

At least some of the AG129 mice injected with DNA-YFVax by the s.c. and t.d. route developed signs of YFV-17D induced disease (weight loss, ruffling of the fur, hunched back, hind limb paralysis) and had to be euthanized. Most importantly, all mice injected by needle-free jet injection died consistently from YFV-17D induced encephalitis within 17±2 days while all i.p. injected control mice survived the time course of the experiment (30 days). The lack of mortality in the control group during course of inspection (compared a MDD of 13±2 presented in example 3) can readily be explained by the higher weight and the male sex of the animals used.

Of note, using calcium carbonate as carrier for DNA-YFVax is not necessarily optimal for vaccine delivery; namely there was occasionally even some inhibitory effect observed in hamsters (see example 5) depending on both, the route of injection and the variability between different batches of calcium carbonate microflowers. In conclusion, DNA-YFVax can be delivered successfully in different formulations and by different routes of injection, including by needle-free jet injection.

Example 5

Seroconversion of Syrian Golden Hamsters Following Immunization with pShuttle/YF17D (DNA-YFVax)

To assess the induction of protective immunity to YFV by the DNA-YFVax, the preclinical Syrian golden hamsters (Mesocricetus auratus) model was used (Tesh et al. (2001) *J Infect Dis.* 183, 1431-1436). To that end groups of female hamsters (8 to 10 weeks old, 90-100 g) were immunized by intraperitoneal (i.p.) injection of either ⅕ dose of Stamaril® (100 µL), or 20 µg pShuttle/YF17D (DNA-YFVax) formulated with calcium carbonate microcristals in 200 µl of 33% propylene glycol as before. In a repeat 10 µg DNA-YFVax was applied instead. Blood was drawn weekly by cardiac puncture under full surgical anaesthesia, sera were harvested by centrifugation and stored frozen at −80° C. Two untreated hamsters served as donors for normal sera. To score for relevant immune correlates of protection, sera were analysed (i) by indirect immunofluorescence assay (IIFA), and (ii) by plaque-reduction neutralization test (PRNT).

Indirect immunofluorescence assay (IIFA). YFV-17D (Stamaril® and DNA-YFVax) specific IgG antibodies in immunized hamster serum were determined using a commercial YFV IIFA kit (EUROIMMUN Medizinische Labordiagnostika AG, Lübeck, Germany, catalogue no. FI-2665-1005G and FI-2665-1010G) validated for human clinical use (Niedrig et al. (2008) *Clin Vaccine Immunol.* 15, 177-81) according to the manufacturer's instructions with some modifications. Hamster serum was diluted 20-, 66-, 200-, 660- and 2000-folds in sample buffer and 30 µL of serum-dilution was applied on the YFV-IIFA slides. Slides were incubated for 30 min at room temperature and then washed in PBS containing 0.2% Tween-20 for 5 min. For detection of antibodies induced in Mesocricetus, FITC-labeled anti-hamster IgG secondary antibody (Jackson Immuno Research Laboratories Inc., catalogue number 307-095-003) was diluted 1:50 in PBS containing 2% BSA and used instead of the anti-human secondary antibody provided in the kit. Slides were counterstained with DAPI, and end point titres determined by fluorescence microscopy.

Plaque reduction neutralization test (PRNT). Neutralizing antibody-titres in yellow fever vaccinated hamster sera were determined using PRNT. In brief, $0.5 \times 10^6$ BHK cells/well were plated in 12 well plates overnight in growth medium (MEM medium supplemented with 10% FCS, 1% sodium bicarbonate and 1% glutamine). All sera were assayed in triplet in serial dilutions 1:20, 1:66, 1:200, 1:660, 1:2000 and 1:6600. 30 µL serum dilution was mixed with in 30 µL assay medium (identical to growth medium but containing only 2% FCS) containing 40 plaques forming of YFV-17D virus (Stamaril®, lot G5400P1, passaged once on Vero-B cells). After this pre-adsorption for 1 h at 37° C., 440 µL assay medium was added, and 500 µL of each mixture added to BHK cells. After 1 h incubation at room temperature, cells were washed and overlayed with assay medium supplemented with LMP agarose (Invitrogen) at a final concentration of 0.5%. Subsequently, cells were cultured for 5 days at 37° C., fixed with 8% formaldehyde for 2 hr and stained with Giemsa stain. Plaques were counted and the 50% neutralization titres were calculated according to Reed and Munch (Reed & Muench (1938) *Am. J. Hyg.* 27, 493-497).

Overall, detection of cross-reacting antibodies by IIFA (table 3), and of neutralizing antibodies by PRNT was consistent (table 4). With regards to vaccine efficacy, DNA-YFVax showed no inferiority to Stamaril®; in both trial groups 2 out of 3 individuals (⅕ Stamaril® vs. 20 µg DNA-YFVax), and 4 out of 5 versus 2 out of 4 individuals (⅕ Stamaril® vs. 10 µg DNA-YFVax) seroconverted to high titers of YFV cross-reactive and neutralizing antibodies (see table 3 and 4). These values can be considered representing full protective immunity (immune correlates of protection), with PRNT titres of >40 are protective in a lethal YFV challenge hamster model (Julander et al. (2011) *Vaccine* 29, 6008-6016). Most importantly, the WHO states a log neutralization index (LNI) of already >0.7 correlates with immunological protection following vaccination in primates, and this applies for humans (WHO position paper (2013) *Wkly. Epidemiol. Rec.* 88, 269-283.). This benchmark of PRNT Log 10 titers >0.7 is exceeded by DNA-YFVax in hamsters by several orders of magnitude, by more than 150-fold (see Table 4).

Moreover, immune response was more homogenous in DNA-YFVax vaccinated individuals if compared to Stamaril®, with seroconversion to high PRNT titers detected consistently within 3 weeks, rather than only after 4 weeks, i.e. 3 weeks later than the other seroconverter from the Stamaril® group.

TABLE 3

YFV cross-reacting antibody responses in Stamaril ® and DNA-YFVax immunized Syrian golden hamsters

| Group | Log10 geometric mean IIFA titer * | | | | |
|---|---|---|---|---|---|
| | d28 | d21 | d14 | d7 | d3/D0 |
| 8-10 wks ♀♀ hamster | ND | | | | |
| 8-10 wks ♀♀ hamster + Stamaril ® (1/5) | 2.3 (2/3) | 2.3 (2/3) | 2.3 (1/3) | 1.3 (1/3) | ND |
| 8-10 wks ♀♀ hamster + Stamaril ® (1/5) | 1.9 (4/5) | | | | |
| 8-10 wks ♀♀ hamster + DNA-YFVax (20 ug) | 2.3 (2/3) | 2.3 (2/3) | 2.3 (1/3) | ND | ND |
| 8-10 wks ♀♀ hamster + DNA-YFVax (10 ug) | 2.3 (2/4) | 2.3 (2/3) | 2.8 (2/4) | ND | ND |

ND = no detection; * (x/x) = no. individuals seroconverted of no. of individuals tested

TABLE 4

Neutralizing antibody responses in Stamaril ® and DNA-YFVax immunized Syrian golden hamsters

| | Animals | Geometric mean PRNT titer day 28 p.i. |
|---|---|---|
| Nonimmunized | H001 | ND |
| | H002 | ND |
| 8-10 wks ♀♀ hamster + Stamaril ® (1/5) | H012 | 405 ± 57 |
| | H013 | ND |
| | H014 | 947 ± 98 |
| 8-10 wks ♀♀ hamster + DNA-YFVax (20 µg) | H015 | ND |
| | H016 | 928 ± 45 |
| | H017 | 822 ± 151 |

ND = no detection

Example 6

Assessing Genetic Instability of Cloned YFV-17D cDNAs (a) Starting material: Large scale plasmid preparations of pACNR-FLYF17DII (Bredenbeek et al. (2003) above and pShuttle/YFV-17D were made using standard techniques. To that end, pACNR-FLYF17DII was transformed in a standard *E. coli* K12 derivative strain, plated on LB-agar containing 100 µg/mL ampicillin and grown overnight at 28° C. (instead of 37° C.) to favour plasmid stability. A small colony was scaled up and grown in LB containing 100 µg/mL at 28° C. under vigorous shaking in two consecutive overnight cultures, to finally reach a 1 L batch culture. This batch was grown overnight at 28° C., and finally amplified by addition of chloramphenicol to a final concentration of 20 µg/mL for another 8 h at 28° C. Similarly, pShuttle/YFV-17D was transformed in *E. coli* strain EPI300-T cells (Epicentre), plated on LB-agar containing 20 µg/mL chloramphenicol, yet grown overnight at 37° C. Latter plasmid was scaled up accordingly, yet all growth was in presence of 20 µg/mL chloramphenicol and at 37° C. The final overnight batch culture was diluted one in six into fresh LB medium containing 20 µg/mL chloramphenicol and 0.01% L-arabinose, and grown for not more than 6 h. Plasmids were purified using standard column affinity purification (Qiagen), dissolved in TE (10 mM Tris-HCl, 1 mM EDTA) to a final concentration of 1 µg/mL, and stored frozen at −20° C.

(b) Colony growth and size. Both plasmids were transformed into *E. coli* EPI300-T and streaked on MacConkey agar (2% peptone, 0.5% NaCl, 1% lactose, 0.15% bile salts, 0.003% neutral red, 0.0001% cristal violet, 1.35% agar) containing appropriate antibiotic as a selective medium. Sterile zirkonia beads (diameter 2.5 mm) were embedded into the agar to serve as calibrators for absolute size measurements. For one aliquot of bacteria transformed with pShuttle/YFV-17D, the agar contained additional 0.01% L-arabinose. After incubation for 16 h at 37° C., pictures were taken using a regular digital camera (Canon Powershot SX10IS) and stored as JPEG files (see FIG. 9). Images were submitted to OpenCFU version 3.8.11 for image analysis regarding colony count and size Geissman (2013) *PLoS One.* 8, e54072.

*E. coli* clones harbouring pShuttle/YFV-17D grew to much larger sizes and to much more homogenous populations (FIG. 9 B) than pACNR-FLYF17DII containing clones (FIG. 9 A). Unexpectedly this seemingly lower toxicity of pShuttle/YFV-17D remains even in the arabinose-induced state (FIG. 9 C). Larger colonies present in the pACNR-FLYF17DII transformant population (FIG. 9 A) most likely contain plasmids with mutations ablating cryptic expression of toxic viral proteins (see Example 6).

Image analysis revealed a significantly higher homogeneity in pShuttle/YFV-17D versus pACNR-FLYF17DII containing clones (Table 5). In fact, the pACNR-FLYF17D containing clones can obviously be divided into at least two subpopulations of different size means, resulting in (i) a large standard deviation from the mean (Table 5), a non-Gaussian size distribution (FIG. 10 A), and (iii) a large difference, for instance, between calculated arithmetic means and median colony sizes (Table 5). By contrast, transformants harbouring pShuttle/YFV-17D show a more homogenous colony size (Table 5) and bell-shaped Gaussian size distribution (FIG. 10 B). Unexpectedly, the latter fully applies to the arabinose-induced state of pShuttle/YFV-17D as well (Table 5 FIG. 10 C).

TABLE 5

Descriptive statistics scoring transformant colony sizes (in mm)

| Descriptive Statistics | pACNR-FLYF17DII | pShuttle/YFV-17D | pShuttle/YFV-17D + ara |
|---|---|---|---|
| Mean | 0.265832815 | 0.583330396 | 0.462981572 |
| Standard Error | 0.002723111 | 0.003093512 | 0.002016904 |
| Median | 0.2 | 0.616 | 0.477 |
| Mode | 0.15 | 0.616 | 0.477 |
| Standard Deviation | 0.154475074 | 0.123314407 | 0.086633004 |
| Sample Variance | 0.023862548 | 0.015206443 | 0.007505277 |
| Kurtosis | 1.265566671 | 0.005301521 | 0.450188526 |
| Skewness | 1.50038333 | −0.216414415 | 0.070062482 |
| Range | 1 | 0.728 | 0.583 |
| Minimum | 0.1 | 0.224 | 0.212 |
| Maximum | 1.1 | 0.952 | 0.795 |
| Sum | 855.45 | 926.912 | 854.201 |
| Count | 3218 | 1589 | 1845 |

Example 7

Mutational Pattern and Frequency During Propagation of Cloned YFV-17D cDNAs in *E. coli*

In order to address the clonal genetic stability of the YFV-17D cDNA containing plasmids, both plasmids as described in Example 6 were transformed into *E. coli* EPI300-T and streaked on MacConkey agar containing appropriate antibiotic as a selective medium as before (see Example 6b). The pACNR-FLYF17DII clones were incubated at 28° C. for 24 h while the pShuttle/YF17D clones were incubated at 37° C. for 16 h.

From each plasmid two series of each 24 to 48 colonies were picked for plasmid growth into 200 μL liquid medium (LB containing appropriate antibiotic supplemented with 20 mM MgCl2). One pACNR-FLYF17DII series was chosen to start from small colonies (pAS series), and one from large colonies (pAL series), respectively. For pShuttle/Y17D where no major size differences could be observed (see Example 6b) colonies with reasonable size differences were chosen as two series of cultures starting from smaller (pSS series) and larger colonies (pSL series), respectively.

Bacteria containing the pACNR plasmid were incubated for 24 h at 28° C. while the pShuttle colonies were incubated overnight at 37° C. and subsequently for 6 h in 600 μL LB containing chloramphenicol and 0.01% arabinose. Part of these cultures [considered as plasmids of passage 0 (P0)] where subjected directly to PCR for amplification (GoTaq Green Mastermix, Promega) using primers #208 and #94 (corresponding YFV-17D nt 1-940, and #953 and #954 (corresponding YFV-17D nt 2500-3600, respectively.

Amplicons were affinity purified (Qiagen) and sequenced directly (Bigdye, Applied Biosystems) using primers #208 and #953, respectively. The cDNA regions analysed were expected to contain cDNA with previously known determinants of toxicity, namely cryptic promoters for illegitimate transcription and translation in *E. coli* in the viral 5' untranslated region (Li et al. (2011) cited above; Pu et al. (2011) cited above) and an especially hydrophobic protein stretch within the viral E-NS1 regions (Yamshchikov et al. (2001) *Virology* 281, 272-280), respectively.

Another part of each cultured clone was diluted 1/100 in fresh medium and grown as before to give rise to a next passage (P1). The latter was repeated up to 10 passages (P10). Plasmids from P1, P3 and P3 where analysed by PCR and sequencing as before. For P10, plasmid was grown in a larger volume of 5 mL of medium and plasmids isolated by a standard alkaline plasmid miniprep procedure. These plasmid minipreps were subjected to (i) PCR analysis (targeting both nt 1-940 and 2500-3600 regions) followed by agarose gel electrophoretic inspection, (ii) direct sequencing (if PCR amplicons could be detected), and (iii) by restriction analysis using PstI. The sequencing result of P0, P1, P3 and P10 are summarized in Table 6 and 7. The results of the PCR and restriction analyses of P10 are summarized in Table 8.

Mutations Found at Early Passages.

Direct sequencing of plasmids from early passages (low passage numbers P0 to P3) of the pAS and pAL series (Table 6) revealed a rather high mutation frequency of up to 13% in an originally clonal plasmid preparation (see Example 6a). Almost all mutations found were nonsense or frameshift mutations (FS) due to introduction of premature stop codons (PMSt) and single nucleotide deletions/insertions, respectively. These mutations obviously completely ablate expression of the full-length YFV-17D open reading frame (ORF). In the pSL series similar mutations were found in P1, though less frequently. In the pSS series at P0, missense mutations were found that will not abolish expression of the viral ORF.

In conclusion, large scale preparations of originally clonal plasmids (see Example 6a) carrying the cDNA of YFV-17D contain readily detectable amounts of mutant plasmid variants. In the case of pACNR-FLYF17DII, the majority of the mutations ablate expression of the full-length viral polyprotein obviously rendering the viral RNA generated from the respective mutant cDNAs replication incompetent. This is the case for more than 10% of all plasmid clones. In the case of pShuttle/YFV-17D, the mutation frequency is lower (less than 10%), and most importantly, a smaller fraction of mutants will hence constitute a priori replication incompetent viruses.

Mutations Found at Passage p10.

When plasmids from pAL and pAS series were analysed at passage P10, the majority of plasmids contained large structural rearrangements that led in 10 out of 48 (21%) and 44 out of 48 (92%) plasmid clones, respectively, to complete failure to amplify the nt 2500-3600 region (Table 8). This was accompanied by an aberrant restriction pattern of the latter mutant plasmids with up to several kilobases of DNA missing from the plasmids. Of note, all mutant clones tested still contained the nt 1-940 region (Table 6) and where thus most likely offspring of the original pACNR-FLYF17DII (Table 8) rather than irrelevant contaminants. Deletion of such toxic cDNA fragments is expected and reported for prior art (Yamshchikov et al. (2001) cited above).

By contrast, similar rearrangements and deletions where never found in the pShuttle-YFV17D series. Here only 2 out of 48 (4%) showed missense mutation that obviously change a possible in frame ATG initiation codon (nt 2957-2959) in the E-NS1 coding region. This will not abolish expression of the viral ORF.

In conclusion, repeated passaging of originally clonal pACNR-FLYF17DII (see example 6a) leads large deletions in the viral cDNA and hence loss of functional cDNA in up to 90% and more of all plasmid clones most obviously rendering the viral RNA generated from the respective mutant cDNAs fully unfunctional. In the case of pShuttle/YFV-17D, the mutation frequency is much lower (less than 5%), and most importantly, no mutants can be observed that constitute a priori replication incompetent viruses that would unable their use as, for instance, life-attenuated DNA vaccine.

TABLE 6

Mutations occurring in cloned YFV-17D cDNA during passaging in *E. coli* (early passages)

| clone series | passage | region | mutant frequency mutant clones out of all clones analysed (%) | type of mutation introduced |
|---|---|---|---|---|
| pAL | P1 | 1-940 | 0/38 (0) | n.a. |
|  | P0 | 2500-3600 | 3/24 (13) | 1x PMSt |
|  |  |  |  | 2x FS |
| pAS | P1 | 1-940 | 0/48 (0) | n.a. |
|  | P3 | 1-940 | 2/91 (2) | 2x FS * |
|  | P0 | 2500-3600 | 1/23 (4) | 1x S ** |
| pSL | P1 | 1-940 | 0/34 (0) | n.a. |
|  | P3 | 1-940 | 0/34 (0) | n.a. |
|  | P0 | 2500-3600 | 2/24 (8) | 2x FS |
| pSS | P0 | 2500-3600 | 1/23 (4) | 1x MS | n.a.—not applicable; PMSt—premature STOP codon generated (nonsense mutation); FS—frameshift due to single nucleotide insertion ore deletion; MS—missense mutation changing codon; S—silent synonymous codon exchange
* one FS observed in non-coding region immediately upstream of start codon
** mixed population of all three alternate codons, but not the synonymous wildtype codon

TABLE 7

Mutations occurring in cloned YFV-17D cDNA during passaging in *E. coli* (late passage P10)

| clone series | passage | region | mutant frequency mutant clones out of all clones analysed (%) | type of mutation introduced |
|---|---|---|---|---|
| pAL | P10 | 1-940 | 0/48 (0) | n.a. |
|  | P10 | 2500-3600 | 10/48 (21) | DEL |
| pAS | P10 | 1-940 | 0/47 (0) | n.a. |
|  | P10 | 2500-3600 | 44/48 (92) | DEL |
| pSL * | P10 | 2500-3600 | 2/48 (4) | 2x MSi | n.a.—not applicable; DEL—large (kilobase range) deletions, for more details see Table 8; MSi—missense mutation changing possible in frame ATG initiation codon
* When overnight cultures derived from passage P0 were plated, pSS and pSL clones grew to the same size of colonies, and were therefore not considered separately anymore at P10.

TABLE 8

Large structural changes in plasmids carrying cloned YFV-17D cDNA during passaging in *E. coli* (passage P10)

| Clone series | Passage | Failure to amplify 1-940 region by PCR mutant clones out of all clones analyzed (%) | Failure to amplify 1-940 region by PCR mutant clones out of all clones analysed (%) | Aberrant restriction pattern mutant clones out of all clones analysed (%) |
|---|---|---|---|---|
| pAL | P10 | 0/48 (0%) | 10/48 (21%) | n.d. |
| pAS | P10 | 0/48 (0%) | 44/48 (94%) | 46/48 (96%) |
| pSL * | P10 | n.d. | 0/48 (0%) | n.d. | n.d.—not determined
* When overnight cultures derived from passage P0 were plated, pSS and pSL clones grew to the same size of colonies, and were therefore not considered separately anymore at P10.

Example 8

Construction of pShuttle/YFV-JE, pShuttle/YFV-WN, and pShuttle/YFV-USU as Expression Vectors for Chimeric Flavivirus Vaccines Recombinant chimeric derivatives of YFV-17D are developed and used as vaccines in which the YFV-17D serves as a vector for heterologous antigens (Guy et al. (2010) *Vaccine* 28, 632-49; US patent application 20100278773), for instance for the surface glycoproteins of other pathogenic flavivirus antigens such as the prM and E proteins of the Japanese encephalitis virus (JEV) and the West Nile virus (WNV), developed as ChimeriVax-JE (Imojev® Sanofi Pasteur-MSD) and ChimeriVax-WN20, respectively. The pShuttle/YFV-17D (DNA-YFVax) according to this invention can be modified as such that is can launch these aforementioned ChimeriVax vaccine viruses directly from transfected plasmid DNA and can thus fully substitute for said life-attenuated ChimeriVax-JE (Imojev®) and ChimeriVax-WN20 vaccines containing life viruses.

The BAC expressing ChimeriVax-JE, pShuttle/ChimeriVax-JE (FIG. 11a), is generated by substituting nt 482-2451 of YFV-17D in pShuttle/YFV17D for nt 477-2477 of neuroattenuated JEV vaccine strain JE SA14-14-2 (Chambers (1999) *J. Virol.* 73(4), 3095-3101; Arroyo et al. (2001) *J. Virol.* 75, 934-942.) plus two adaptive mutation in the NS2A and NS4B genes of the YFV-17D backbone (Pugachev et al. (2004) *J. Virol.* 78, 1032-1038). This is achieved by homologous recombination and joining of three plasmid fragments; two PCR amplicons of pShuttle/YFV17D (nt 7228-481, and nt 3966-7342) and a chimeric YFV-JEV cDNA fragment made by custom DNA synthesis (IDT Integrated DNA Technologies, Haasrode, Belgium). The later comprises nt 359-4105 of ChimeriVax-JE (FIG. 11a). The final construct has a sequence as specified in SEQ ID NO: 5.

The BAC expressing ChimeriVax-WN02, pShuttle/ChimeriVax-WN02 (FIG. 11b), is generated by substituting the prM-E gene region of pShuttle/ChimeriVax-JE for that of region WNV (NY99 strain) that contains three neuroattenuating mutations in the E proteins according to Monath et al. (2006) (*Proc Natl Acad Sci USA.* 103, 6694-6699), namely L 107F, A316V, and K440R. To that end a chimeric YFV-WNV cDNA fragment is made by custom DNA synthesis (IDT Integrated DNA Technologies, Haasrode, Belgium) and recombined into the XhoI (nt 406) and KasI (nt 2477)

sites of pShuttle/ChimeriVax-JE. The final construct has a sequence as specified in SEQ ID NO: 6.

Example 9

Construction of pShuttle/EV71 as Expression Vectors for Different Picornaviruses Enteroviruses are (+)-RNA viruses that belong to the family of picornaviruses of small non-enveloped viruses with a RNA genome in sense-orientation. Typically the genome of picornaviruses is not capped yet carry a 5' terminal covalently attached VPg protein instead. In lack of a cap structure, an internal ribosomal entry site (IRES) recruits the cellular translation machinery to the viral RNA for viral protein expression. In principal, picornaviral replication and production of infectious virus progeny can be launched intracellular following heterologous transcription of the viral genome. In the prior art, the viral genome is expressed from a cDNA that is under control of a phage promoter and transcribed only if the cognate phage RNA polymerase is co-transfected and expressed in a producer cell (two-plasmid system). Likewise the said phage polymerase can be expressed intracellularly upon transduction of the respective cDNAs using a helpervirus such as an recombinant baculovirus (Yap et al. (1997) Virology. 231, 192-200).

Instead of the more complicated approach of the prior art, the picornaviral cDNA can be expressed intracellularly from a derivative of pShuttle-BAC (one-plasmid system) for direct launching of viral replication, as exemplified in the following for the human enterovirus 71 (EV71). To that end, the EV71 genome is cloned as an expression cassette into pShuttle-BAC with a 5' SV40 promoter and a 3' terminal polyA tail followed by a hepatitis delta virus ribozyme. This is accomplished by amplifying the cDNA of EV71 by PCR using primers #991 and #992, and reamplification with primers #453 and #990 to generate a respective expression cassette. Different nucleic acid sources can be used as template for this PCR to appropriately amplify the about 7.4 kb long EV71 cDNA; (i) an already cloned cDNA of EV71 such as that described by Chua et al. (2008) J. Gen. Virol. 89, 1622-1632) and Zhang et al. (2013) Virus Genes. 47, 235-243), or (ii) the product of reverse transcription of any tissue culture, or human or animal tissue derived full-length genomic RNA of EV71. Alternatively, (iii) the EV71 cDNA can be made by custom gene synthesis. Irrespectively of the source of cDNA, the expression cassette thus generated will be inserted into pShuttle/BAC-Pme that has been linearized by restriction endonuclease digest using PmeI, preferably by recombination in yeast. Such a construct has a sequence as specified in SEQ ID NO: 7 for the EV71 strain BrCr-TR (Arita et al. (2005) J. Gen. Virol. 86, 1391-401).

A similar strategy can be followed for the cloning of other enteroviruses such as for instance the human rhinovirus 14 (hRV14), changing only the first set of primers for initial amplification of the viral cDNA. Suitable primers for hRV14 are #988 and #989.

Infectious EV71 and hRV14 viruses will be generated by transfection of the pShuttle/EV71 and pShuttle/hRV14 plasmids, respectively, in cultured mammalian cells such as human cervix carcinoma (HeLa) cells or by transfection in vivo. Attenuated variants thereof can be generated in a similar way and used as life-attenuated vaccines.

The invention claimed is:

1. A method of preparing a vaccine against a flavivirus comprising the steps of:
   a) providing a bacterial host transformed with a BAC (bacterial artificial chromosome) which comprises:
      an inducible bacterial ori sequence for amplification of said BAC to more than 10 copies per bacterial cell, and
      a viral expression cassette comprising a cDNA of an attenuated flavivirus genome and comprising cis-regulatory elements for transcription of said viral cDNA in mammalian cells and for processing of the transcribed RNA into infectious viral RNA,
   b) amplifying the BAC by adding a compound which activates said inducible ori,
   c) isolating the amplified BAC, and
   d) formulating the BAC into a vaccine.

2. The method according to claim 1, wherein said cDNA of the attenuated flavivirus genome is a chimeric viral cDNA construct of a flavivirus genome, wherein a heterologous DNA sequence has been inserted or wherein a native viral sequence has been deleted, truncated, or mutated.

3. The method according to claim 1, wherein said viral expression cassette comprises:
   a cDNA of a positive-strand flavivirus genome,
   a RNA polymerase driven promoter preceding the 5' end of said cDNA for initiating the transcription of said cDNA, and
   an element for RNA self-cleaving following the 3' end of said cDNA for cleaving the RNA transcript of said viral cDNA at a set position.

4. The method according to claim 1, wherein said viral expression cassette comprises a cDNA of a yellow fever virus.

5. The method according to claim 1, wherein said viral expression cassette comprises a cDNA of the live, attenuated YFV-17D yellow fever virus vaccine.

6. The method according to claim 1, wherein said bacterial artificial chromosome further comprises a yeast autonomously replicating sequence for shuttling to and maintaining said bacterial artificial chromosome in yeast.

7. The method according to claim 6, wherein said yeast autonomously replicating sequence is the 2μ plasmid origin or the ARS1 (autonomously replicating sequence 1) or functionally homologous derivatives thereof.

8. The method according to claim 3, wherein said RNA polymerase driven promoter is an RNA polymerase II promoter.

9. The method according to claim 8, wherein said RNA polymerase II promoter is the Cytomegalovirus Immediate Early (CMV-IE) promoter, the Simian virus 40 promoter or functionally homologous derivatives thereof.

10. The method according to claim 3, wherein said RNA polymerase driven promoter is an RNA polymerase I or III promoter.

11. The method according to claim 3, wherein said element for RNA self-cleaving is the cDNA of the genomic ribozyme of hepatitis delta virus or functionally homologous RNA elements.

12. The method according to claim 1, wherein said viral expression cassette comprises a cDNA of the live, attenuated YFV-17D vaccine, wherein one or more of the cDNA sequences coding for the virion surface proteins are either deleted, truncated, or mutated so that such functional virion surface protein of YFV-17D is not expressed and wherein a cDNA sequence coding for a heterologous protein is inserted in the YFV-17D cDNA.

13. The method according to claim 12, wherein said heterologous protein is a virion surface protein of a flavivirus.

14. The method according to claim 1, wherein said viral expression cassette comprises a cDNA of the live, attenuated YFV-17D vaccine, wherein one or more unrelated cDNA sequences are inserted to be expressed as one or more heterologous protein within the viral polyprotein.

15. The method according to claim 1, wherein said viral expression cassette comprises a viral cDNA wherein foreign cDNA sequences are inserted to be heterologously expressed.

16. A vaccine composition comprising a BAC, said BAC comprising:
   an inducible bacterial ori sequence for amplification of said BAC to more than 10 copies per bacterial cell, and
   a viral expression cassette comprising a cDNA of an attenuated flavivirus genome and comprising cis-regulatory elements for transcription of said viral cDNA in mammalian cells and for processing of the transcribed RNA into infectious viral RNA.

17. A method of vaccination against a flavivirus infection comprising the step of administering a BAC, said BAC comprising:
   an inducible bacterial ori sequence for amplification of said BAC to more than 10 copies per bacterial cell, and
   a viral expression cassette comprising a cDNA of an attenuated flavivirus genome, or
   a viral expression cassette comprising a cDNA of an attenuated flavivirus genome and comprising cis-regulatory elements for transcription of said viral cDNA in mammalian cells and for processing of the transcribed RNA into infectious viral RNA.

18. A method for the maintenance of cDNA of a native or recombinant flavivirus genome or for the propagation of native or recombinant viruses from the cDNA, the method comprising the step of propagating a BAC in a bacterial host, the BAC comprising:
   an inducible bacterial ori sequence for amplification of said BAC to more than 10 copies per bacterial cell, and
   a viral expression cassette comprising a cDNA of an attenuated flavivirus genome and comprising cis-regulatory elements for transcription of said viral cDNA in mammalian cells and for processing of the transcribed RNA into infectious viral RNA.

19. The vaccine according to claim 16, wherein said attenuated flavivirus is a yellow fever virus.

20. The vaccine according to claim 19, wherein said yellow fever virus is a live, attenuated YFV-17D yellow fever virus.

\* \* \* \* \*